US012766284B2

(12) United States Patent
Tamal et al.

(10) Patent No.: US 12,766,284 B2
(45) Date of Patent: Oct. 20, 2026

(54) DIFFERENTIAL PRESSURE FLOW METER

(71) Applicant: Imam Abdulrahman Bin Faisal University, Dammam (SA)

(72) Inventors: Mahbubunnabi Tamal, Dammam (SA); Amina Ali Alturaiki, Dammam (SA); Samar Ahmed Ghazal, Dammam (SA); Noor Ali Rashed Al-Khathlan, Dammam (SA); Abdul-Hakeem Alomari, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 581 days.

(21) Appl. No.: 18/467,031

(22) Filed: Sep. 14, 2023

(65) Prior Publication Data

US 2025/0090781 A1 Mar. 20, 2025

(51) Int. Cl.
*G01F 1/42* (2006.01)
*A61M 16/00* (2006.01)
(Continued)

(52) U.S. Cl.
CPC ...... *A61M 16/0672* (2014.02); *A61M 16/024* (2017.08); *G01F 1/42* (2013.01);
(Continued)

(58) Field of Classification Search
CPC ..... G01F 1/42; G01L 13/025; A61M 16/0672
See application file for complete search history.

(56) References Cited

U.S. PATENT DOCUMENTS 5,092,177 A * 3/1992 Varacca .................. G01B 7/18
338/4
5,253,536 A 10/1993 Jones et al.
(Continued)

FOREIGN PATENT DOCUMENTS

CN 101221058 A 7/2008
CN 109803709 A 5/2019
(Continued)

OTHER PUBLICATIONS

Guia, Miguel, et al. "High-flow nasal oxygen therapy in acute hypoxemic respiratory failure: concise review on technology and initial methodology." Turkish thoracic journal 22.6 (2021): 494.*

*Primary Examiner* — Herbert K Roberts
(74) *Attorney, Agent, or Firm* — Oblon, McClelland, Maier & Neustadt, L.L.P.

(57) ABSTRACT

A differential pressure flow meter has a fluid restriction unit and a differential pressure transducer. The fluid restriction unit includes an upstream compartment, a downstream compartment, and an orifice element having a centric bore. The orifice element is located at a junction face of the upstream and downstream compartments. The differential pressure transducer includes a diaphragm compartment having a first sensor coupled to a high-pressure side diaphragm and a second sensor coupled to a low-pressure side diaphragm. The diaphragm compartment is disposed within a chamber having a high-pressure compartment and the low-pressure compartment. The high-pressure compartment is in fluid communication with the upstream compartment via a first fluid outlet port and the low-pressure compartment is in fluid communication with the downstream compartment via a second fluid outlet port.

17 Claims, 51 Drawing Sheets

(51) Int. Cl.
*A61M 16/06* (2006.01)
*G01L 13/02* (2006.01)

(52) U.S. Cl.
CPC .... *G01L 13/025* (2013.01); *A61M 2016/0027* (2013.01); *A61M 2016/003* (2013.01); *A61M 2016/0039* (2013.01); *A61M 2202/0208* (2013.01); *A61M 2205/3334* (2013.01); *A61M 2206/10* (2013.01); *A61M 2209/02* (2013.01); *A61M 2210/0618* (2013.01)

(56) References Cited

U.S. PATENT DOCUMENTS

| | | | | |
|---|---|---|---|---|
| 8,297,125 | B2 * | 10/2012 | Stewart | G01L 19/0038 73/715 |
| 9,427,547 | B2 | 8/2016 | Landis et al. | |
| 2003/0136196 | A1 * | 7/2003 | Wiklund | G01F 1/40 73/716 |
| 2014/0311254 | A1 * | 10/2014 | Evans | G01F 1/42 73/861.61 |
| 2017/0292864 | A1 * | 10/2017 | Zhang | G01F 1/40 |
| 2021/0052844 | A1 | 2/2021 | Oldfield et al. | |

FOREIGN PATENT DOCUMENTS

| | | |
|---|---|---|
| EP | 1 058 570 B1 | 8/2007 |
| EP | 3 524 306 B1 | 8/2021 |

* cited by examiner

```
#include  "Wire.h"
#include  "LiquidCrystal_I2C.h"
LiquidCrystal_I2C lcd (0×27,16,2) ;
float Voltage;
float sensorValue;
float Pressure;
float Primary_Pressure;
float massFlow = 0;  //  Mass flow rate calculated from pressure
float volFlow = 0;  //  Calculated from mass flow rate
 //Constants
float rho = 1.229;  //  Density of air in kg/m^3
float area_1 = 0.000113112;  //  Surface area of the outer diameter in m^2
float area_2 = 0.0000070695;  //  Surface area of the outer diameter in m^2
float dt = 0;
float B=0.4167;  //beta ratio=d2/d1
int i;
void setup ()  {
   Serial.begin  (9600) ;
   lcd.init () ;       //  initialize
lcd.backlight () ;  //To light the background of the LCD
}
void loop ()  {
//Voltage output
sensorValue = analogRead (A0) ;  //  read the analog in value:
Voltage = sensorValue  *  (5.0 / 1023.0) ;//  convert the reading to voltage
```

FIG. 23

```
//To find the pressure
//The voltage-pressure equation from the sensor datasheet [ (V out =
(0.005*p+0.00035) ) ]
// thus: p= (V-Voff) / sensitivity  (kpa)
Primary_Pressure=( (Voltage-0.05) / (3.5) ) ;
Pressure=abs (Primary_Pressure) ;

//To find the flow rate:
//mass flow rate in kg/sec^2:
 massFlow=sqrt ( (abs (Pressure) *2*rho) * (area_2) * (1/ (sqrt (1-pow (B,4) ) ) ) ) ;
//Volumetric flow of air in L/min:
 volFlow = (6000*massFlow) /rho;
 volFlow = abs (volFlow-14.8) ;


//  Print the results to the serial monitor:
Serial.print ("Output Voltage = "  ) ;
Serial.print (Voltage) ;
Serial.print ("       Pressure=    ") ;
Serial.print (Pressure) ;
Serial.print ("KPa  ") ;
Serial.print ("                    Flow rate=   ") ;
Serial.print (volFlow) ;
Serial.println ("  L/min") ;


//To display results in LCD
  lcd.clear () ;
  lcd.setCursor (3,0) ;   // (C,R)
  lcd.print ("Flow rate:  ") ;
  lcd.setCursor (3,1) ;   // (C,R)
  lcd.print (volFlow) ;
  lcd.setCursor (9,1) ;   // (C,R)
  lcd.print ("L/min") ;

```

FIG. 23 (Cont'd)

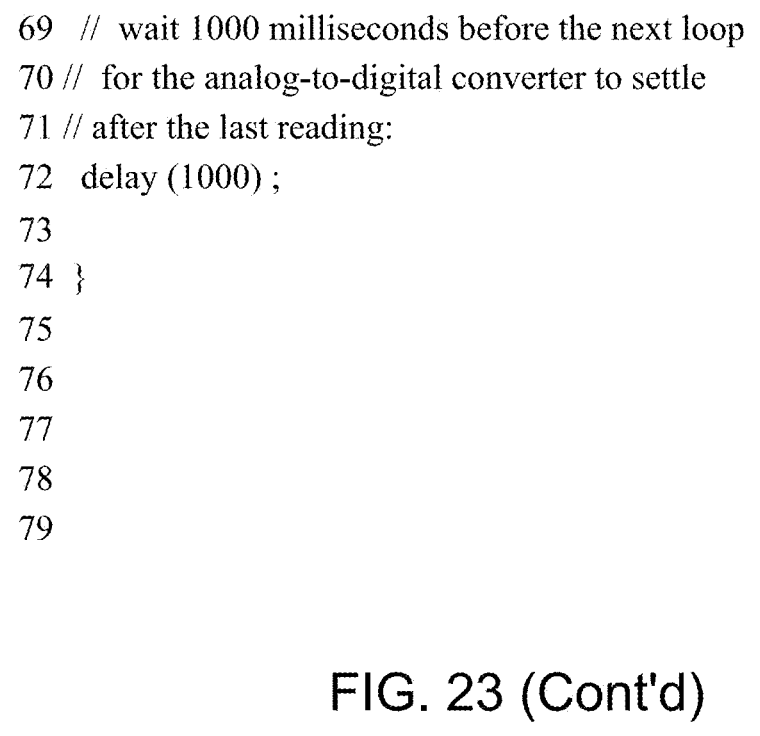

```
//  wait 1000 milliseconds before the next loop
//  for the analog-to-digital converter to settle
// after the last reading:
  delay (1000) ;

}
```

FIG. 23 (Cont'd)

```
x = Arduino ( 'Com5' , 'Uno') ;
Title = 'Arduino Data' ;   % The graph title
X_axix =  ' Elapsed Time   (s) ' ;   %  x-axis
Y_axix =  ' Voltage  (V) ' ;           %  y-axis
legend =  ' Pressure Sensor' ;
yMax  =  6 ;                             % Voltage Maximum
yMin   =  0 ;                            %Voltage minimum
min  =  0 ;                                % set y-min
max  =  6 ;                              % set y-max
delay  =  .1 ;                           % make sure sample faster than resolution
time   =  0 ;
data   =  0 ;
count   =  0 ;
%To plot the curve :
Curve = plot (time, date, 'r' )
hold on
title (Title) ;
xlable (X_axix) ;
ylable (Y_axix) ;
legend (legend) ;
axis ( [yMin yMax min max] ) ;
grid on
tic
while ishandle (Curve)
          data = a.readVoltage ( 'A0' )
          count = count  +  1 ;
          time (count) = toc ;
```

FIG. 25

```
            data (count) = 1/dat (1) ;
            set (Curve, 'XData' , time, 'YData' , data) ;
             axis ( [0 time (count) min max] ) ;
             pause (delay) ;
end'
```

FIG. 25 (Cont'd)

DIFFERENTIAL PRESSURE FLOW METER

BACKGROUND

Technical Field

The present disclosure is directed to a high flow nasal cannula (HFNC) system and a method for monitoring and regulating a flow rate of a fluid composition to a patient during HFNC therapy, and more particularly, relates to a differential pressure flow meter for the HFNC system.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

High flow nasal cannula (HFNC) therapy is used for treating patients suffering from acute respiratory failure. It is a non-invasive method primarily employed for adults with pneumonia leading to hypoxemic respiratory failure, acute pulmonary edema, and patients with chronic obstructive lung diseases. The HFNC device delivers a heated and humidified mixture of oxygen and air to the patient at high flow rates. The device is capable of heating the gases up to the human body temperature, approximately 37° C., with a relative humidity of up to 100%. Additionally, it can deliver a fraction of inspired oxygen ($F_iO_2$) ranging from 0.21-1.00% at flow rates between 5-60 L/min. The flow rate and the fraction of inspired oxygen can be adjusted based on the patient's clinical needs.

When using the HFNC device, it is important to employ an external flow meter for continuous and precise monitoring of gas exchange. The output from the flow meter is utilized to estimate both minute volume and tidal volume. Therefore, it is important for the flow meter to be accurate in order to mitigate any potential side effects resulting from incorrected HFNC settings. Typically, flow meters in the HFNC device are used to monitor individuals undergoing prolonged ventilation. Thus, they should be capable of compensating for the impact of varying gas and vapor compositions. This is a critical consideration since gas composition can significantly change during HFNC therapy, and patients exhale highly humidified gas that may lead to vapor condensation. Given the need for highly accurate flow meters in the HFNC device to ensure patients receive the appropriate gas levels based on their health condition, there is an ongoing crucial need to develop a flow meter that can be positioned between the HFNC device and the patient with the highest possible accuracy and minimal error, enabling continuous long-term monitoring.

Accordingly, it is one object of the present disclosure to develop a precise and universal differential pressure flow meter for HFNC therapy that will monitor both low 2-10 L/min and high 10-60 L/min flow rates. Further, it is an object of the present disclosure to develop a method of monitoring and regulating a flow rate of a fluid composition generated by a nasal cannula as determined by ASME MFC-3M.

SUMMARY

In an exemplary embodiment, a differential pressure flow meter is disclosed. The differential pressure flow meter includes a fluid restriction unit and a differential pressure transducer. The fluid restriction unit includes an upstream compartment, a downstream compartment, a first fluid outlet port on the upstream compartment, a second fluid outlet port on the downstream compartment, and an orifice element having a centric bore. In some embodiments, the orifice element is located at a junction face of the upstream compartment and the downstream compartment, and is in a circular cross section of the fluid restriction unit. In some embodiments, the orifice element is configured to flow a fluid from the upstream compartment to the downstream compartment through an upstream side of the orifice element to a downstream side of the orifice element via the centric bore. In some embodiments, each of the upstream compartment and the downstream compartment are in a shape of a hollow cylinder having substantially the same inner diameter (D) and wall thickness. In certain embodiments, the differential pressure transducer includes a diaphragm compartment having a high-pressure side diaphragm, a low-pressure side diaphragm, a first sensor operatively coupled to the high-pressure side diaphragm, and a second sensor operatively coupled to the low-pressure side diaphragm. In some embodiments, the differential pressure transducer further includes a chamber having a high-pressure compartment and a low-pressure compartment. In some embodiments, the high-pressure compartment and the low-pressure compartment are separated by the diaphragm compartment. In some embodiments, the high-pressure compartment is in fluid communication with the upstream compartment of the fluid restriction unit via the first fluid outlet port, and the low-pressure compartment is in fluid communication with the downstream compartment of the fluid restriction unit via the second fluid outlet port.

In some embodiments, the centric bore of the orifice element has a diameter (d). In some embodiments, d is in a range of 0.224D to 0.742D.

In some embodiments, the orifice element has a semicircle edge, and the semicircle edge has an average thickness of no more than 1.0d.

In some embodiments, the orifice element has a maximum thickness (E), and E is no more than 1.5d.

In some embodiments, the orifice element has a specification of BS 1042-1.1 and BS 1042-1-1.2.

In some embodiments, the first fluid outlet port on the upstream compartment and the second fluid outlet port on the downstream compartment have substantially a same inner diameter of 0.1D.

In some embodiments, a first distance ($d^1$) between a center of the first fluid outlet port on the upstream compartment to the upstream side of the orifice element is substantially same as a second distance ($d_2$) between the center of the second fluid outlet port on the downstream compartment to the downstream side of the orifice element.

In some embodiments, $d_1$ and $d_2$ are in a range of 0.25D to 1.0D.

In some embodiments, the differential pressure flow meter has a length of 40 to 80 millimeters (mm).

In some embodiments, the inner diameter (D) of the upstream compartment and the downstream compartment is in a range of 6 to 20 mm.

In some embodiments, the wall thickness of the upstream compartment and the downstream compartment is in a range of 0.5 to 4 mm.

In some embodiments, the first sensor is at least one selected from the group consisting of a laser senor, and a strain gauge sensor. In some embodiments, the second sensor is at least one selected from the group consisting of a laser senor, and a strain gauge sensor.

In some embodiments, the first sensor and the second sensor are configured to a microcontroller, and the microcontroller is configured to a computing device. In some embodiments, the computing device has a communications interface coupled to the microcontroller.

In some embodiments, the fluid restriction unit is made of polyamide by 3D printing, and has a specification of ISO 5167.

In some embodiments, a diaphragm of the diaphragm compartment is made of silicon.

In another exemplary embodiment, a high flow nasal cannula therapy (HFNC) system for monitoring and regulating a humidified gas flow to patients is disclosed. The system includes a flow source for providing a gas flow, a gas blender for mixing the gas flow, and a humidifier for humidifying the gas flow. In some embodiments, the flow source is in fluid communication with the humidifier via the gas blender. The system further includes the differential pressure flow meter and the humidifier is in fluid communication with the differential pressure flow meter. The system further includes an amplifier for increasing an electrical signal strength generated by the differential pressure flow meter, and a multimeter for monitoring sensitivity of the first sensor and the second sensor of the differential pressure flow meter. The system further includes a microcontroller for controlling and monitoring the electrical signal generated by the differential pressure flow meter, and a computing device for monitoring and regulating the humidified gas flow to patients.

In yet another exemplary embodiment, a method of monitoring and regulating a flow rate of a fluid composition generated by a nasal cannula as determined by ASME MFC-3M is disclosed. The method includes configuring the nasal cannula with the differential pressure flow meter by introducing the fluid composition to the fluid restriction unit via the upstream compartment to generate a high-pressure fluid flow. In some embodiments, the high-pressure fluid flow is in fluid communication with the high-pressure compartment of the chamber via the first fluid outlet port. The method further includes passing the fluid composition through the downstream compartment of the fluid restriction unit to generate a low-pressure fluid flow. In some embodiments, the low-pressure fluid flow is in fluid communication with the low-pressure compartment of the chamber via the second fluid outlet port. The method further includes simultaneously measuring a deformation of the high-pressure side diaphragm caused by the high-pressure fluid flow by the first sensor, and a deformation of the low-pressure side diaphragm caused by the low-pressure fluid flow by the second senor. The method further includes converting the deformation into the electrical signal which is numerically digitally displayed and visually displayed to monitor and regulating a flow rate of the fluid composition generated by the nasal cannula.

In some embodiments, the fluid composition includes air, oxygen, and moisture.

In some embodiments, the flow rate of the fluid composition is in a range of 1 to 80 liters per minute (L/min).

In some embodiments, the method has less than 30% error based on the flow rate of the fluid composition.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 23 illustrates microcontroller code for converting electrical signal into a pressure value and then into a flow rate value, according to certain embodiments;

FIG. 25 illustrates Matlab code for reading output voltage from pressure sensor, according to certain embodiments;

DETAILED DESCRIPTION

Figure 1:
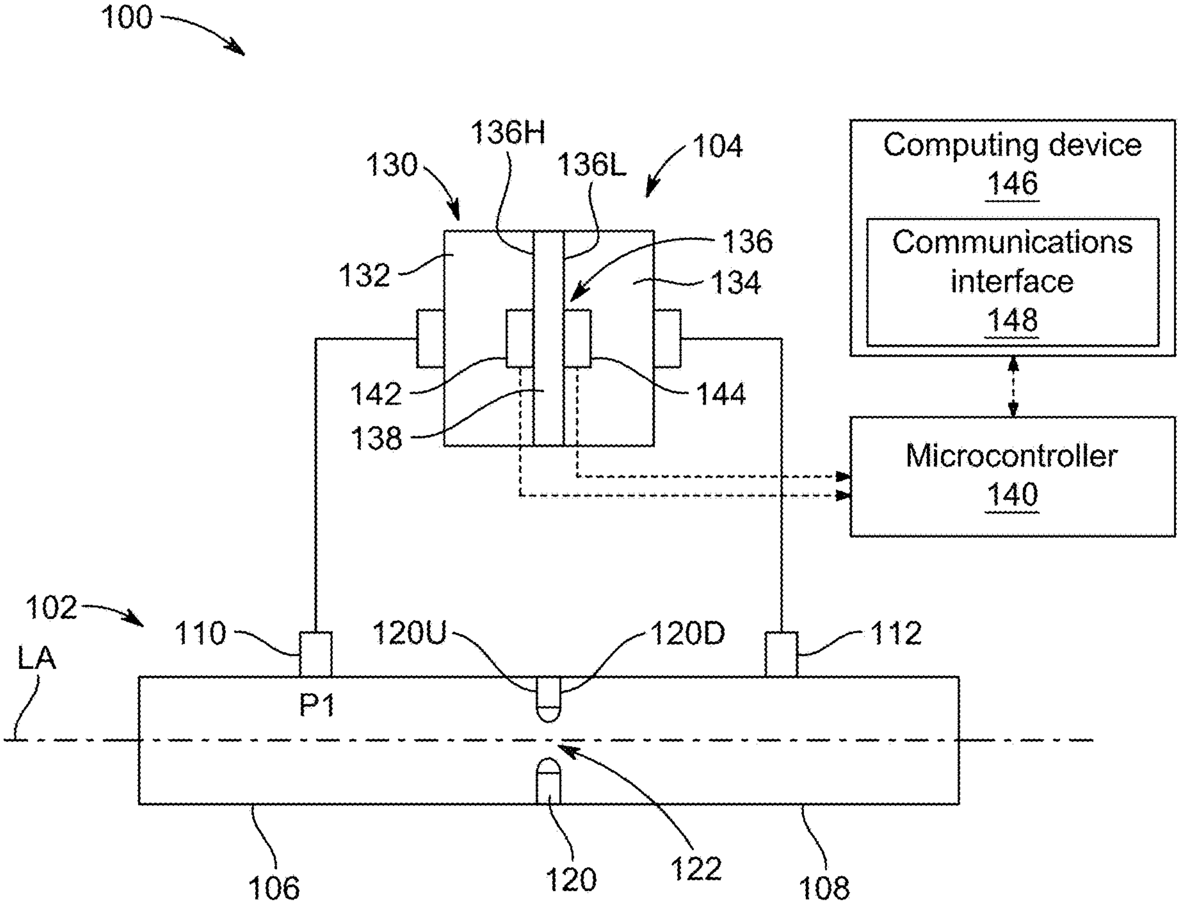
FIG. 1 is a schematic pictorial representation of a differential pressure flow meter, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of this disclosure are directed to a reliable, cost-effective, precise, and universal differential pressure flow meter effective for use in high flow nasal cannula (HFNC) therapy and capable to monitor both low 2-10 L/min and high 10-60 L/min flowrates. The differential pressure flow meter includes a fluid restriction unit for providing a pressure drop in a fluid stream comprising air and oxygen, and a differential pressure transducer to detect the pressure drop, thereby providing an indication about a gas flow rate designed during HFNC therapy. Three different fluid restriction units including orifice, venturi, and nozzle were tested with a fixed outer dimeter and a changeable restriction diameter for each to identify a favorable fluid restriction unit for HFNC therapy. Particularly, output pressure and flow rates were compared between the orifice, the venturi, and the nozzle restriction units to identify the fluid restriction unit with an advantageous combination of high sensitivity and low error. Based on the comparison the orifice restriction unit was identified as the best fluid restriction unit, especially when modified with smoothed edges. The modified orifice performs comparably to ideal values. The differential pressure transducer includes a chamber having a high-pressure compartment and a low-pressure compartment separated by a diaphragm compartment. Sensors are coupled with the diaphragm compartment to communicate with a microcontroller and detect the pressure drop in the fluid stream.

Aspects of the present disclosure are also directed to a HFNC system for monitoring and regulating a humidified gas flow to the patients using the differential pressure flow meter and a method of monitoring and regulating the flow rate of a fluid composition generated by a nasal cannula as determined by ASME MFC-3M.

Referring to FIG. 1, a schematic pictorial representation of a differential pressure flow meter 100 is illustrated, according to an embodiment of the present disclosure. The differential pressure flow meter 100 includes a fluid restriction unit 102 and a differential pressure transducer 104. The fluid restriction unit 102 includes an upstream compartment 106 and a downstream compartment 108 extending from the upstream compartment 106 along a longitudinal axis 'LA'. The fluid restriction unit 102 further includes a first fluid outlet port 110 defined on the upstream compartment 106 and a second fluid outlet port 112 defined on the downstream compartment 108. The fluid restriction unit 102 further includes an orifice element 120 having a centric bore 122. The orifice element 120 is located at a junction face of the upstream compartment 106 and the downstream compartment 108. The orifice element 120 is configured to flow or permit passage of a fluid from the upstream compartment 106 to the downstream compartment 108 through an upstream side 120U of the orifice element 120 to a downstream side 120D of the orifice element 120 via the centric bore 122.

The differential pressure transducer 104 includes a chamber 130 having a high-pressure compartment 132 and a low-pressure compartment 134. The high-pressure compartment 132 is in fluid communication with the upstream compartment 106 of the fluid restriction unit 102 via the first fluid outlet port 110 and the low-pressure compartment 134 is in fluid communication with the downstream compartment 108 of the fluid restriction unit 102 via the second fluid outlet port 112. The differential pressure transducer 104 further includes a diaphragm compartment 136 having a high-pressure side diaphragm 136H and a low-pressure side diaphragm 136L. Particularly, the diaphragm compartment 136 includes a diaphragm 138 defining the high-pressure side diaphragm 136H and the low-pressure side diaphragm 136L. In some embodiments, the diaphragm 138 of the diaphragm compartment 136 is made of silicon. The diaphragm compartment 136 is disposed within the chamber 130 to separate the high-pressure compartment 132 and the low-pressure compartment 134 of the chamber 130.

The differential pressure transducer 104 further includes a first sensor 142 operatively coupled to the high-pressure side diaphragm 136H of the diaphragm compartment 136 and a second sensor 144 operatively coupled to the low-pressure side diaphragm 136L of the diaphragm compartment 136. In some embodiments, the first sensor 142 is at least one selected from the group consisting of a laser sensor and a strain gauge sensor. Similarly, the second sensor 144 is at least one selected from the group consisting of a laser sensor and a strain gauge sensor. In some embodiments, the first and the second sensors 142, 144 may be any devices that can detect deflection of the diaphragm 138 in the diaphragm compartment 136. The first sensor 142 and the second sensor 144 are configured to communicate with a microcontroller 140. Particularly, the first sensor 142 and the second sensor 144 are configured to be in communication with the microcontroller 140 such that input signals indicative of a deflection of the diaphragm 138 generated by the first and second sensors 142, 144 may be communicated with the microcontroller 140 to determine the deflection of the diaphragm 138. The microcontroller 140 is further configured to a computing device 146. The computing device 146 has a communications interface 148 coupled to the microcontroller 140.

Figure 2:
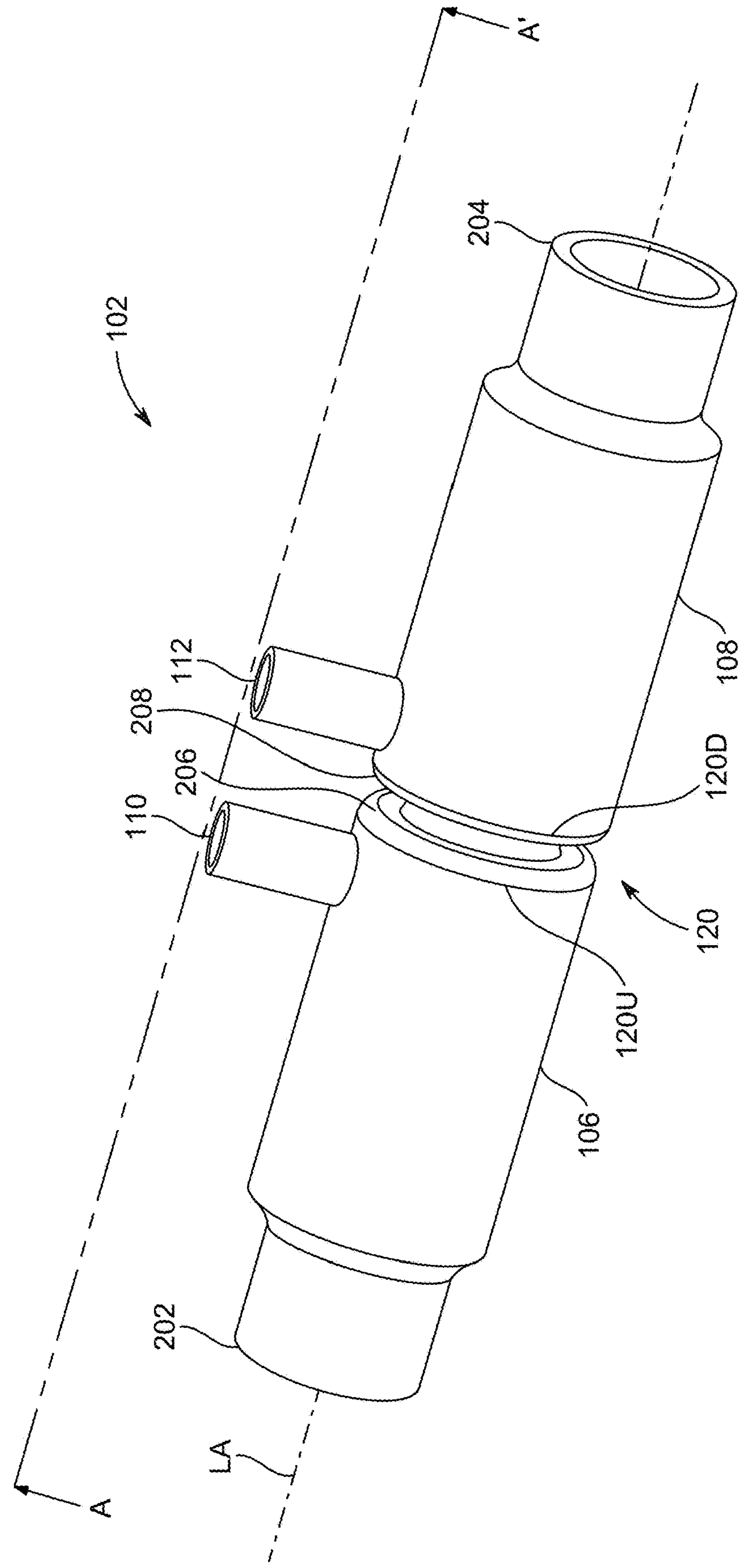
FIG. 2 is a schematic perspective view of a fluid restriction unit of the differential pressure flow meter, according to certain embodiments.

Referring to FIG. 2, a schematic perspective view of the fluid restriction unit 102 is illustrated, according to an embodiment of the present disclosure. The upstream compartment 106 includes a first end 202 configured to fluidly couple with a fluid conduit (not shown) and the downstream compartment 108 includes a first end 204 configured to fluidly couple with a nasal cannula, as such the fluid conduit and the fluid restriction unit 102 together form a passage for a continuous flow of the fluid therethrough. A second end 206 of the upstream compartment 106 and a second end 208 of the downstream compartment 108 are together configured to define the orifice element 120 at the junction face of the upstream compartment 106 and the downstream compartment 108. The junction face may be defined as a center portion of the fluid restriction unit 102 at which the second ends 206, 208 of the upstream compartment 106 and the downstream compartment 108, respectively, meet to define the orifice element 120. In some embodiments, the fluid restriction unit 102 is made of polyamide by 3D printing, and has a specification of ISO 5167 [See: Measurement of fluid flow by means of pressure differential devices inserted in circular cross-section conduits running full, ISO 5167, which is incorporated herein by reference in its entirety].

The first fluid outlet port 110 is defined at the second end 206 of the upstream compartment 106 adjacent the orifice element 120 and the second fluid outlet port 112 is defined at the second end 208 of the downstream compartment 108 adjacent the orifice element 120. Particularly, the first fluid outlet port 110 is defined adjacent the upstream side 120U of the orifice element 120 and the second fluid outlet port 112 is defined adjacent the downstream side 120D of the orifice element 120. The first fluid outlet port 110 and the second fluid outlet port 112 are configured to fluidly couple the differential pressure transducer 104 with the fluid restriction unit 102.

Figure 3A:
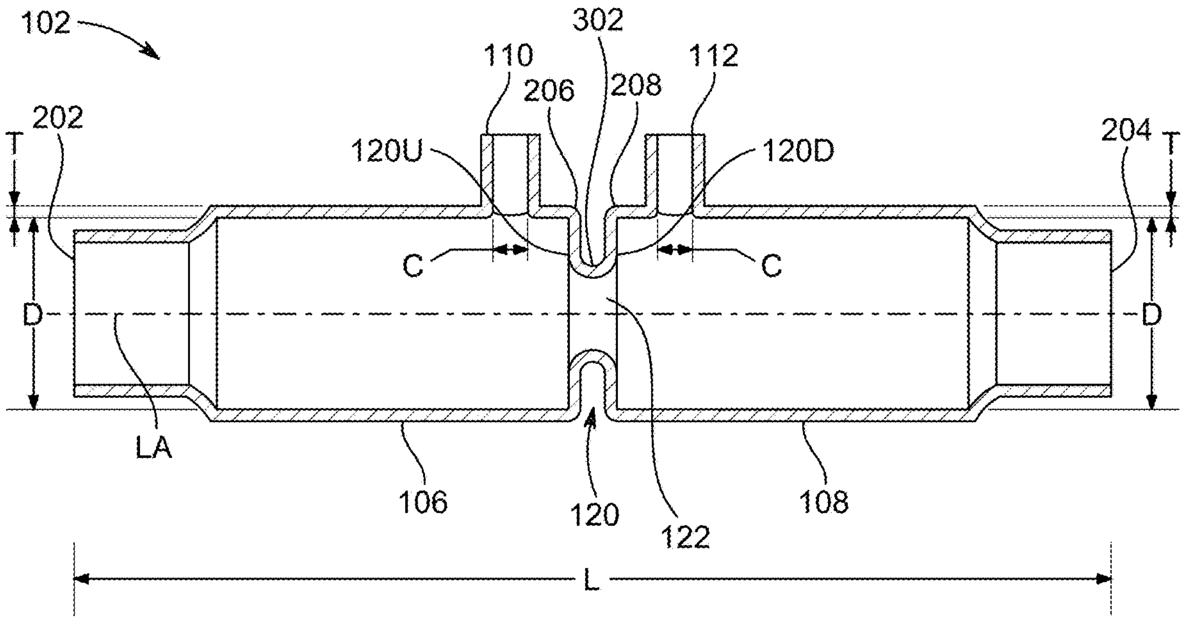
FIG. 3A is a schematic cross-sectional view taken along a sectional line A-A' of the fluid restriction unit of FIG. 2, according to certain embodiments.

Referring to FIG. 3A, a schematic cross-sectional view taken along a sectional line A-A' of the fluid restriction unit 102 of FIG. 2 is illustrated, according to an embodiment of the present disclosure. The upstream compartment 106 and the downstream compartment 108 of the fluid restriction unit 102 are in a shape of a hollow cylinder. The upstream compartment 106 has an inner diameter 'D' and a wall thickness 'T' which are substantially same as an inner diameter and a wall thickness of the downstream compartment 108, respectively. As such, the inner diameter of both the upstream compartment 106 and the downstream compartment 108 is designated by 'D' and the wall thickness of both the upstream compartment 106 and the downstream compartment 108 is designated by 'T'. In some embodiments, the inner diameter 'D' of both the upstream compartment 106 and the downstream compartment 108 is in a range of 4 to 40 millimeters (mm), preferably 6 to 20 mm, preferably 7 to 18 mm, preferably 8 to 16 mm, preferably 9 to 14 mm, or even more preferably 10 to 12 mm. Other ranges are also possible. Particularly, the inner diameter 'D' of the upstream and downstream compartments 106, 108 is about 12 mm, which is the same size as a nasal cannula. In some embodiments, the wall thickness 'T' of both the upstream compartment 106 and the downstream compartment 108 is in a range of 0.1 to 8 mm, preferably 0.5 to 4 mm, preferably 0.8 to 3.5 mm, preferably 1.1 to 3.0 mm, preferably 1.4 to 2.5 mm, or even more preferably 1.7 to 2 mm. Other ranges are also possible. Particularly, the wall thickness 'T' of both the upstream and downstream compartments 106, 108 is about 2 mm. The upstream compartment 106, the downstream compartment 108, and the orifice element 120 together define a length 'L' of the fluid restriction unit 102 along the longitudinal axis 'LA', which is otherwise referred to as the length 'L' of the differential pressure flow meter 100. In some embodiments, the length 'L' of the differential pressure flow meter 100 is in a range of 20 to 200 mm, preferably 30 to 150 mm, preferably 40 to 80 mm, or even more preferably 50 to 60 mm. Other ranges are also possible. The first fluid outlet port 110 defined on the upstream compartment 106 has an inner diameter 'C' which is substantially same as an inner diameter of the second fluid outlet port 112 defined on the downstream compartment 108. As such, the inner diameter of both the first fluid outlet port 110 and the second fluid outlet port 112 is designated by 'C'. In some embodiments, the inner diameter 'C' of each of the first fluid outlet port 110 and the second fluid outlet port 112 is about 0.5D, about 0.4D, about 0.3D, about 0.2D, or preferably about 0.1D, i.e., 0.1 times the inner diameter 'D' of the upstream compartment 106 and the downstream compartment 108.

Figure 3B:
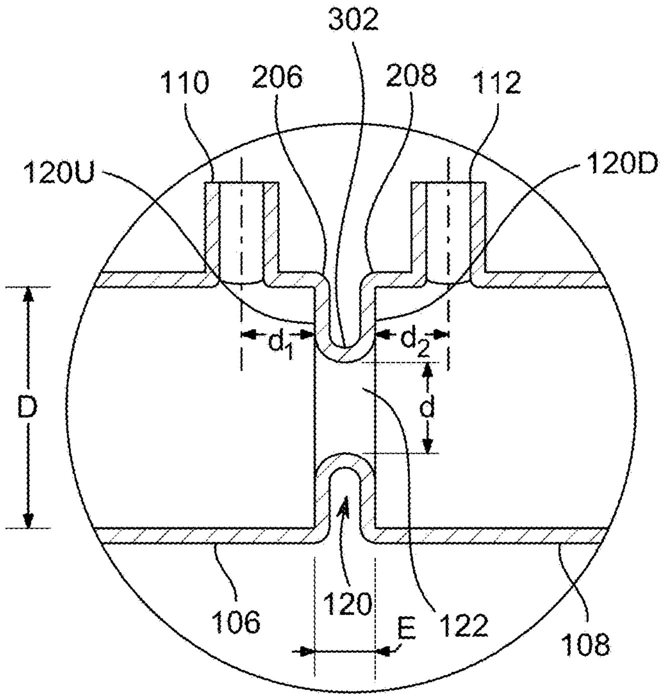
FIG. 3B is an enlarged view of an orifice element of the fluid restriction unit of FIG. 3A, according to certain embodiments.

Referring to FIG. 3B, an enlarged view of the orifice element 120 of FIG. 3A is illustrated. Referring to FIGS. 3A and 3B, the first fluid outlet port 110 is defined on the upstream compartment 106 adjacent the upstream side 120U of the orifice element 120 at a first distance '$d_1$'. Particularly, the first distance '$d_1$' is defined between a center of the first fluid outlet port 110 on the upstream compartment 106 to the upstream side 120U of the orifice element 120. Similarly, the second fluid outlet port 112 is defined on the downstream compartment 108 adjacent the downstream side 120D of the orifice element 120 at a second distance '$d_2$', which is substantially same as the first distance '$d_1$'. Particularly, the second distance '$d_2$' is defined between a center of the second fluid outlet port 112 on the downstream compartment 108 to the downstream side 120D of the orifice element 120. The first fluid outlet port 110 and the second fluid outlet port 112 are configured to fluidly couple the differential pressure transducer 104 with the fluid restriction unit 102. In some embodiments, the first distance '$d_1$' and the second distance '$d_2$' are in a range of 0.25D to 1.0D, i.e., 0.25 to 1.0 times the inner diameter 'D' of the upstream and downstream compartments 106, 108, preferably 0.23D to 0.12D, preferably 0.21D to 0.14D, or even more preferably 0.19D to 0.16D. Other ranges are also possible. In some embodiments, the first distance '$d_1$' and the second distance '$d_2$' are 5 mm. Alternatively, a distance between pressure tapping at each of the first fluid outlet port 110 and the second fluid outlet port 112 is set to be 5 mm from each side of the orifice element 120, following the standard corner tap method according to the orifice standards [See: Reader-Harris, Michael. "Orifice Design." Orifice Plates and Venturi Tubes. Springer, Cham, 2015. 33-76, which is incorporated herein by reference in its entirety].

The orifice element 120 includes the centric bore 122 to allow flow of the fluid from the upstream compartment 106 to the downstream compartment 108. The orifice element 120 has a circular cross-section having an outer diameter equal to the inner diameter 'D' of the upstream and the downstream compartments 106, 108. In some embodiments, the centric bore 122 of the orifice element has a diameter 'd' which is in a range of 0.224D to 0.742D, i.e., 0.224 to 0.742 times the inner diameter 'D' of the upstream and the downstream compartments 106, 108, preferably 0.25 to 0.65D, preferably 0.3 to 0.6D, preferably 0.35 to 0.55D, or even more preferably 0.4 to 0.5D. Other ranges are also possible. In some embodiments, the orifice element 120 has a maximum thickness 'E'. In an example, the orifice element 120 may be defined in the form of a circular plate having the maximum thickness 'E'. The circular plate may have a single layer or two layers, e.g., formed by folding a single layer plate. In some embodiments, the maximum thickness 'E' is no more than 1.5d, i.e., 1.5 times the diameter 'd' of the centric bore 122, preferably no more than 1.3d, preferably no more than 1.1d, preferably no more than 0.9d, preferably no more than 0.7d, or even more preferably no more than 0.5d. Other ranges are also possible. In some embodiments, the orifice element 120 has an inner edge 302 facing towards to the axis LA. The inner edge has a semicircular cross-sectional profile with a radius "E". Particularly, the centric bore 122 of the orifice element 120 has the semicircle edge 302 to smoothen the flow of the fluid. In some embodiments, the semicircle edge 302 has an average thickness of no more than 1.0d, i.e., 1.0 times the diameter 'd' of the centric bore 122, preferably no more than 0.9d, preferably no more than 0.8d, preferably no more than 0.7d, preferably no more than 0.6d, or even more preferably no more than 0.5d. Other ranges are also possible. In some embodiments, the orifice element 120 has a specification of BS 1042-1.1 and BS 1042-1-1.2.

Figure 4:
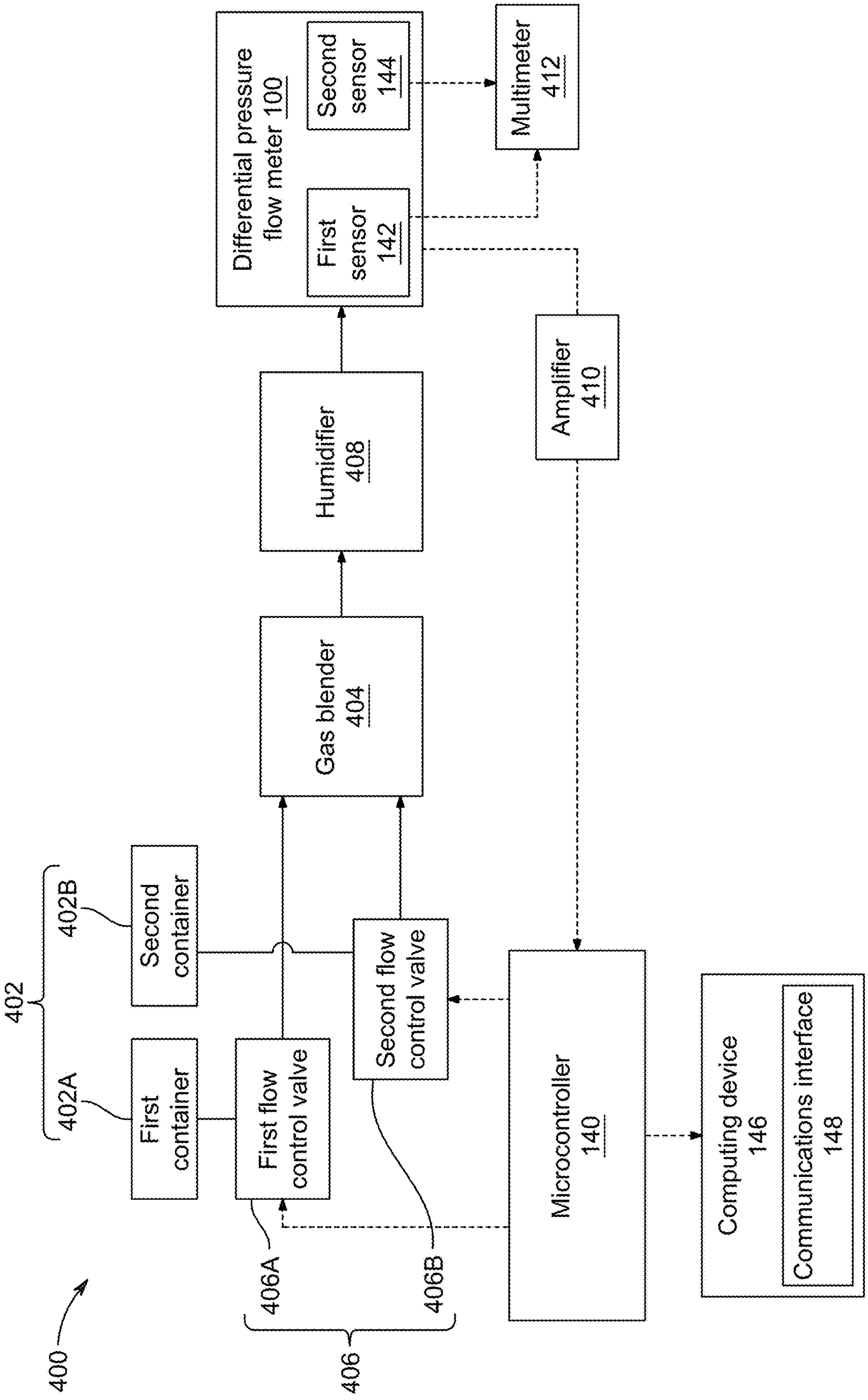
FIG. 4 is a schematic block diagram of a high flow nasal cannula (HFNC) therapy system, according to certain embodiments.

Referring to FIG. 4, a schematic block diagram of a high flow nasal cannula (HFNC) therapy system 400 is illustrated, according to an embodiment of the present disclosure. The high flow nasal cannula (HFNC) therapy system 400 is hereinafter alternatively referred to as 'the system 400' or 'the HFNC system 400' or 'the HFNC device 400'. The HFNC device 400 may be generally defined as a device that accomplishes a reduction of nasopharyngeal airway resistance, thereby leads to improved ventilation and oxygenation through the application of positive pressure environment. The differential pressure flow meter 100 of the present disclosure is attached to the nasal cannula between the HFNC device 400 and the patient.

The system 400 may be used for monitoring and regulating a humidified gas flow to patients, when the patients are subjected to HFNC therapy. The system 400 includes a flow source 402 for providing a gas flow to the patient. In an embodiment, the flow source 402 may be a container for storing the gas required for the HFNC therapy. In an example, the gas may be air, oxygen, or a combination of air and oxygen. In some embodiments, the system 400 may include a first container 402A for storing air and a second container 402B for storing oxygen. The first container 402A and the second container 402B are collectively or individually referred to as the flow source 402 unless otherwise specifically mentioned.

The system 400 further includes a gas blender 404 for mixing the gas flow. The gas blender 404 is fluidly coupled to the flow source 402. Particularly, the first container 402A is fluidly coupled with the gas blender 404 to supply the air to the gas blender 404 and the second container 402B is fluidly coupled with the gas blender 404 to supply the oxygen to the gas blender 404. In some embodiments, a flow control valve 406 may be fluidly coupled between the flow source 402 and the gas blender 404. In an embodiment, a first flow control valve 406A may be fluidly disposed between the first container 402A and the gas blender 404 to control flow of air to the gas blender 404 and a second flow control valve 406B may be fluidly disposed between the second container 402B and the gas blender 404 to control flow of oxygen to the gas blender 404. The first flow control valve 406A and the second flow control valve 406B are collectively or individually referred to as the flow control valve 406 unless otherwise specifically mentioned. The gas blender 404 is defined as a device used for mixing different gases for various purposes. By controlling volume of the different gases supplied to the gas blender 404, different compositions of gas mixtures can be obtained. In the present disclosure, by controlling the first and second flow control valves 406A, 406B, supply of air and oxygen to the gas blender 404 may be controlled to produce a desired composition of an oxygen-air mixture.

The system 400 further includes a humidifier 408 for humidifying the gas flow. The flow source 402 is in fluid communication with the humidifier 408 via the gas blender 404. Particularly, the humidifier 408 is fluidly communicated with the gas blender 404 to receive the oxygen-air mixture therefrom. The humidifier 408 is defined as a device that adds moisture to the gas flow. In the present disclosure, the humidifier 408 is used to add moisture to the oxygen-air mixture coming from the gas blender 404 to supply a desired quality of gas to the patient during the HFNC therapy. The humidifier 408 is further fluidly coupled to the differential pressure flow meter 100. According to the present disclosure, the differential pressure flow meter 100 includes a primary element, which is otherwise known as the fluid restriction unit 102, and a secondary element, which is otherwise known as the differential pressure transducer 104.

The fluid restriction unit 102 and the differential pressure transducer 104 are hereinafter alternatively referred to as the primary element and the secondary element, respectively. The primary element provides the pressure drop through the fluid conduit, while the secondary element is responsible for measuring the pressure drop generated by the primary element. The humidifier 408 is fluidly coupled to the upstream compartment 106 of the fluid restriction unit 102 of the differential pressure flow meter 100. The differential pressure flow meter 100 measures flow rate of the gas by generating a pressure drop in the fluid restriction unit 102. The differential pressure transducer 104 coupled across the orifice element 120 of the fluid restriction unit 102 converts mechanical power (the pressure drop) into electrical power (in terms of voltage). Particularly, the differential pressure flow meter 100 generates an electrical signal based on the pressure drop occurred across the orifice element 120 to communicate with the microcontroller 140.

The system 400 further includes an amplifier 410 for increasing the electrical signal strength generated by the differential pressure flow meter 100. The amplifier 410 is defined as an electronic device for increasing amplitude of electric signals. As such, the amplifier 410 of the present disclosure is used to increase strength of the electrical signal indicative of the pressure drop generated by the differential pressure flow meter 100. In some embodiments, the amplifier 410 may be communicated with the first sensor 142 and the second sensor 144 coupled to the high-pressure side diaphragm 136H and the low-pressure side diaphragm 136L, respectively, of the diaphragm compartment 136. As such, the electric signal indicative of the pressure drop generated by the first and second sensors 142, 144 may be communicated with the amplifier 410 to increase strength thereof. The electrical signal, otherwise known as voltage output, from the differential pressure transducer 104 is calibrated to give a fixed indication of differential pressure, which will be converted into a flow rate based on Bernoulli's equation.

The system 400 further includes a multimeter 412 for monitoring sensitivity of the first sensor 142 and the second sensor 144 of the differential pressure flow meter 100. The multimeter 412 is defined as an instrumentation device used for measuring electrical properties such as current, voltage and resistance of an electric circuit over several ranges of values. Sensitivity of a sensor may be defined by a ratio of the change of sensor signal to the change of actual value of interest. Further, the sensitivity of the sensor indicates how much the output of the sensor changes when the input quantity it measures changes.

The system 400 further includes the microcontroller 140 for controlling and monitoring the electrical signal generated by the differential pressure flow meter 100. Particularly, the microcontroller 140 is in communication with the amplifier 410 to control and monitor the electrical signal generated by the differential pressure flow meter 100. In some embodiments, the microcontroller 140 may be in communication with the multimeter 412, and the first and second sensors 142, 144 to determine sensitivity of the first and second sensors 142, 144. In some embodiments, the microcontroller 140 may also be in communication with the first flow control valve 406A and the second flow control valve 406B to control flow of air and oxygen, respectively, to the gas blender 404. In some embodiments, the microcontroller 140 may also be in communication with the humidifier 408 to control humidification of the gas flowing into the differential pressure flow meter 100. The system 400 further includes the computing device 146 configured to be in communication with the microcontroller 140. The computing device 146 is used for monitoring and regulating the humidified gas flow to the patients. The computing device 146 has the communications interface 148 such as keyboards, display monitor, and touch screen to input operating parameters to the system 400 during the HFNC therapy to the patients.

Figure 5:
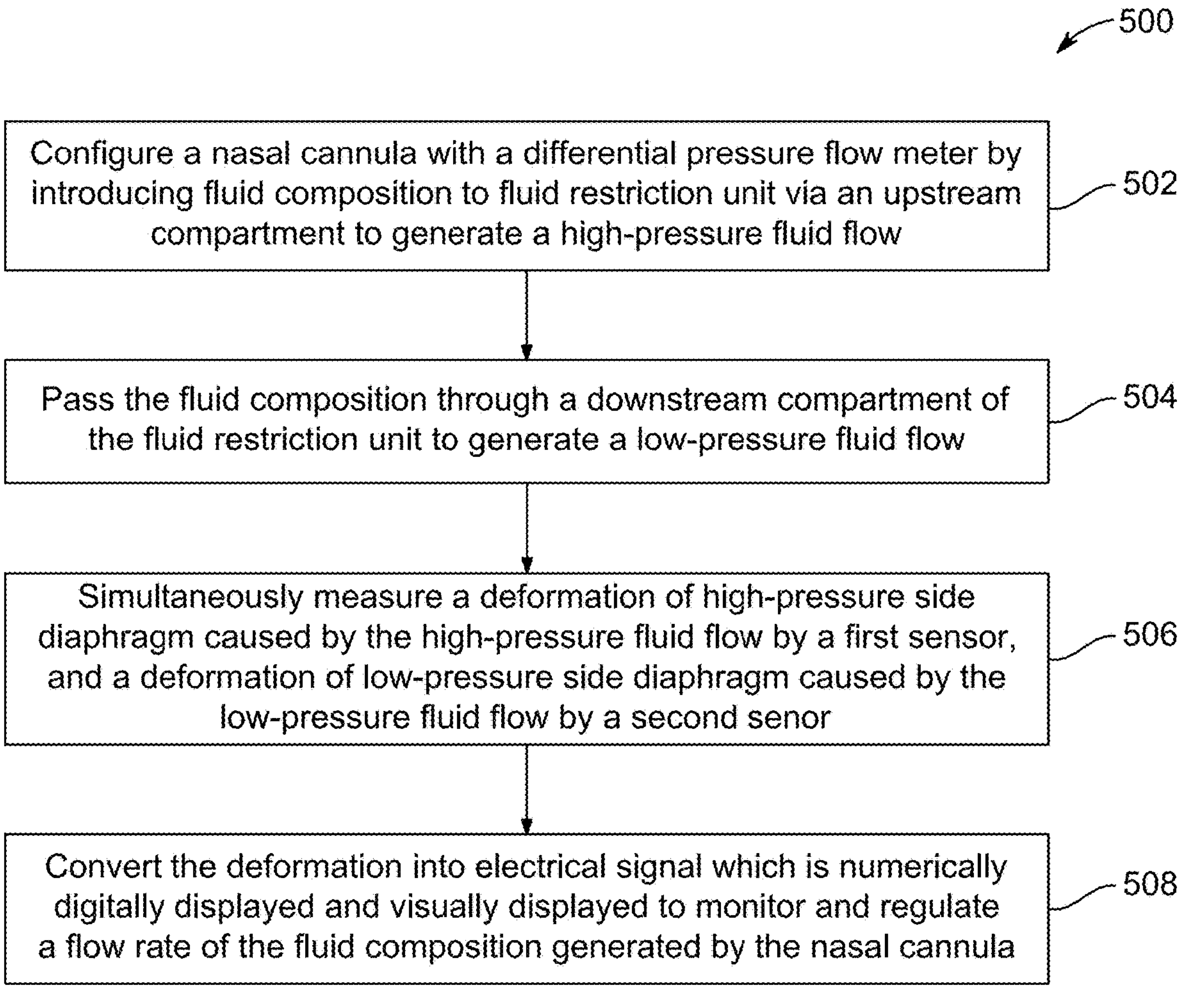
FIG. 5 is a schematic flow chart of a method of monitoring and regulating a flow rate of a fluid composition generated by a nasal cannula as determined by ASME MFC-3M, according to certain embodiments.

Referring to FIG. 5, a schematic flow chart of a method 500 of monitoring and regulating the flow rate of a fluid composition generated by the nasal cannula as determined by ASME MFC-3M [See: Measurement of Fluid Flow in Pipes Using Orifice, Nozzle, and Venturi, which is incorporated herein by reference in its entirety] is illustrated, according to an embodiment of the present disclosure. The order in which the method 500 described is not intended to be construed as a limitation, and any number of the described method steps can be combined in any order to implement the method 500. Additionally, individual steps may be removed or skipped from the method 500 without departing from the spirit and scope of the present disclosure. The method 500 of the present disclosure is illustrated with reference to the differential pressure flow meter 100 described in FIG. 1 through FIG. 3B and the system 400 described in FIG. 4.

At step 502, the method 500 includes configuring the nasal cannula with the differential pressure flow meter 100 by introducing the fluid composition to the fluid restriction unit 102 via the upstream compartment 106 to generate a high-pressure fluid flow. According to an implementation of the present disclosure, the differential pressure flow meter 100 is used in the HNFC therapy of the patients. The fluid restriction unit 102 of the differential pressure flow meter 100 is fluid tightly coupled to the nasal cannula. Particularly, the upstream compartment 106 of the fluid restriction unit 102 is fluid tightly coupled to the nasal cannula, which in turn coupled to the humidifier 408. The air and oxygen are supplied from the flow source 402 to the gas blender 404 to generate the fluid composition. The first flow control valve 406A and the second flow control valve 406B may be operated to control the flow of the air and the oxygen, respectively, from the flow source 402 to the gas blender 404. The fluid composition is further communicated with the humidifier 408 to add moisture to generate the fluid composition of desired quality to supply to the patients. In some embodiments, the fluid composition includes air, oxygen, and the moisture. The fluid composition flowing through the upstream compartment 106 of the fluid restriction unit 102 is at a high pressure compared to a pressure of the fluid composition at any other location in the fluid restriction unit 102, hence the flow of the fluid composition through the upstream compartment 106 may be alternatively referred to as ‘the high-pressure fluid flow’. The high-pressure fluid flow is in communication with the differential pressure transducer 104 via the first fluid outlet port 110. Particularly, the high-pressure fluid flow is in communication with the high-pressure compartment 132 of the chamber 130 of the differential pressure transducer 104. The high pressure of the fluid composition may apply a force on the diaphragm 138 of the diaphragm compartment 136 thereby the high-pressure side diaphragm 136H of the diaphragm 138 deforms from an original position thereof.

At step 504, the method 500 includes passing the fluid composition through the downstream compartment 108 of the fluid restriction unit 102 to generate a low-pressure fluid flow. The fluid composition entering the upstream compartment 106 passes through the centric bore 122 of the orifice element 120. As the orifice element 120 imposes a restriction to the flow of the fluid composition while allowing the flow of the fluid composition through the centric bore 122 and into the downstream compartment 108, a pressure of the fluid composition decreases in the downstream compartment 108. Therefore, the flow of the fluid composition through the downstream compartment is alternatively referred to as ‘the low-pressure fluid flow’. The low-pressure fluid flow is in communication with the differential pressure transducer 104 via the second fluid outlet port 112. Particularly, the low-pressure fluid flow is in communication with the low-pressure compartment 134 of the chamber 130 of the differential pressure transducer 104. The low pressure of the fluid composition may apply a force on the diaphragm 138 of the diaphragm compartment 136 thereby the low-pressure side diaphragm 136L of the diaphragm 138 deforms from the original position thereof.

At step 506, the method 500 includes simultaneously measuring the deformation of the high-pressure side diaphragm 136H caused by the high-pressure fluid flow by the first sensor 142, and the deformation of the low-pressure side diaphragm 136L caused by the low-pressure fluid flow by the second senor 144. The first sensor 142 attached to the high-pressure side diaphragm 136H of the diaphragm 138 and the second sensor 144 attached to the low-pressure side diaphragm 136L of the diaphragm 138 generates the electrical signal indicative of the pressure drop generated across the orifice element 120 in the fluid restriction unit 102. The multimeter 412 connected to the first sensor 142 and the second sensor 144 determines the sensitivity of the first and second sensors 142, 144.

At step 508, the method 500 includes converting the deformation into the electrical signal which is numerically digitally displayed and visually displayed to monitor and regulate the flow rate of the fluid composition generated by the nasal cannula. The deformation of the diaphragm 138 by the pressure drop in the fluid restriction unit 102 is captured by the first and second sensors 142, 144 and generate the electrical signal corresponding to the pressure drop. The electrical signal is further communicated with the amplifier 410 to increase the strength thereof. The electrical signal is further communicated to the microcontroller 140 to monitor and regulate the flow rate of the fluid composition during the HNFC therapy. The microcontroller 140 is further communicated with the computing device 146 such that the flow rate of the fluid composition measured by the differential pressure flow meter 100 is digitally and visually displayed in a monitor of the computing device 146. In some embodiments, the flow rate of the fluid composition is in a range of 0.5 to 20 liters per minute (L/min), preferably 1 to 10 L/min, preferably 2 to 8 L/min, or even more preferably 4 to 6 L/min. Other ranges are also possible. In some embodiments, the flow rate of the fluid composition is in a range of 5 to 100 L/min, preferably 10 to 80 L/min, preferably 20 to 60 L/min, or even more preferably 30 to 40 L/min. Other ranges are also possible. In some embodiments, the method 500 has less than 30% error based on the flow rate of the fluid composition, preferably less than 25%, preferably less than 20%, or even more preferably less than 10%. Other ranges are also possible. The user may use the communications interface 148 of the computing device 146 to input operating parameters to regulate the flow rate of the fluid composition for the effective HNFC therapy of the patients.

EXAMPLES

The disclosure will now be illustrated with working examples, which are intended to illustrate the working of disclosure and not intended to restrictively imply any limitations on the scope of the present disclosure. The working examples depict a design of a restriction unit and experimental set up of the modified orifice restriction unit of the present disclosure.

Example 1: Design Selection

According to the present disclosure, four different types of differential pressure flow meters such as a basic orifice, a modified orifice, a venturi, and a modified venturi or nozzle were tested. These designs were developed based on the three existing designs such as the orifice, the venturi, and the nozzle, which are primarily used in most of the applications. The four different restriction units were stimulated using center of flow simulation (CFS) program to specify the inner diameter 'd' of the centric bore 122 of the orifice element 120. Engineering standard ISO-5167 for Orifice sizing was followed, which states that the acceptable orifice beta ratio for gases should be between 0.2 and 0.7 [See: A. Tomaszewski, T. Przybylinski and M. Lackowski, "Experimental and Numerical Analysis of Multi-Hole Orifice Flow Meter: Investigation of the Relationship between Pressure Drop and Mass Flow Rate", Sensors, vol. 20, no. 24, p. 7281, 2020, which is incorporated herein by reference in its entirety]. Beta ratio is defined as a ratio between the inner diameter 'd' to an outer diameter of the orifice element 120. The output pressure was measured further and converted into flow in all the four models to provide the highest sensitivity with lowest possible error.

Figure 6A:
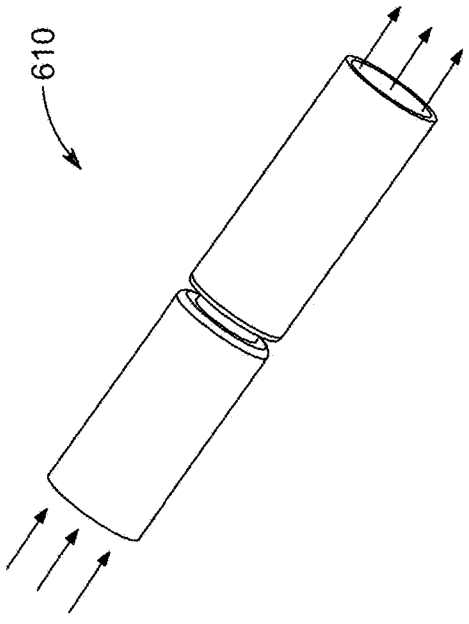
FIG. 6A is schematic perspective view of a basic orifice restriction unit, according to certain embodiments.

As shown in FIG. 6A, a basic orifice restriction unit 610 is shown, which is generally used in the HFNC therapy. The basic orifice restriction unit 610 is a simple design with sharp edges. The basic orifice restriction unit 610 provides high pressure drop due to its sharp edges, and the sharp restriction causes the flow to change its direction sharply, which produces turbulence. The turbulence is not desirable in the design of the present disclosure, as it can cause less accurate pressure drops, thus, less accurate flow rate results.

Figure 6B:
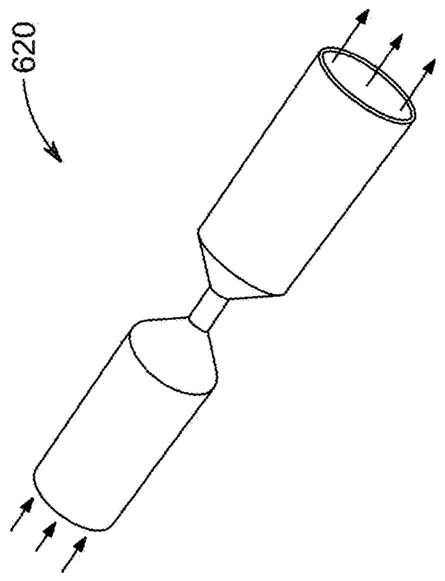
FIG. 6B is schematic perspective view of a venturi restriction unit, according to certain embodiments.

As shown in FIG. 6B, a venturi restriction unit 620 is shown, which is used in many applications because of stable structure thereof. Like the basic orifice restriction unit 610, the venturi restriction unit 620 is a simple design with sharp edges, but has more length to the restriction that is adjusted based on the design's specifications. The venturi restriction unit 620 provides more uniform flow than the basic orifice restriction unit 610 does, due to the shape thereof. The output flow of the venturi restriction unit 620 is less effected by the turbulence effect due to the shape thereof, and provides more space for the fluid to flow without changing its direction.

Figure 6C:
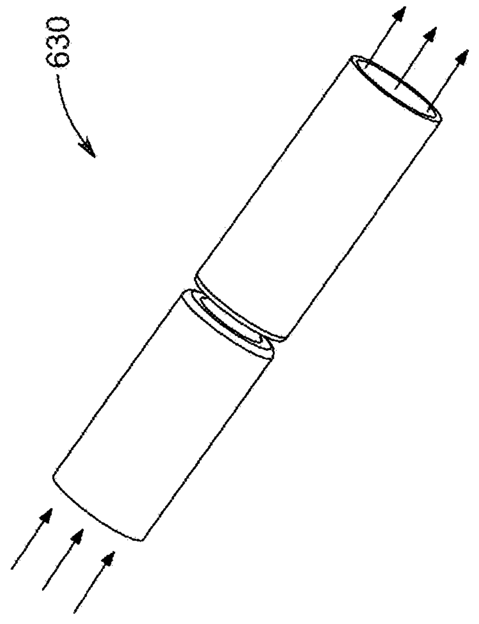
FIG. 6C is schematic perspective view of a modified orifice restriction unit, according to certain embodiments.

As shown in FIG. 6C, a modified orifice restriction unit 630 is shown based on the nozzle flow meter. Generally, nozzle flow meters have round edges, causing it to have more uniform flow direction. The orifice restriction is short, thus, it forces the flow to have high pressure drops. Moreover, the round corners lead the flow to behave in a more uniform manner, causing it to have less turbulence.

Figure 6D:
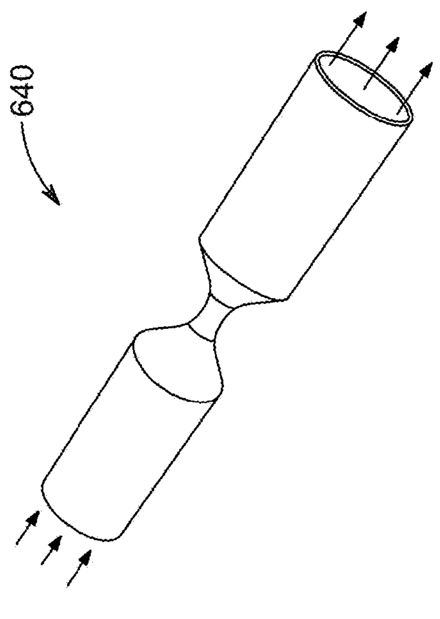
FIG. 6D is schematic perspective view of a modified venturi restriction unit, according to certain embodiments.

As shown in FIG. 6D, a modified venturi restriction unit 640 is shown based on the nozzle flow meter. The venturi restriction is longer than the orifice restriction, causing it to have more uniform flow and less turbulent. Moreover, round corners cause more stability to flow, as it helps to behave in a more uniform manner, and have the least turbulent among the four designs explained in FIG. 6A through FIG. 6D.

Example 2: Design Dimensions and Specifications

Figure 7A:
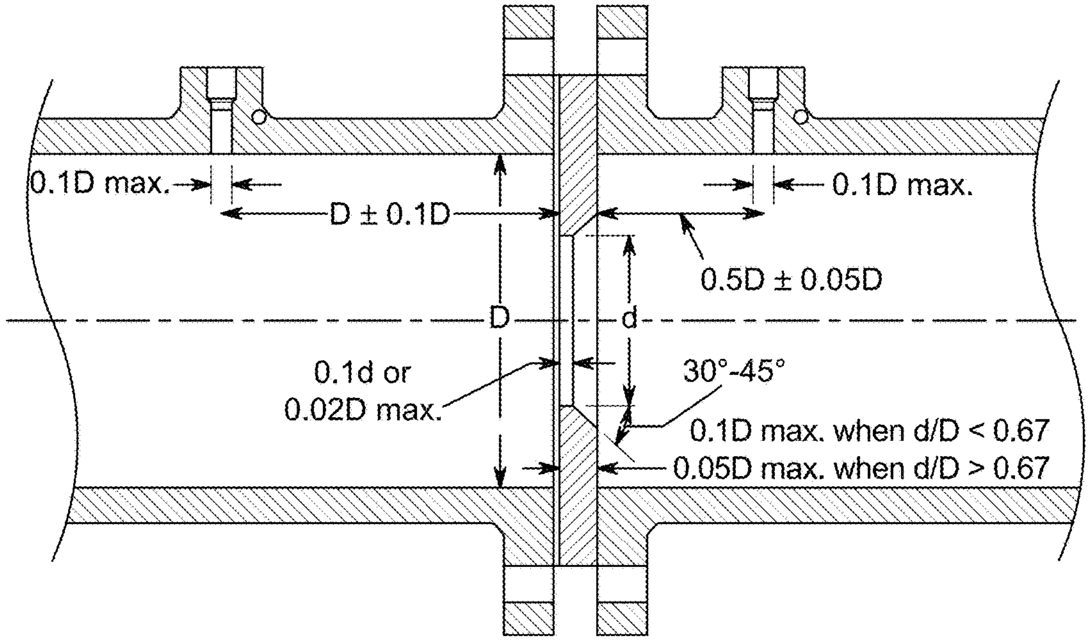
FIG. 7A illustrates dimensional specification of an orifice restriction unit, according to certain embodiments.

The basic orifice restriction unit 610 and the modified orifice restriction unit 630 have similar shapes and functionality, and thus have similar design specifications, particularly the dimensions. According to standard BS 1042.1, and referring to FIG. 7A, the specifications for designing an orifice restriction can be stated as the following [See: Measurements of fluid flow in closed conduits. BS 1024-1.2. 1989; and W. Boyes, Instrumentation reference book, 4th ed. Burlington: Butterworth-Heinemann/Elsevier, 2010, pp. 37-38, each of which is incorporated herein by reference in their entireties]:

The diameter of the throat should be between 0.224D-0.742D, where 'D' is the diameter of the tube.
The length of the throat should not exceed 1.0d or 0.02D.
The cylindrical entrance section should have the diameter 'D' and a length greater than 1.0d.
The divergent section length should have a length less than 1.5d.

Figure 7B:
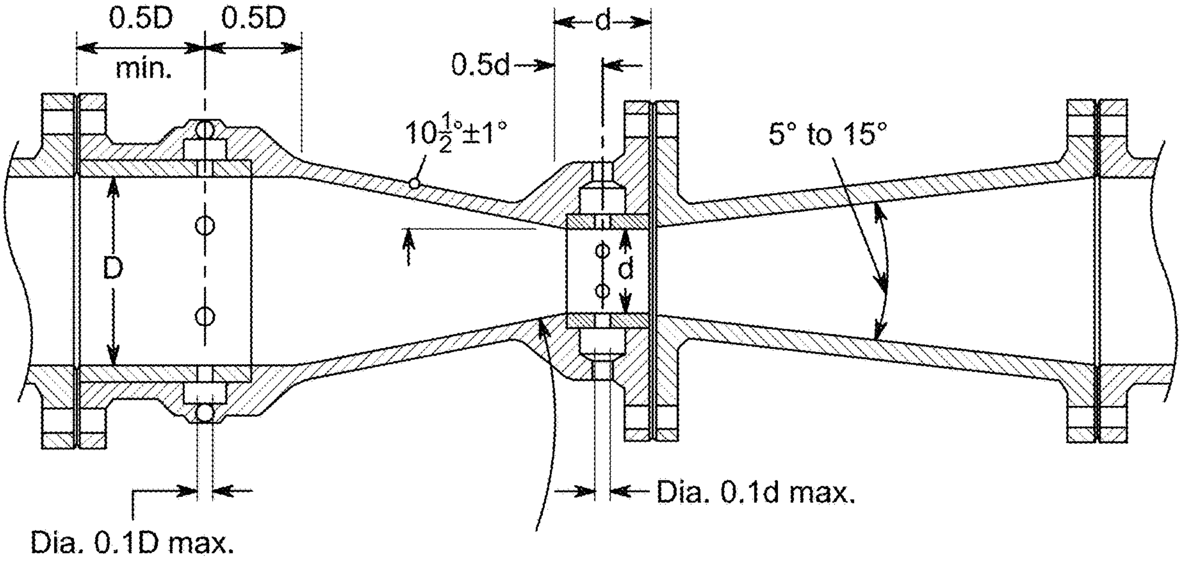
FIG. 7B illustrates dimensional specification of a venturi restriction unit, according to certain embodiments.

Similar to the basic orifice and the modified orifice restriction units 610, 630, both the venturi and the modified venturi restriction units 620, 640 have similar shapes and functionality, as illustrated in FIG. 7B. According to standard BS 1042.1, the specifications for designing a venturi restriction can be stated as the following:

The diameter of the throat should be between 0.224D-0.742D, where 'D' is the diameter of the tube.
The length of the throat should be equal to 1.0d.
The cylindrical entrance section should have the diameter 'D' and a length greater than 1.0d.
The divergent section length should have a length less than 1.5d.

Example 3: Measuring Locations

Figure 8A:
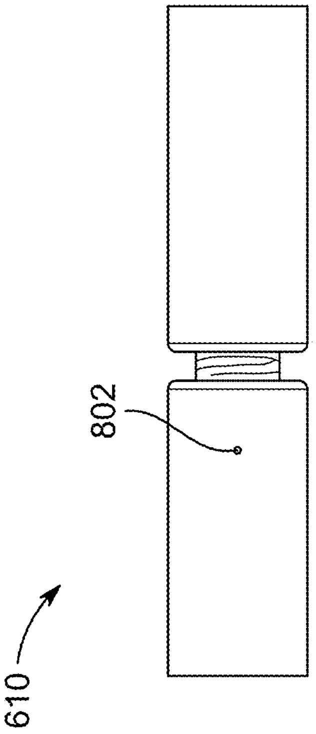
FIG. 8A illustrates a measuring location of an inlet pressure of the basic orifice restriction unit, according to certain embodiments.
Figure 8B:
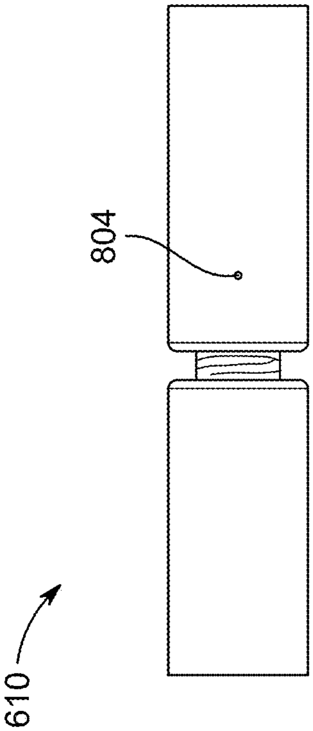
FIG. 8B illustrates a measuring location of an outlet pressure of the basic orifice restriction unit, according to certain embodiments.
Figure 8C:
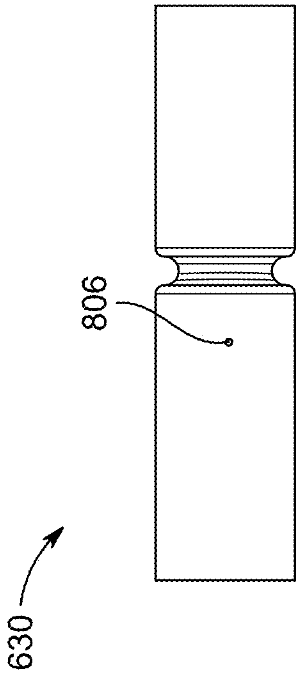
FIG. 8C illustrates a measuring location of an inlet pressure of the modified orifice restriction unit, according to certain embodiments.
Figure 8D:
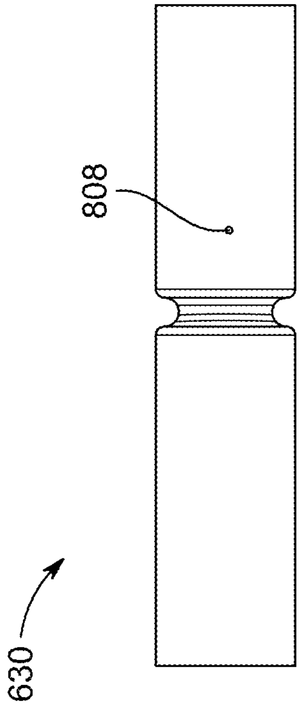
FIG. 8D illustrates a measuring location of an outlet pressure of the modified orifice restriction unit, according to certain embodiments.

The pressure measurements were taken based on the specifications of the orifice and the venturi designs. The pressure drop values of the orifice and the modified orifice restriction units 610, 630 were taken from two points, an inlet and an outlet of each of the basic orifice restriction unit 610 and the modified orifice restriction unit 630. The pressure measurements of the basic orifice restriction unit 610 is shown by an inlet pressure 802 (shown in FIG. 8A) and an outlet pressure 804 (shown in FIG. 8B). Similarly, the pressure measurements of the modified orifice restriction unit 630 is shown by an inlet pressure 806 (shown in FIG. 8C) and an outlet pressure 808 (shown in FIG. 8D).

Figure 9A:
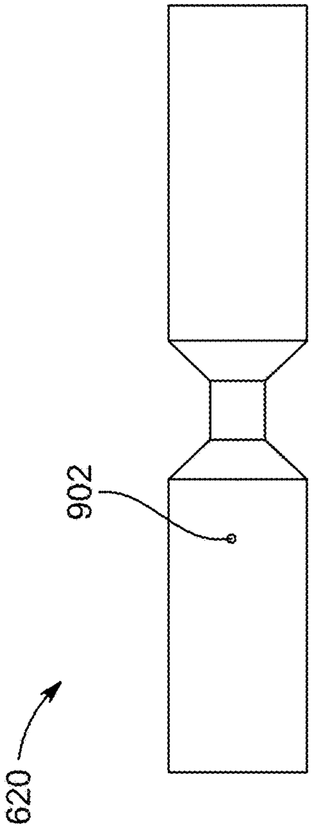
FIG. 9A illustrates a measuring location of an inlet pressure of the venturi restriction unit, according to certain embodiments.
Figure 9B:
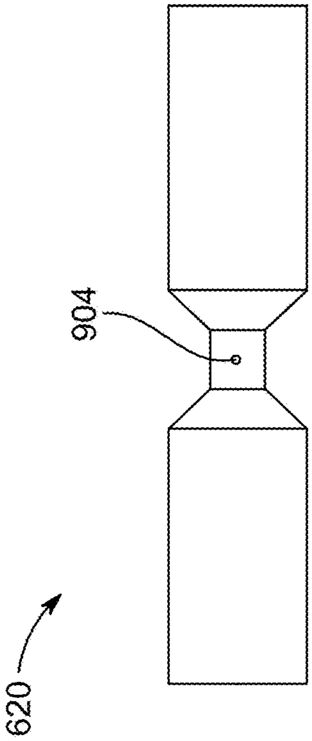
FIG. 9B illustrates a measuring location of an outlet pressure of the venturi restriction unit, according to certain embodiments.
Figure 9C:
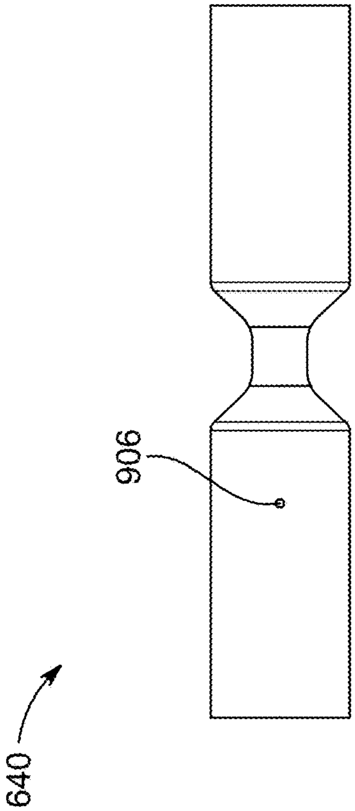
FIG. 9C illustrates a measuring location of an inlet pressure of the modified venturi restriction unit, according to certain embodiments.
Figure 9D:
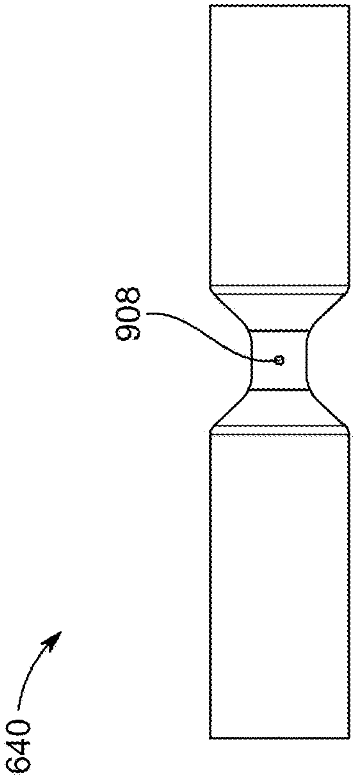
FIG. 9D illustrates a measuring location of an outlet pressure of the modified venturi restriction unit, according to certain embodiments.

The pressure measurements of the venturi and the modified venturi restriction units 620, 640 were measured from different locations based on the venturi specifications. Inlet pressure location was in the same location as in the basic orifice and the modified orifice restriction units 610, 630, however, outlet pressure measurements were taken from a center of venturi restriction instead of an end thereof. The pressure measurements of the venturi restriction unit 620 are shown by an inlet pressure 902 (shown in FIG. 9A) and an outlet pressure 904 (shown in FIG. 9B). Similarly, the pressure measurements of the modified venturi restriction unit 640 is shown by an inlet pressure 906 (shown in FIG. 9C) and an outlet pressure 908 (shown in FIG. 9D).

Figure 10A:
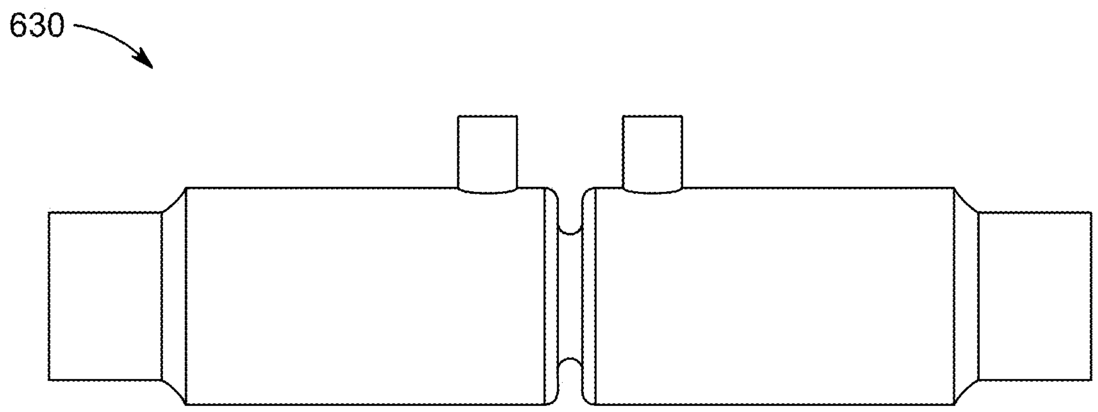
FIG. 10A is a side view of a three-dimensional (3D) design model of the modified orifice restriction unit, according to certain embodiments.
Figure 10B:
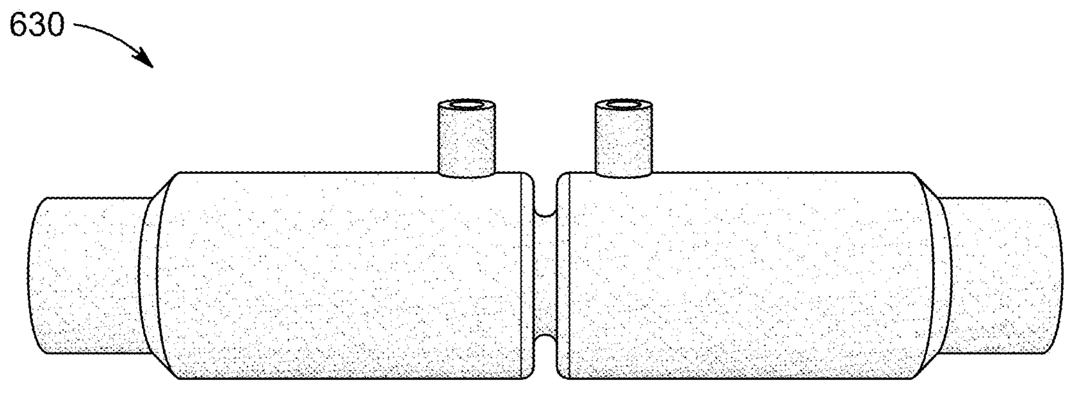
FIG. 10B is a side view of a 3D printed model of the modified orifice restriction unit of FIG. 10A, according to certain embodiments.

After testing all the four restriction units, the modified orifice restriction unit 630 with 5 mm inner diameter was identified as the desired design model, according to the present disclosure. A three-dimensional (3D) design model of the modified orifice restriction unit 630 was developed using an AutoCAD application, as shown in FIG. 10A. The smooth edges in both sides of the modified orifice restriction unit 630 were added to fit the modified orifice restriction unit 630 easily with the nasal cannula. After the 3D model of the modified orifice restriction unit 630 is ready, it was sent to a 3D printing lab to be printed using Nylon material. The final result of the printed modified orifice restriction unit is shown in FIG. 10B. The construction and the dimensional specifications of the modified orifice restriction unit 630 is same as the fluid restriction unit 102 described in FIG. 1 through FIG. 3B. After printing the modified orifice restriction unit 630, it was tested using a pressure sensor to check whether the results match the simulated design or not.

As illustrated in FIG. 10B, the modified orifice restriction unit was printed by a 3D printing technique using Nylon material. In general, Nylon material has wide range of applications as it has good thermal and mechanical properties to handle the high temperature and the high flow rate generated by the HFNC. Further, Nylon has very good wear resistance, combined with high modulus of elasticity and tensile strength, which makes it ideal to handle the high flow of gases. Moreover, it has a large heat distortion temperature, and it can resist vibration, abrasion, and wear. Also, Nylon is light weight, that is only half weight of aluminum, ⅛ weight of bronze, and ⅐ the weight of iron. Additionally, it has a very high melting point up to 258° C., which helps to handle the high temperature coming out from the HFNC specially when it is used for patients in the IC unit for a long period of time. The high heat handling property along with other good mechanical properties guarantee that the modified orifice restriction unit 630 will not be expanded with time. Also, its light weight reduces the inertial and static loads for patient treated by HFNC, where the modified orifice flowmeter is only 8 g weight compared to 29 g stainless steel orifice with the same dimensions.

Materials used in oxygen piping systems have to be compatible with oxygen at the same specific temperature and pressure used in the system. Non-compatible materials with oxygen are highly hazardous and might lead to firing issues and affect the health and safety of the patient. Since the Nylon will be exposed to the oxygen, it must be compatible with it. The Nylon material is very effective and compatible when using it in the physiological chamber construction. They tested the Nylon for its efficiency as devices utilized to measure the oxygen uptake [See: E. Stevens, "Use of plastic materials in oxygen-measuring systems", Journal of Applied Physiology, vol. 72, no. 2, pp. 801-804, 1992, each of which is incorporated herein by reference in its entirety]. Furthermore, nylon has biocompatibility nature, which indicates it has a tunable mechanical features and desirable chemical stability, so it is widely used in medical applications such as dentures, catheters, and sutures.

In some embodiments, the output was tested using a MPX10DP pressure sensor, which is a differential pressure sensor of silicon piezoresistive type that gives a precise and linear voltage output, and it is directly proportional to the pressure exerted on it. It has a silicon shear stress strain gauge design, and uncompensated temperature features to allow a user to add own temperature compensation. MPX10DP can measure pressure range between 0-10 KPa (0 to 1.45 psi) with low sensitivity around 3.5 mV/kPa, and 35 mV Full Scale Span [See: MPX10DP spec datasheet of Freescale Semiconductor which can be found via https://pdfl.alldatasheet.com/datasheet-pdf/view/246184/FREESCALE/MPX10DP.html and is incorporated herein by reference in its entirety].

Figure 11:
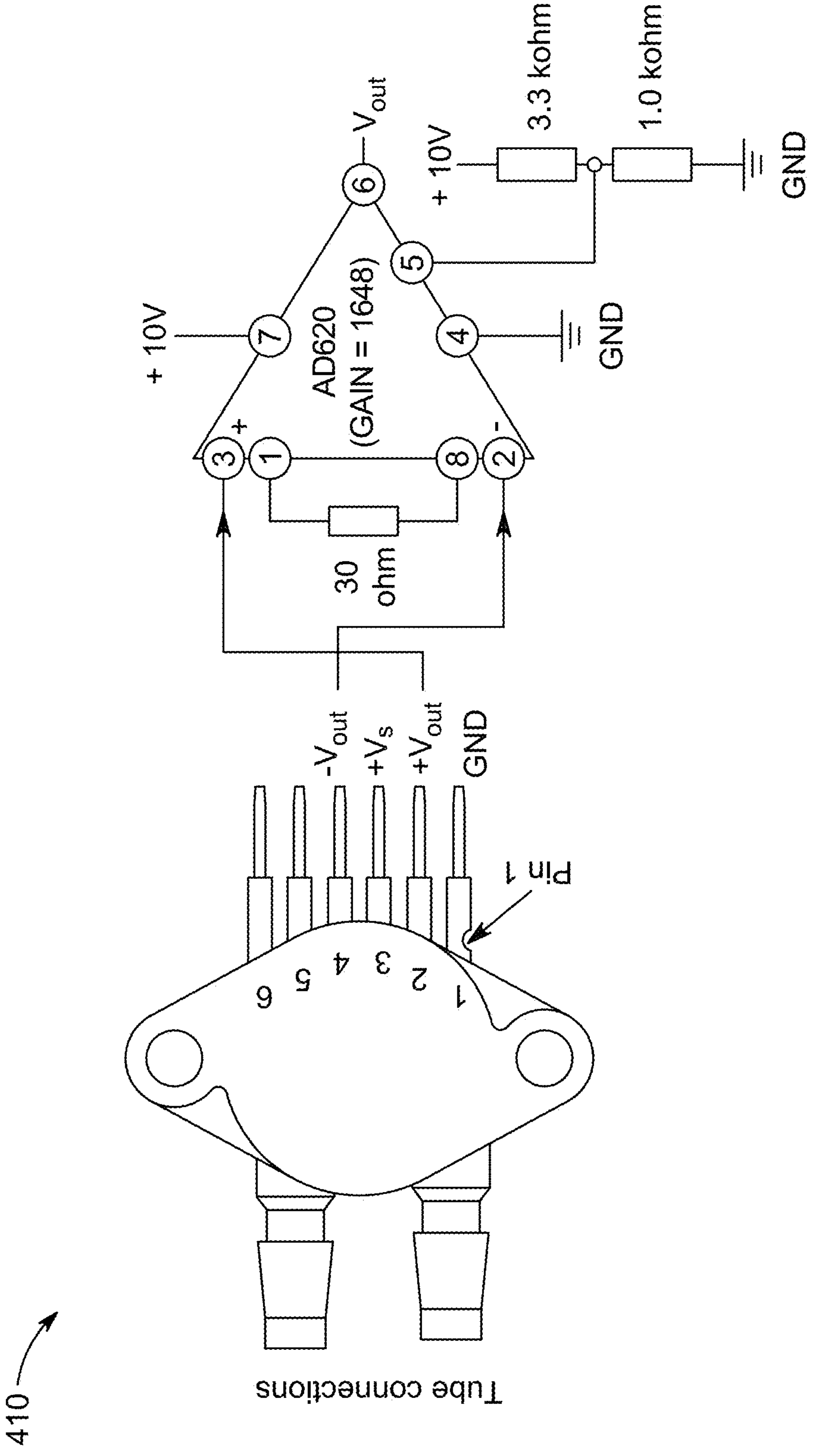
FIG. 11 is a schematic circuit diagram of an amplifier associated with the modified orifice restriction unit, according to certain embodiments.

As described in FIG. 4, the microcontroller 140, such as Arduino, was used to detect the output pressure from the pressure sensor, however, the pressure sensor has a very small output voltage in milli volt, so it is used with the amplifier 410, shown in FIG. 11. In an example, AD620 instrumentation amplifier was used as it has a low cost and high accuracy, where it needs only one external resistor to set gains of 1 to 10,000. Also, the AD620 instrumentation amplifier has a small size that makes it a good fit for portable or remote applications, such as the flow meter in the present disclosure. Moreover, the AD620's low power, low input bias current, and low noise makes it suitable for medical products and applications. According to the datasheet of the amplifier, the gain resistor was set to be 30Ω, so the total gain was set to 1648. Using the following equation [See: AD620 Datasheet of Analog Devices, which can be found via https://pdfl.alldatasheet.com/datasheet-pdf/view/48090/AD/AD620.html and is incorporated herein by reference in its entirety]:

$$R_G = \frac{49.4\,k\Omega}{G-1} \tag{1}$$

After the signal detection, converting the signal into pressure and then into flow using the microcontroller 140, particularly the Arduino code. The output flow was displayed in the computing device 146. In an example, the output flow was displayed in I2C liquid crystal display (LCD).

Example 4: Differential Pressure Transducer Prototype

Figure 12:
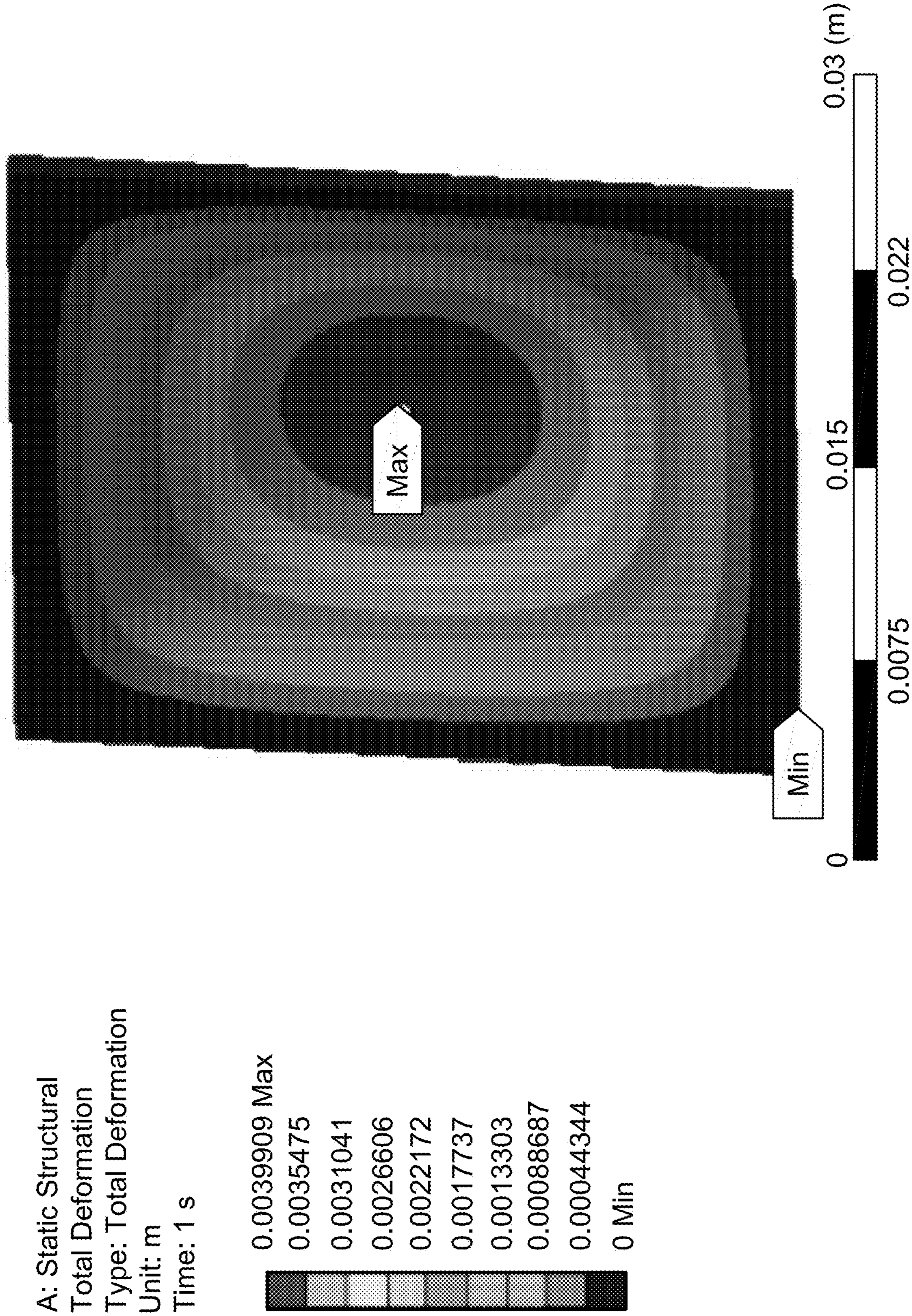
FIG. 12 illustrates simulation of a diaphragm of a differential pressure transducer of the differential pressure flow meter of FIG. 1, according to certain embodiments.

According to the present disclosure, the flow sensor, otherwise referred to as the differential pressure flow meter 100, composed of the fluid restriction unit 102 and the differential pressure transducer 104. Development of the differential pressure transducer 104 is illustrated hereinbelow. As shown in FIG. 12, simulation of the diaphragm 138 of the diaphragm compartment 136 using Ansys simulation software is performed to determine the best dimension that will give the higher diaphragm deflection, thus having the higher accuracy. The deformation behavior was tested for three squared diaphragms of the same material, Rubber, but with different dimensions. The tested sizes were 30*30 mm, 20*20 mm, and 10*10 mm. Table 1 shows the total deformation of the diaphragms when the pressure at specific flows was applied on them. As seen in the Table 1, the diaphragm of size 30*30 mm has the highest deformation rate, so it was applied in the present disclosure.

TABLE 1

| Total deformation of the diaphragms | | | | |
|---|---|---|---|---|
| Flow rate | Pressure | Total Deformation (mm) | | |
| (L/min) | Difference (Pa) | L = 30 mm | L = 20 mm | L = 15 mm |
| 10 | 7.529 Pa | 0.6453 mm | 0.00015667 mm | 0.000050578 mm |
| 20 | 32.438 Pa | 1.5118 mm | 0.0005919 mm | 0.0002167 mm |
| 30 | 76.473 Pa | 2.2156 mm | 1.0727 mm | 0.00047795 mm |
| 40 | 140.892 Pa | 2.8364 mm | 1.5033 mm | 0.00078125 mm |
| 50 | 225.734 Pa | 3.423 mm | 1.8975 mm | 1.0779 mm |
| 60 | 330.308 Pa | 3.9909 mm | 2.2605 mm | 1.3556 mm |
| Average | 135.56 Pa | 2.4889 mm | 1.4737 mm | 0.75938 mm |

Figure 13A:
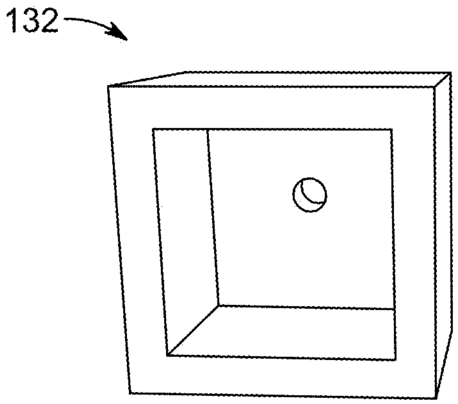
FIG. 13A is a perspective view of a 3D design model of a high-pressure compartment of a chamber of the differential pressure transducer, according to certain embodiments.
Figure 13B:
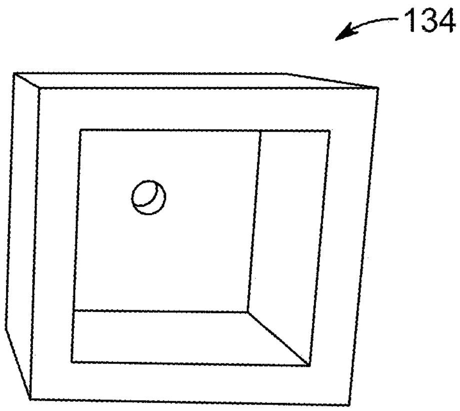
FIG. 13B is a perspective view of a 3D design model of a low-pressure compartment of the chamber of the differential pressure transducer, according to certain embodiments.
Figure 13C:
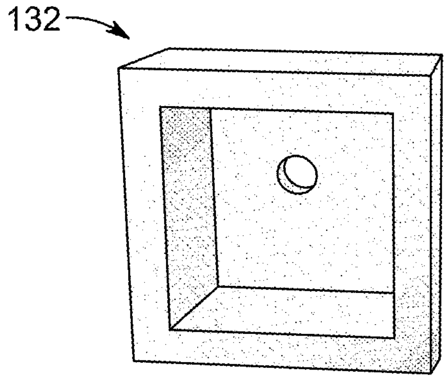
FIG. 13C is a perspective view of a 3D printed model of the high-pressure compartment of FIG. 13A, according to certain embodiments.
Figure 13D:
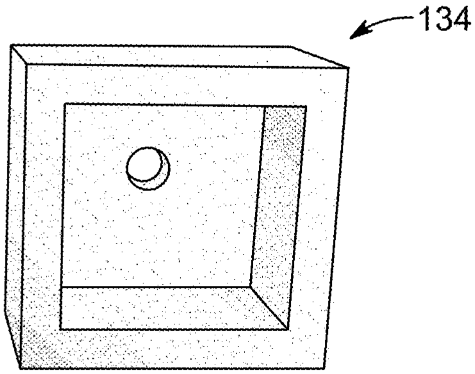
FIG. 13D is a perspective view of a 3D printed model of the low-pressure compartment of FIG. 13B, according to certain embodiments.

Further, the chamber 130 having the high-pressure compartment 132 and the low-pressure compartment 134 was designed with the same dimensions of the diaphragm 138 using the AutoCAD software application, as shown in FIG. 13A and FIG. 13B, respectively. The high-pressure compartment 132 and the low-pressure compartment 134 of the chamber 130 were 3D printed, as shown in FIG. 13C and FIG. 13D, respectively.

Figure 14A:
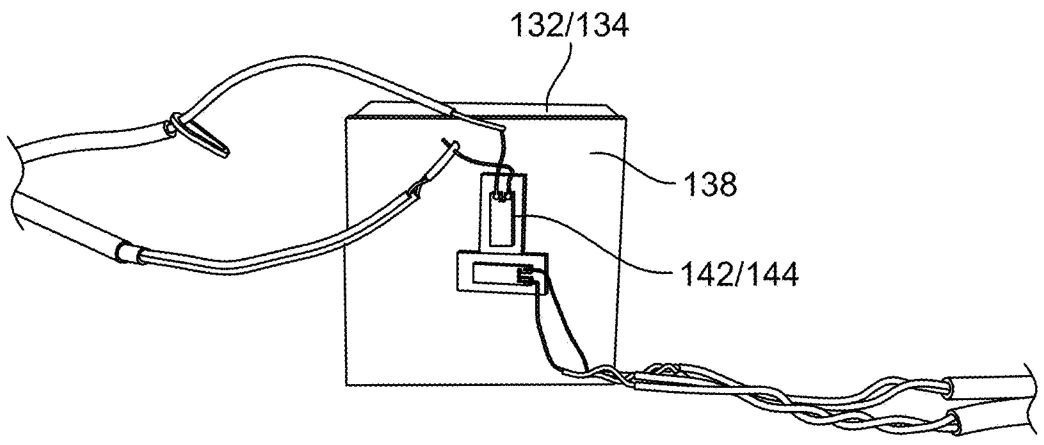
FIG. 14A is a perspective view of a prototype of the differential pressure transducer showing a strain gauge sensor attached with the diaphragm, according to certain embodiments.
Figure 14B:
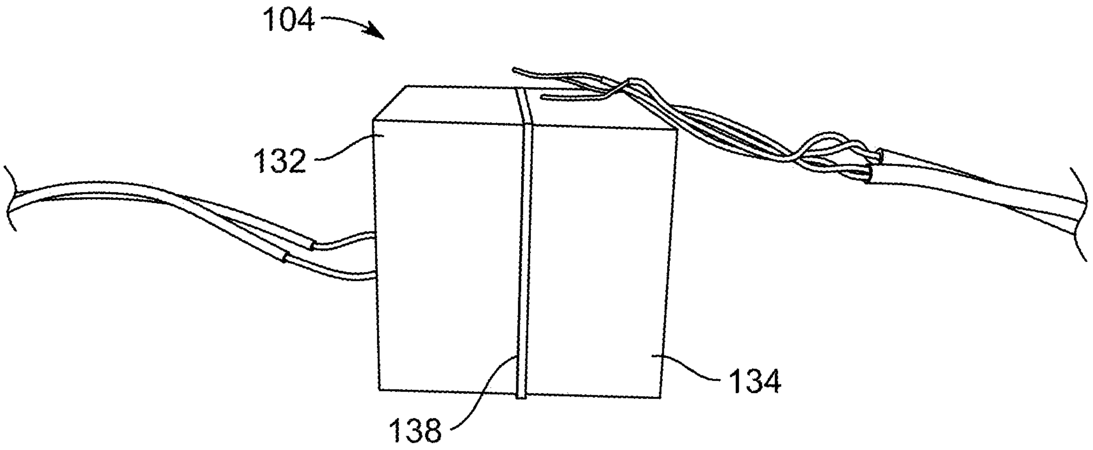
FIG. 14B is a perspective view of a prototype of the differential pressure transducer, according to certain embodiments.

The chamber 130 includes the high-pressure compartment 132 and the low-pressure compartment 134 of the same dimensions, where the diaphragm 138 is made of silicon rubber. The diaphragm 138 is further attached with the strain gauge sensor and was placed in one of the high-pressure or the low-pressure compartments 132, 134 of the chamber 130 as shown in FIG. 14A. Further, the low-pressure and the high-pressure compartments 132, 134 were tightly placed over each other to avoid air leakage while taking the results. An assembled view of the prototype of the differential pressure transducer 104 is shown in FIG. 14B.

Example 5: Numerical Modeling

To calculate the flow rate of the gas depending on the measured pressure drop generated by the orifice restriction, Bernoulli and continuity equations were combined to calculate the flow rate when the dimensions of the fluid restriction unit having the orifice element and the density of the gas is known according to the handbook of hydraulic resistance [See: I. Idelbchik, Handbook of hydraulic resistance. New York, N.Y.: Hemisphere, 1986, which is incorporated herein by reference in its entirety]:

$$Q = \frac{A_0}{\sqrt{1-\beta^4}} \times \sqrt{\frac{2\Delta P}{\rho}} \left(\frac{\mathrm{m}^3}{\mathrm{s}}\right) \tag{2}$$

In fact, mass flow rate $Q_m$ equation was also used in the numerical modeling calculation where:

$$Q_m = \frac{A_0}{\sqrt{1-\beta^4}} \times \sqrt{2\Delta P\rho} \left(\frac{\mathrm{Kg}}{\mathrm{sec}}\right) \tag{3}$$

Where ρ is the density of the gas, $A_0$ is the orifice cross sectional area, and is Beta Ratio and they can be calculated using the following equations:

$$A_0 = \frac{\pi}{4} d^2 (m^2) \tag{4}$$

-continued $$\beta = \frac{\text{Orifice diameter}}{\text{Pipe diameter}} = \frac{d}{D} \tag{5}$$

Nevertheless, equation (1) is applicable only for incompressible, frictionless fluid of laminar flow type. In real world, ideal fluids do not exist, so some edits must be added to equation (1) to get accurate flow calculations. This approach can be presented according to ISO standard [See: A. Tomaszewski, T. Przybylinski and M. Lackowski, "Experimental and Numerical Analysis of Multi-Hole Orifice Flow Meter: Investigation of the Relationship between Pressure Drop and Mass Flow Rate", Sensors, vol. 20, no. 24, p. 7281, 2020, which is incorporated herein by reference in its entirety] where the flow rate equation for the flow estimation has the following form, with the addition of the flow coefficient and expansion number:

$$Q = \frac{CA_0}{\sqrt{1-\beta^4}} \times \sqrt{\frac{2\Delta P}{\rho}} \left(\frac{\mathrm{m}^3}{\mathrm{s}}\right) \tag{6}$$

Here, the flow coefficient and the expansion number are respectively [See: Reader-Harris, M. J.; Sattary, J. A. The orifice plate discharge coefficient equation—The equation for ISO5167-1. In Proceedings of the 14th North Sea Flow Measurement Workshop, Peebles, UK, 25-28 Oct. 1996; National Engineering Laboratory: East Kilbride, Glasgow, U K, 1996; p. 24; Reader-Harris, M. J. The equation for the expansibility factor for orifice plates. In Proceedings of the FLOMEKO 98, Lund, Sweden, 15-17 Jun. 1998; pp. 209-214, each of which is incorporated herein by reference in their entireties]:

$$C = 0.5961 + 0.0261\beta^2 - 0.216\beta^8 + 0.000521\left(\frac{10^6\beta}{\mathrm{Re}}\right)^{0.7} + \left(0.0188 + 0.0063\left(\frac{19000\beta}{\mathrm{Re}}\right)^{0.8}\right)\beta^{3.5}\left(\frac{10^6}{\mathrm{Re}}\right)^{0.3} \tag{7}$$

$$\varepsilon = 1 - \left(0.351 + 0.256\beta^4 + 0.93\beta^8\right)\left[1 - \left(\frac{p2}{p1}\right)^{\frac{1}{k}}\right]. \tag{8}$$

However, equations 6, 7 and 8 were not developed for the rounded corner orifice flow meter with the dimensions specified in the present disclosure. The differential pressure and flow rate were calculated and the error between the measured and calculated results was recorded in the result section described herein below.

Example 6: Experimental Setup

The experimental assessment of the previous modified orifice plate has been carried out to: (i) compare the experimental results with the simulated results, and (ii) assess the modified orifice effectivity under the humidified gas coming from the heated humidifier device.

Figure 15:
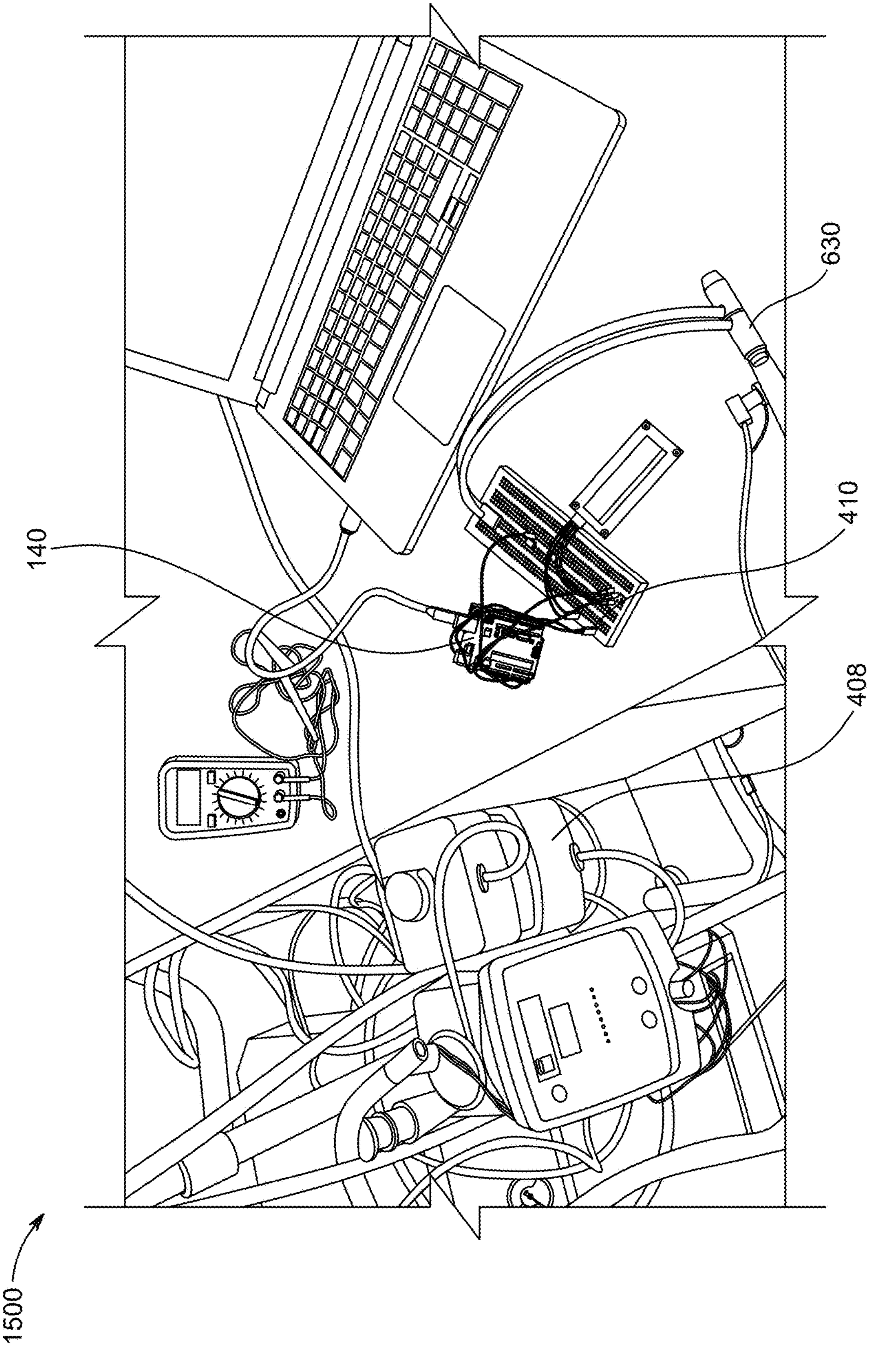
FIG. 15 illustrates an experimental set up of the modified orifice restriction unit, according to certain embodiments.
Figure 16:
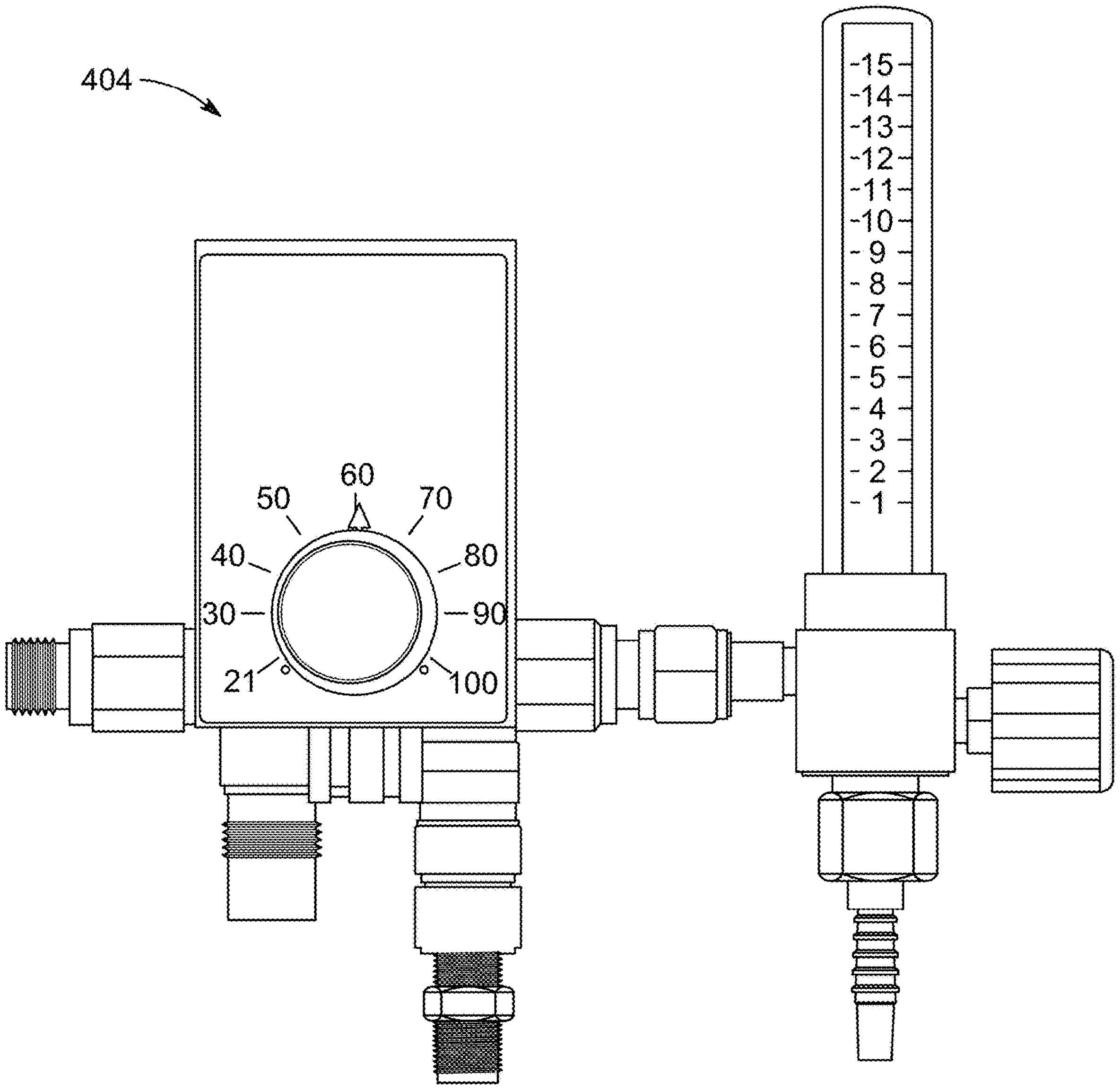
FIG. 16 is a schematic diagram of a gas blender used in the experimental set up of FIG. 15, according to certain embodiments.
Figure 17:
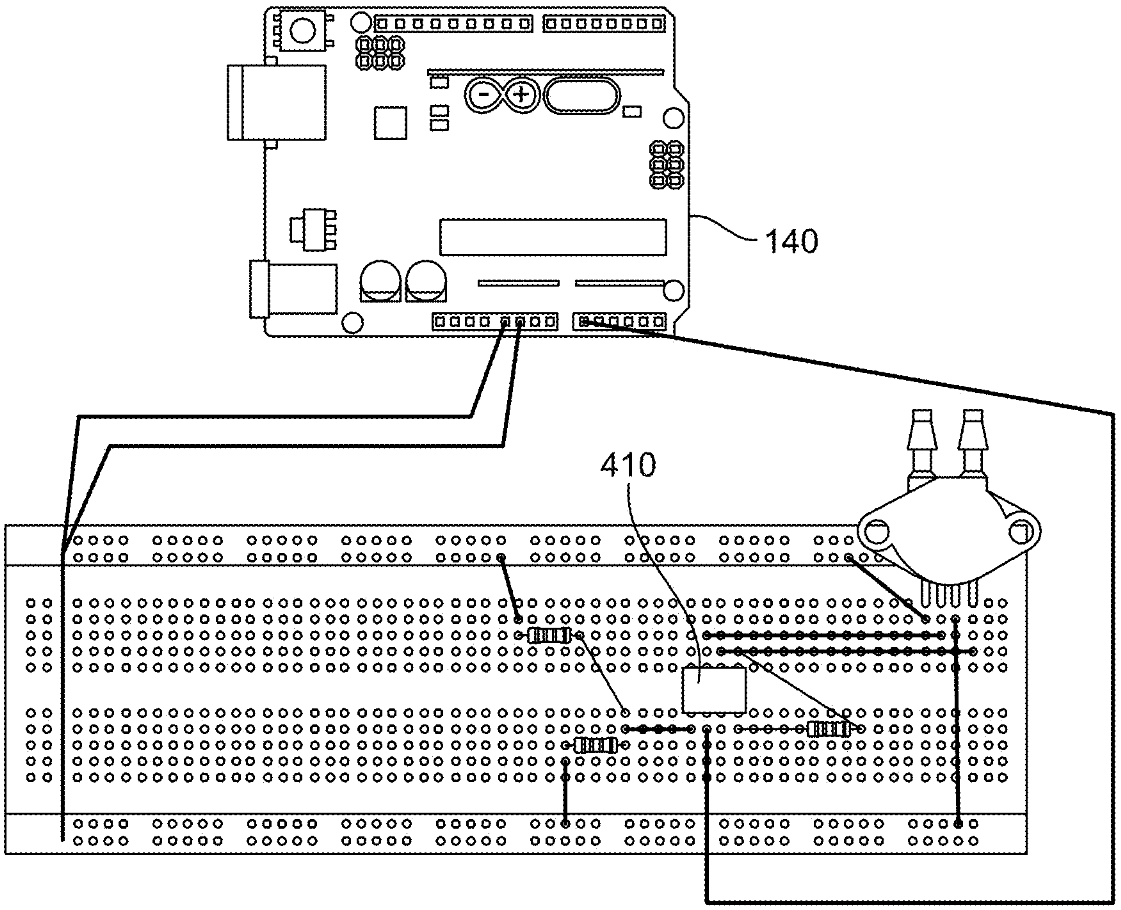
FIG. 17 illustrates electric connection of pressure sensor with the amplifier in the experimental set up of FIG. 15, according to certain embodiments.
Figure 18:
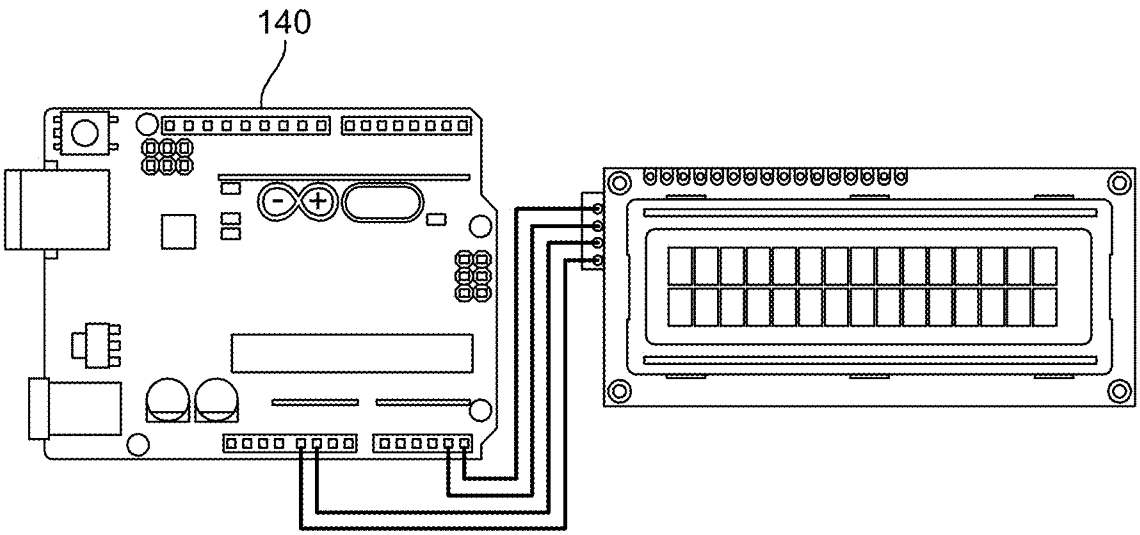
FIG. 18 illustrates electric connection of a liquid crystal display (LCD) with a microcontroller in the experimental set up of FIG. 15, according to certain embodiments.
Figure 19:
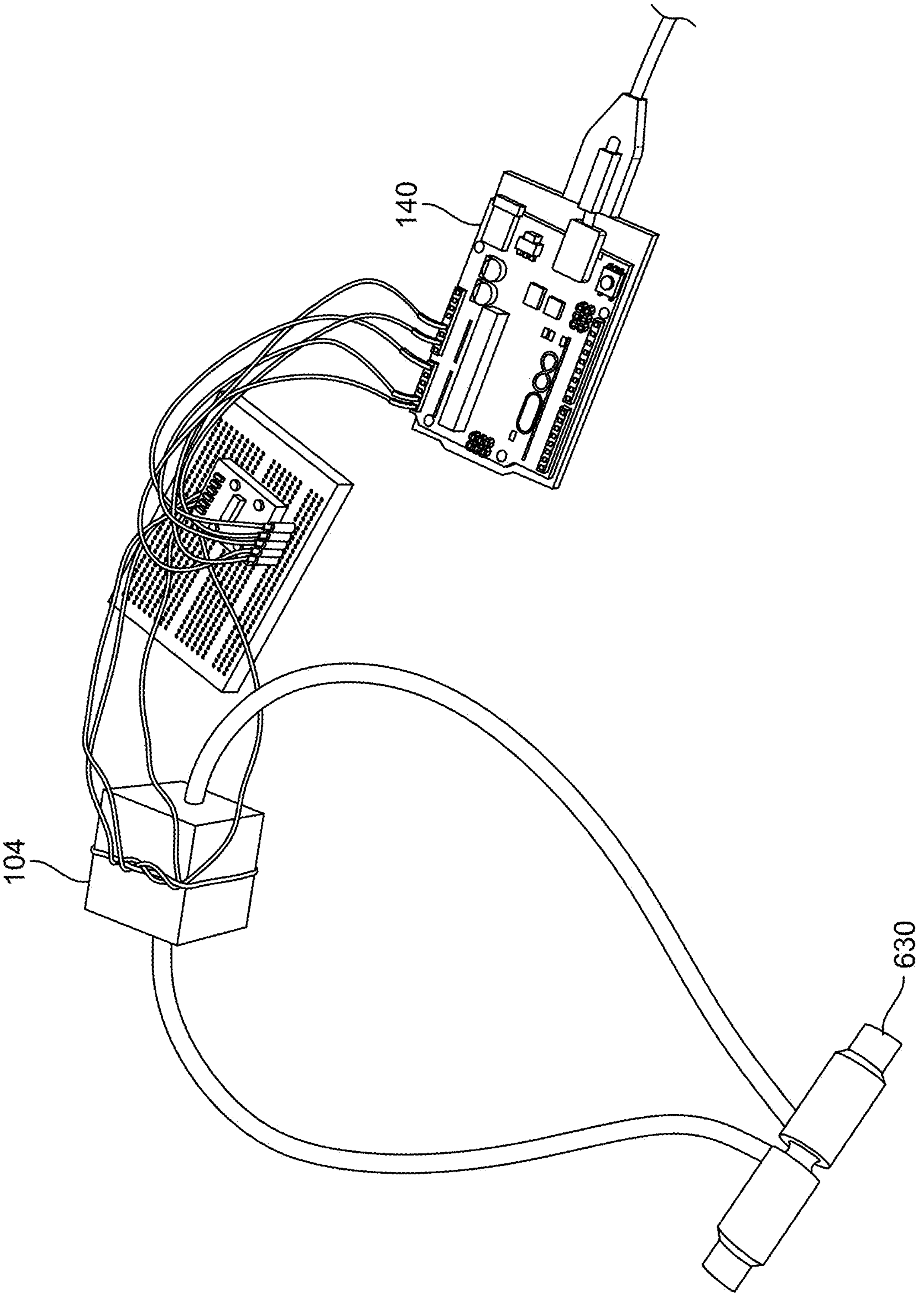
FIG. 19 illustrates connection of the differential pressure transducer with the modified orifice restriction unit in the experimental set up of FIG. 15, according to certain embodiments.

FIG. 15 illustrates an experimental setup 1500 of the modified orifice restriction unit 630 in a ventilation lab. The modified orifice restriction unit 630 was connected through a pipe to the humidifier 408. The differential pressure sensor (MPX10DP by FREESCALE, range of measurement±10 KPa, sensitivity 3.5 mV/kPa) [See: Reader-Harris, Michael. "Orifice Design." Orifice Plates and Venturi Tubes. Springer, Cham, 2015. 33-76, which is incorporated herein by reference in its entirety] was attached to two pressure static taps coming from the modified orifice restriction unit 630 to measure the pressure drop across it. The output from the differential pressure sensor was amplified by the amplifier 410 (AD620 Instrumentation amplifier) and the measured output flow was displayed in the LCD. The whole electronic circuit was constantly supplied by a voltage source of 5.00 V by the microcontroller 140 (ATmega328P), which was used as an analog to digital converter (ADC) as well to send the data to a host personal computer (PC). The multimeter 412 was used to test the sensitivity of the differential pressure sensor and to make sure the results are accurate. The modified orifice restriction unit 630 was tested for flow between 2 to 16 L/min, which is the maximum flow rate provided by the device. The gas blender 404 used in the experimental set up 1500 is shown in FIG. 16. The schematic diagram of the amplifier 410 connected with the differential pressure sensor and the microcontroller 140 is illustrated in FIG. 17. This circuit was implemented using Fritzing software. A schematic diagram of the LCD is shown in FIG. 18, where the I2C module reduces the number of wires used in the connection and makes the circuit less complicated. The LCD is further coupled with the microcontroller 140. FIG. 19 illustrates an experimental setup of the developed differential pressure transducer 104 connected to the modified orifice restriction unit 630.

Example 7: Error % Between the Two Restrictions

Pressure drop-1 was measured from a first restriction placed near the beginning of the pipe. In the HFNC device, the air is transformed from this restriction that is located near the machine. However, the restriction is allocated further away from the machine in order to provide more comfort to the patient. In order to test the effect of changing the placement of the restriction on the outputs, a second restriction was located two meters away from the first restriction, and the second restriction's pressure drop has been adapted as 'pressure drop-2'. Then, the error % was calculated between the pressure drop-1 and the pressure drop-2 for each of the four major designs, and for each diameter to determine if it is possible to rely on those values or not. All the values have been listed in Table 2.

TABLE 2

A comparation of the error % between pressure drop-1 & 2 of all the designs

| Error % between pressure drop-1&2 of all designs | | | | | |
|---|---|---|---|---|---|
| Diameter (mm) | Q (L/min) | Orifice | Modified orifice | Venturi | Modified Venturi |
| 3 | 2 | 82.65% | 72.82% | 50.52% | 40.64% |
| | 4 | 84.50% | 76.04% | 35.37% | 43.81% |
| | 6 | 80.88% | 58.37% | 48.16% | 40.86% |
| | 8 | 79.65% | 65.95% | 43.50% | 19.64% |
| | 10 | 69.68% | 58.46% | 48.34% | 37.61% |
| | 20 | 61.39% | 66.89% | 55.13% | 16.40% |
| | 30 | 56.69% | 63.47% | 43.48% | 29.17% |
| | 40 | 58.22% | 51.36% | 30.23% | 36.97% |
| | 50 | 68.59% | 55.18% | 43.39% | 40.60% |
| | 60 | 41.35% | 32.85% | 37.19% | 37.06% |
| 4 | 2 | 66.88% | 55.04% | 24.12% | 25.33% |
| | 4 | 49.67% | 46.42% | 30.53% | 19.55% |
| | 6 | 62.31% | 39.73% | 24.00% | 21.88% |
| | 8 | 57.49% | 50.13% | 20.64% | 19.59% |
| | 10 | 57.15% | 36.06% | 20.02% | 4.17% |
| | 20 | 48.04% | 43.89% | 15.16% | 7.36% |
| | 30 | 51.74% | 43.48% | 19.68% | 12.42% |
| | 40 | 50.83% | 40.15% | 21.48% | 5.81% |
| | 50 | 55.54% | 46.44% | 17.28% | 6.27% |
| | 60 | 54.92% | 41.51% | 20.63% | 10.48% |
| 5 | 2 | 49.36% | 21.44% | 1.29% | 11.86% |
| | 4 | 33.13% | 38.19% | 3.15% | 10.87% |
| | 6 | 32.81% | 25.48% | 5.95% | 8.92% |
| | 8 | 43.25% | 28.72% | 9.01% | 10.70% |
| | 10 | 34.10% | 20.67% | 0.70% | 10.87% |
| | 20 | 34.32% | 16.44% | 1.87% | 12.16% |
| | 30 | 34.46% | 51.55% | 5.14% | 7.00% |
| | 40 | 26.44% | 20.25% | 0.07% | 12.15% |
| | 50 | 26.28% | 13.19% | 3.97% | 12.25% |
| | 60 | 24.66% | 12.30% | 3.70% | 7.74% |
| 6 | 2 | 34.35% | 27.37% | 6.37% | 6.93% |
| | 4 | 25.42% | 23.28% | 7.06% | 9.07% |
| | 6 | 21.48% | 22.99% | 4.06% | 4.80% |
| | 8 | 26.72% | 14.67% | 4.80% | 3.97% |
| | 10 | 22.35% | 18.17% | 1.97% | 5.93% |
| | 20 | 18.40% | 13.90% | 1.86% | 3.14% |
| | 30 | 14.02% | 12.87% | 0.18% | 3.13% |
| | 40 | 19.57% | 12.12% | 3.18% | 3.71% |
| | 50 | 16.92% | 10.90% | 2.94% | 3.92% |
| | 60 | 13.50% | 9.66% | 2.86% | 3.17% |
| 7 | 2 | 31.91% | 18.86% | 8.37% | 7.35% |
| | 4 | 22.19% | 9.55% | 5.79% | 6.50% |
| | 6 | 8.13% | 2.67% | 6.66% | 6.94% |
| | 8 | 15.54% | 4.06% | 6.56% | 5.34% |
| | 10 | 10.30% | 7.86% | 1.90% | 4.59% |
| | 20 | 7.90% | 9.20% | 4.35% | 3.66% |
| | 30 | 9.50% | 13.77% | 5.65% | 4.57% |
| | 40 | 6.89% | 10.33% | 3.95% | 7.76% |
| | 50 | 7.39% | 13.55% | 2.32% | 3.51% |
| | 60 | 7.44% | 13.45% | 3.47% | 4.58% |
| 8 | 2 | 23.95% | 25.94% | 4.89% | 6.19% |
| | 4 | 19.75% | 11.57% | 6.74% | 5.05% |
| | 6 | 16.80% | 3.49% | 6.23% | 4.89% |
| | 8 | 9.56% | 0.79% | 5.42% | 5.52% |
| | 10 | 9.17% | 0.80% | 5.50% | 3.74% |
| | 20 | 3.44% | 5.80% | 1.91% | 3.09% |
| | 30 | 3.62% | 3.26% | 2.69% | 2.52% |
| | 40 | 3.18% | 7.05% | 2.02% | 2.03% |
| | 50 | 4.00% | 5.77% | 2.42% | 1.77% |
| | 60 | 0.60% | 5.64% | 1.98% | 2.47% |

Example 8: Calculations of the Accuracy % of Both Restriction Locations

The design of the present disclosure has been tested in two different locations, where the first one was near the inlet of the pipe and the second one was 2 m away from the inlet.

The decision on where to place the restriction has been made after considering the accuracies of the data in both locations. The accuracy of the first restriction was referred to as 'Accuracy %-1', while in the second restriction it was referred to as 'Accuracy %-2'. The data of those accuracies is shown in Table 3 for all the designs.

TABLE 3

The accuracy % of all designs in both restriction locations

| | | Modified Orifice | | Orifice | | Venturi | | Modified Venturi | |
|---|---|---|---|---|---|---|---|---|---|
| Diameter (mm) | Q (L/min) | Accuracy %-1 | Accuracy %-2 | Accuracy %-1 | Accuracy %-2 | Accuracy %-1 | Accuracy %-2 | Accuracy %-1 | Accuracy %-2 |
| 3 | 2 | 22.68% | 59.69% | 6.70% | 61.13% | −8.82% | 23.45% | −8.45% | 16.44% |
| | 4 | 18.44% | 60.07% | 2.72% | 61.69% | −7.21% | 13.81% | −5.93% | 20.59% |
| | 6 | 30.58% | 55.21% | 2.96% | 57.57% | −7.01% | 22.95% | −5.46% | 18.90% |
| | 8 | 25.13% | 56.31% | 3.78% | 56.60% | −6.67% | 19.82% | −5.97% | 5.00% |
| | 10 | 21.85% | 49.63% | 10.74% | 50.85% | −5.73% | 24.00% | −4.93% | 17.12% |
| | 20 | 16.44% | 51.91% | 14.48% | 46.86% | −18.21% | 20.81% | −5.75% | 3.31% |
| | 30 | 18.33% | 50.64% | 10.98% | 41.42% | −5.92% | 20.37% | −4.62% | 11.95% |
| | 40 | 15.62% | 41.15% | 4.44% | 38.23% | −5.81% | 11.62% | −4.81% | 16.79% |
| | 50 | 16.27% | 43.94% | 4.41% | 46.43% | −5.80% | 20.39% | −4.27% | 19.63% |
| | 60 | 20.70% | 35.02% | 1.58% | 24.63% | −6.23% | 15.81% | −4.33% | 17.23% |
| 4 | 2 | 8.01% | 38.32% | −20.87% | 30.44% | −21.24% | −5.61% | −9.53% | 5.35% |
| | 4 | 9.68% | 33.89% | −6.02% | 24.78% | −17.11% | 2.39% | −6.36% | 4.60% |
| | 6 | 10.11% | 30.22% | −19.16% | 26.85% | −16.39% | −1.47% | −5.49% | 6.76% |
| | 8 | 6.88% | 34.25% | −18.39% | 22.81% | −15.73% | −3.10% | −3.68% | 7.02% |
| | 10 | 8.13% | 26.54% | −20.27% | 21.27% | −16.00% | −3.74% | −3.50% | −1.32% |
| | 20 | 4.62% | 28.56% | −12.22% | 19.11% | −15.48% | −6.37% | −3.01% | 0.86% |
| | 30 | 2.37% | 26.60% | −20.19% | 16.50% | −15.58% | −3.59% | −3.29% | 3.33% |
| | 40 | 4.42% | 26.05% | −20.82% | 15.28% | −15.72% | −2.54% | −3.12% | −0.08% |
| | 50 | 2.31% | 28.51% | −19.03% | 20.63% | −15.73% | −5.26% | −3.07% | 0.22% |
| | 60 | 2.36% | 25.33% | −24.63% | 16.32% | −16.48% | −3.77% | −2.98% | 2.57% |
| 5 | 2 | 2.52% | 13.59% | −18.79% | 15.46% | −18.75% | −17.98% | −16.03% | −8.93% |
| | 4 | 3.35% | 24.01% | −17.16% | 4.20% | −13.77% | −11.97% | −12.37% | −6.08% |
| | 6 | 4.69% | 17.72% | −18.06% | 3.23% | −13.37% | −9.95% | −10.85% | −5.79% |
| | 8 | 4.01% | 18.96% | −17.36% | 11.59% | −12.30% | −7.12% | −10.43% | −4.35% |
| | 10 | 6.34% | 16.57% | −19.52% | 2.98% | −11.97% | −11.58% | −10.56% | −4.37% |
| | 20 | 2.86% | 11.20% | −21.30% | 1.69% | −12.70% | −11.65% | −12.27% | −5.22% |
| | 30 | 0.83% | 30.98% | −20.59% | 2.37% | −13.27% | −10.32% | −12.82% | −8.80% |
| | 40 | 1.29% | 11.85% | −22.04% | −4.66% | −12.04% | −12.08% | −13.36% | −6.25% |
| | 50 | −0.14% | 6.70% | −20.41% | −3.39% | −11.88% | −14.08% | −13.25% | −6.08% |
| | 60 | 0.52% | 6.84% | −20.22% | −4.35% | −11.85% | −9.76% | −12.48% | −8.04% |
| 6 | 2 | −5.31% | 10.25% | −24.39% | −0.78% | −19.50% | −15.63% | −15.27% | −11.20% |
| | 4 | −4.31% | 8.64% | −23.54% | −6.69% | −13.46% | −9.38% | −10.36% | −5.24% |
| | 6 | −3.97% | 8.76% | −23.30% | −9.26% | −12.15% | −9.85% | −9.71% | −7.04% |
| | 8 | −1.72% | 6.03% | −24.28% | −6.39% | −11.53% | −8.82% | −8.68% | −6.50% |
| | 10 | −2.52% | 7.27% | −22.04% | −7.54% | −10.72% | −9.62% | −8.19% | −4.93% |
| | 20 | −4.14% | 3.37% | −24.09% | −12.09% | −10.63% | −11.65% | −9.28% | −7.55% |
| | 30 | −5.79% | 1.25% | −25.45% | −16.32% | −10.90% | −11.00% | −9.56% | −7.83% |
| | 40 | −6.34% | 0.31% | −26.39% | −13.35% | −10.68% | −12.42% | −9.35% | −7.30% |
| | 50 | −7.45% | −1.43% | −27.00% | −15.76% | −10.32% | −11.93% | −9.62% | −7.45% |
| | 60 | −7.23% | −1.92% | −27.00% | −18.12% | −10.66% | −12.23% | −9.46% | −7.71% |
| 7 | 2 | −4.64% | 5.74% | −23.27% | −1.72% | −71.38% | −64.05% | −61.84% | −55.78% |
| | 4 | −5.45% | −0.29% | −24.70% | −9.99% | −61.05% | −56.32% | −53.21% | −48.15% |
| | 6 | −3.96% | −5.34% | −12.50% | −7.84% | −59.62% | −54.22% | −51.25% | −45.91% |
| | 8 | −2.24% | −4.30% | −22.71% | −12.77% | −58.98% | −53.68% | −48.99% | −44.96% |
| | 10 | −2.01% | −5.94% | −22.61% | −16.12% | −58.90% | −57.38% | −49.04% | −45.57% |
| | 20 | −1.92% | −6.51% | −24.69% | −19.67% | −60.11% | −56.59% | −48.98% | −46.23% |
| | 30 | −2.94% | −9.80% | −25.43% | −19.33% | −61.36% | −56.74% | −49.28% | −45.83% |
| | 40 | −3.72% | −8.94% | −27.13% | −22.68% | −61.46% | −58.24% | −49.30% | −43.39% |
| | 50 | −4.33% | −11.17% | −28.03% | −23.21% | −61.49% | −59.60% | −49.28% | −46.64% |
| | 60 | −4.50% | −11.31% | −28.77% | −23.89% | −61.13% | −58.31% | −49.53% | −46.06% |
| 8 | 2 | −2.09% | 12.14% | −20.69% | −5.25% | −23.19% | −20.15% | −18.68% | −14.95% |
| | 4 | −2.73% | 3.39% | −21.63% | −8.96% | −16.60% | −12.60% | −11.88% | −9.01% |
| | 6 | −2.04% | −0.25% | −21.75% | −11.05% | −14.61% | −10.98% | −9.53% | −6.82% |
| | 8 | 0.01% | 0.41% | −20.58% | −14.67% | −13.65% | −10.53% | −8.18% | −5.16% |
| | 10 | 0.58% | 0.18% | −20.02% | −14.38% | −13.12% | −9.97% | −7.39% | −5.36% |
| | 20 | 1.49% | −1.33% | −20.06% | −17.98% | −12.38% | −11.30% | −6.21% | −4.55% |
| | 30 | 0.50% | −1.11% | −21.09% | −18.88% | −12.51% | −10.99% | −5.94% | −4.59% |
| | 40 | −0.46% | −3.95% | −22.95% | −20.98% | −12.41% | −11.27% | −5.84% | −4.76% |
| | 50 | −1.35% | −4.23% | −23.90% | −21.40% | −12.39% | −11.02% | −5.76% | −4.81% |
| | 60 | −1.25% | −4.07% | −23.95% | −23.58% | −12.34% | −11.22% | −5.68% | −4.37% |

Example 9: Calculations Accuracy % Between the Measured and Actual

Calculations of the accuracy % of the simulated output flow rates and the actual flow rates have been infused in the inlet. The result of the pressure drops at each location has gone through further calculations in order to determine each location's flow rate output. Then, the accuracy % of each design at each location has been calculated and listed as shown in Table 3.

Example 10: Turbulence & Flow Direction

Figure 20A:
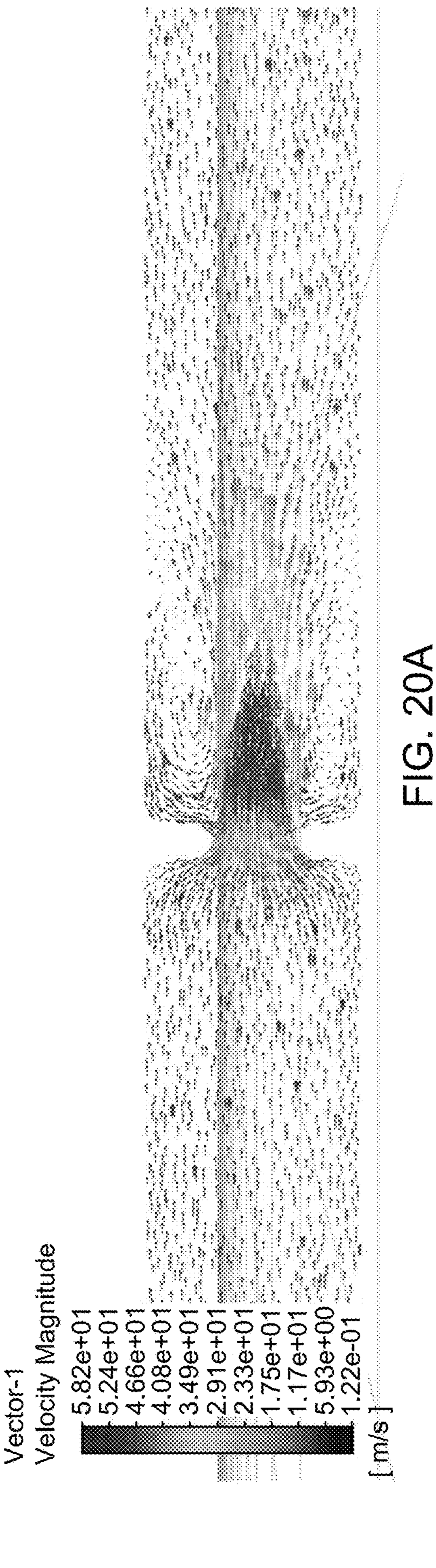
FIG. 20A illustrates turbulence effect and flow direction of a first restriction in a 5 mm-modified orifice restriction unit, according to certain embodiments.
Figure 20B:
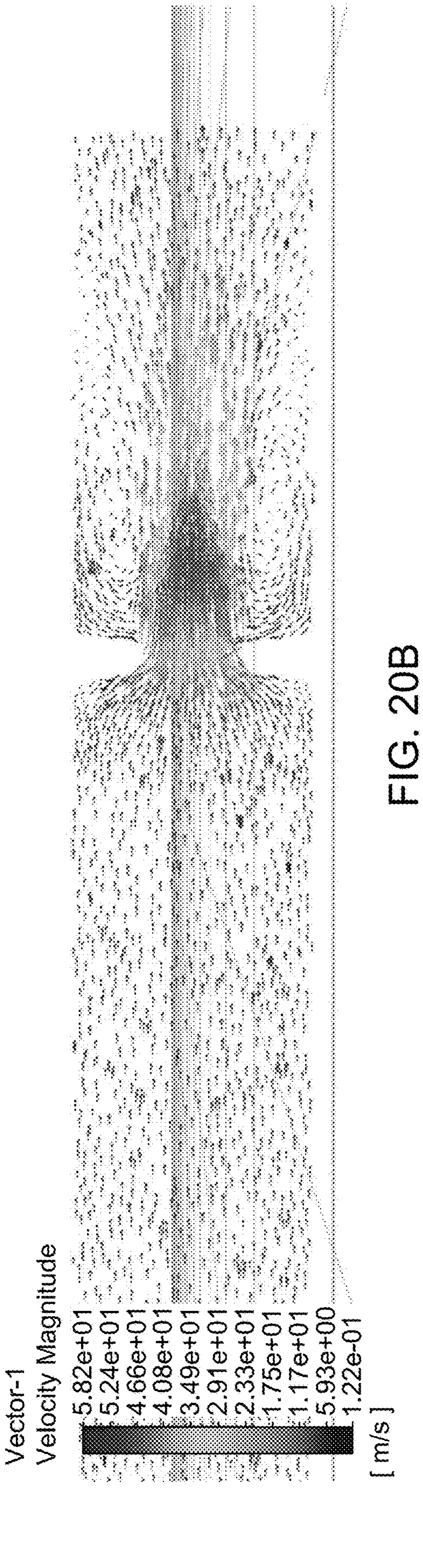
FIG. 20B illustrates turbulence effect and flow direction of a second restriction in a 5 mm-modified orifice restriction unit, according to certain embodiments.

The turbulence effect of the best design 'the modified orifice-5 mm' of both restrictions are shown in FIG. 20A and FIG. 20B. Moreover, the arrows show the directions in which the oxygen was flowing inside the pipe before and after the restriction. The turbulence was generated by the restriction, as the pipe of 12 mm was reduced in this restriction to be only 5 mm.

Example 11: Analysis of the Error % Between the Two Restrictions

From Table 2, data of each design's error % between the two restrictions (Pressure drop-1&2) were compared. However, the comparison between the pressure drops was not the most accurate, as more parameters such as the diameter, cross-sectional area and most importantly the flow rate should be considered. The flow rate is better to determine which design is the most accurate.

Example 12: Analysis and Comparison Between the Accuracy % of Both Restriction Locations Referring to Table 3, it is observed that the overall accuracy of all the designs were higher in the first location where restriction-1 was placed for most of the designs. Accordingly, it was concluded that the 'modified orifice-5 mm' model was used according to Table 3 and 4, after comparing all the accuracies and the simulated flow rates at all locations. Therefore, the restriction was placed in the first location near the inlet of the pipe as it had a higher accuracy % of the flow rate in the present disclosure.

TABLE 4

The 'Modified orifice-5 mm' flow rate results in the first location (first restriction)

| Diameter (mm) | $Q_{Actual}$ (L/min) | Q1 (L/min) | Accuracy %-1 |
|---|---|---|---|
| 3 | 2 | 1.5464 | 22.68% |
| | 4 | 3.2626 | 18.44% |
| | 6 | 4.1654 | 30.58% |
| | 8 | 5.9900 | 25.13% |
| | 10 | 7.8148 | 21.85% |
| | 20 | 16.7129 | 16.44% |
| | 30 | 24.5011 | 18.33% |
| | 40 | 33.7531 | 15.62% |
| | 50 | 41.8669 | 16.27% |
| | 60 | 47.5812 | 20.70% |
| 4 | 2 | 1.8398 | 8.01% |
| | 4 | 3.6126 | 9.68% |
| | 6 | 5.3932 | 10.11% |
| | 8 | 7.4492 | 6.88% |
| | 10 | 9.1871 | 8.13% |
| | 20 | 19.0763 | 4.62% |
| | 30 | 29.2893 | 2.37% |
| | 40 | 38.2327 | 4.42% |
| | 50 | 48.8442 | 2.31% |
| | 60 | 58.5826 | 2.36% |
| 5 | 2 | 1.9497 | 2.52% |
| | 4 | 3.8662 | 3.35% |
| | 6 | 5.7186 | 4.69% |
| | 8 | 7.6792 | 4.01% |
| | 10 | 9.3664 | 6.34% |
| | 20 | 19.4284 | 2.86% |
| | 30 | 29.7499 | 0.83% |
| | 40 | 39.4824 | 1.29% |
| | 50 | 50.0682 | −0.14% |
| | 60 | 59.6867 | 0.52% |
| 6 | 2 | 2.1062 | −5.31% |
| | 4 | 4.1725 | −4.31% |
| | 6 | 6.2382 | −3.97% |

TABLE 4-continued

The 'Modified orifice-5 mm' flow rate results in the first location (first restriction)

| Diameter (mm) | $Q_{Actual}$ (L/min) | Q1 (L/min) | Accuracy %-1 |
|---|---|---|---|
| | 8 | 8.1377 | −1.72% |
| | 10 | 10.2515 | −2.52% |
| | 20 | 20.8284 | −4.14% |
| | 30 | 31.7357 | −5.79% |
| | 40 | 42.5349 | −6.34% |
| | 50 | 53.7269 | −7.45% |
| | 60 | 64.3386 | −7.23% |
| 7 | 2 | 2.0929 | −4.64% |
| | 4 | 4.2178 | −5.45% |
| | 6 | 6.2379 | −3.96% |
| | 8 | 8.1792 | −2.24% |
| | 10 | 10.2006 | −2.01% |
| | 20 | 20.3844 | −1.92% |
| | 30 | 30.8809 | −2.94% |
| | 40 | 41.4867 | −3.72% |
| | 50 | 52.1646 | −4.33% |
| | 60 | 62.7028 | −4.50% |
| 8 | 2 | 2.0418 | −2.09% |
| | 4 | 4.1092 | −2.73% |
| | 6 | 6.1227 | −2.04% |
| | 8 | 7.9990 | 0.01% |
| | 10 | 9.9425 | 0.58% |
| | 20 | 19.7022 | 1.49% |
| | 30 | 29.8496 | 0.50% |
| | 40 | 40.1858 | −0.46% |
| | 50 | 50.6747 | −1.35% |
| | 60 | 60.7530 | −1.25% |

Example 13: Comparison of Accuracy % Between the Measured & Calculated

The accuracy of all designs were taken into consideration to find the best location out of all the designs. Not only the accuracy % of all designs were taken into consideration to identify the best model to be used, but also the output flow rate values were taken into consideration. The output flow rate values cannot exceed the flow rates injected to avoid causing further complications to the patients. The values of the best design 'the modified orifice-5 mm' and the best location 'location-1' are shown in Table 4.

Example 14: Turbulence & Flow Direction

Figure 21A:
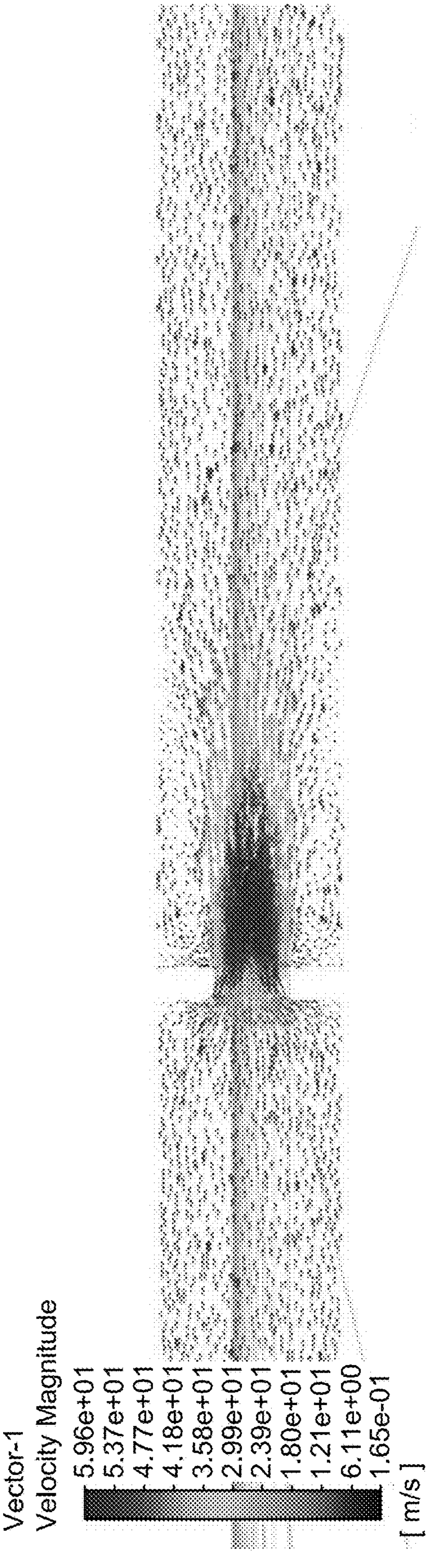
FIG. 21A illustrates turbulence effect and flow direction of a first restriction in a 5 mm-basic orifice restriction unit, according to certain embodiments.
Figure 21B:
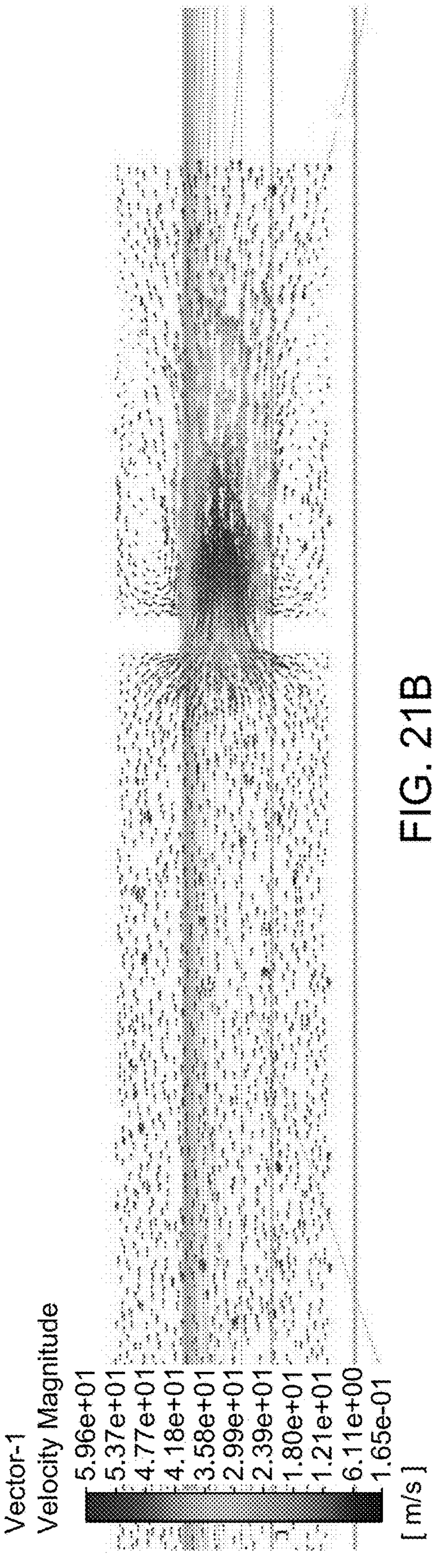
FIG. 21B illustrates turbulence effect and flow direction of a second restriction in a 5 mm-basic orifice restriction unit, according to certain embodiments.

The turbulence shown in FIG. 20A and FIG. 20B show the turbulence effect of both restriction-1&2 in the 'modified orifice-5 mm' model. However, the turbulence of the basic orifice and the modified orifice were compared before identifying the best model, as it was one of the criteria of choosing the best design. FIG. 21A and FIG. 21B show the turbulence of restriction-1&2 of the 'Orifice-5 mm' model. Thus, it is observed that the turbulence of the modified orifice was slightly better than the basic orifice.

Example 15: Modified Orifice Sensitivity Curves

Figure 22A:
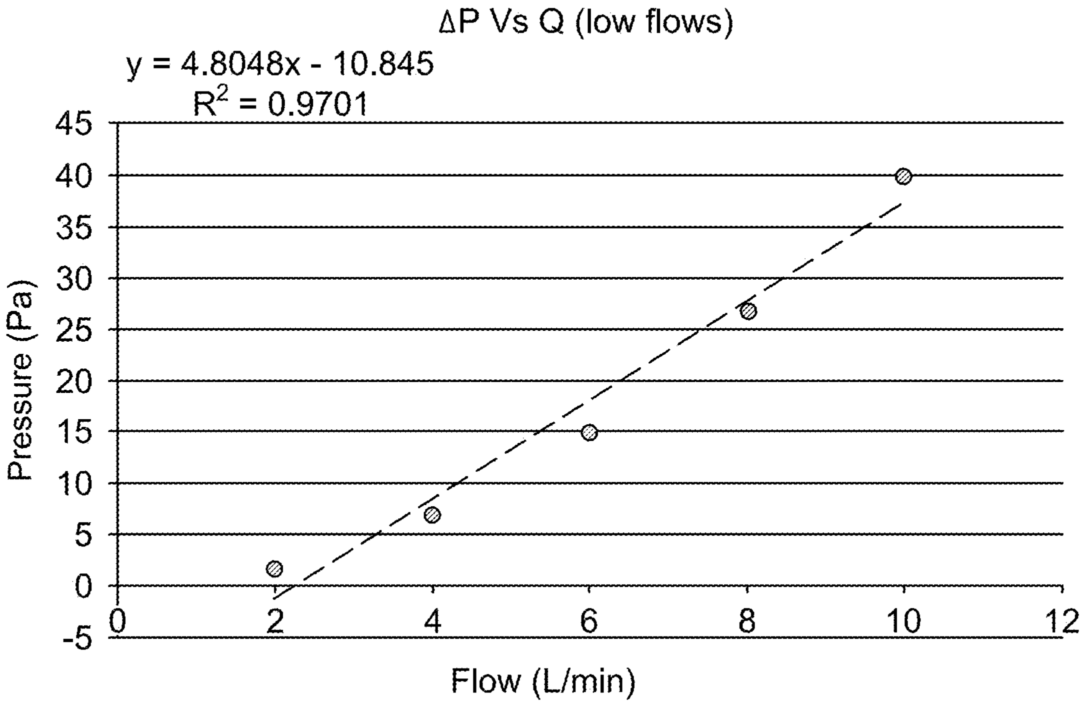
FIG. 22A is a graphical representation of a sensitivity curve for low flows in the modified orifice restriction unit, according to certain embodiments.
Figure 22B:
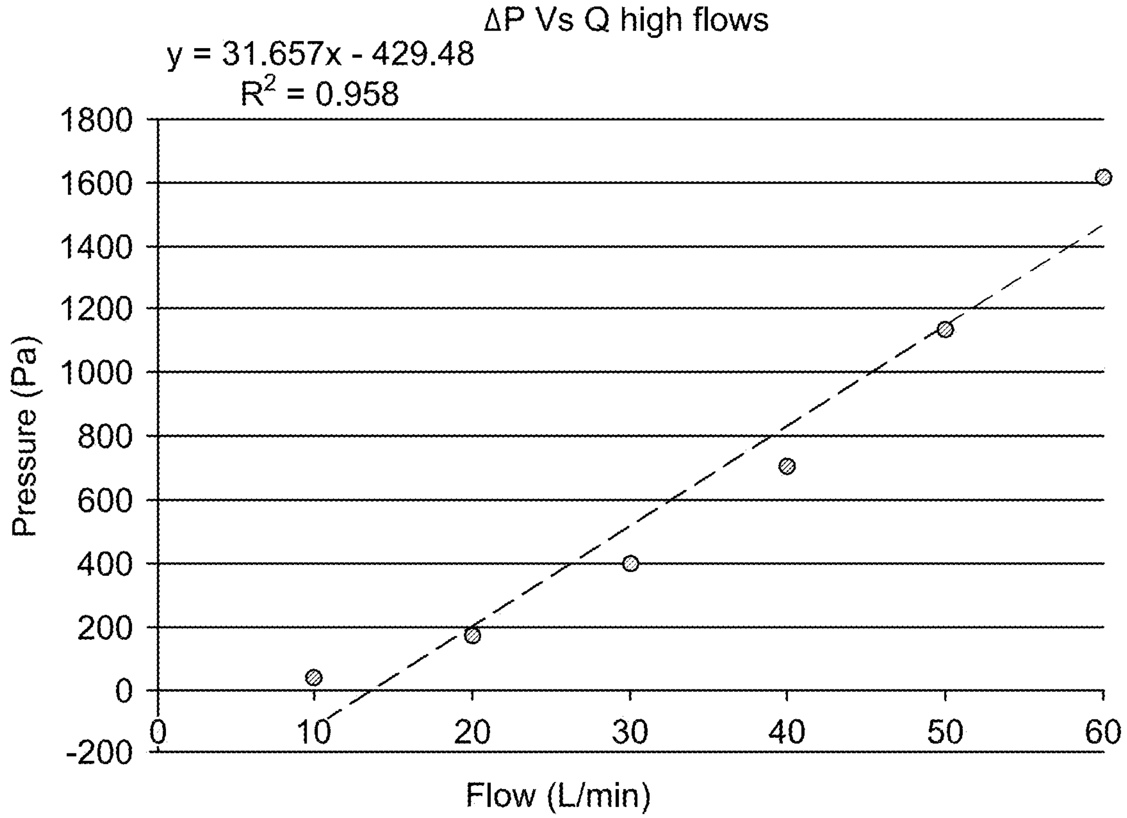
FIG. 22B is a graphical representation of a sensitivity curve for high flows in the modified orifice restriction unit, according to certain embodiments.

Based on the simulation results and the verification test, the modified orifice was chosen in the present disclosure and a sensitivity curve was done for it, by applying a linear fitting of the data. Where there are two curves, one for the low flows between 0-10 L/min, and the other is for high flow 10-60 L/min. By having both curves, shown in FIG. 22A and FIG. 22B, flow rate value can be found at any detected pressure for the modified orifice design.

Example 16: Modified Orifice Prototype with MPX10DP Pressure Sensor

After the experimental setup was done, a flow range between 2 to 16 L/min were applied, and the output voltage from the circuit was detected using the microcontroller 140 then it was converted into pressure and then into flow using the equations. The output flow rate was presented using Arduino's serial monitor and the LCD. The code used for this process is shown in FIG. 23. The output flow from the sensor were reported and compared with the simulation and the calculated results in Table 5 and FIG. 24.

TABLE 5

Output results from the prototype

| Input Flow | Prototype Output flow | Simulation Output flow | Error % |
|---|---|---|---|
| 2 L/min | 0.78 L/min | 1.949 L/min | 59.9% |
| 4 L/min | 2.90 L/min | 3.866 L/min | 24.98% |
| 6 L/min | 4.05 L/min | 5.719 L/min | 29.18% |
| 8 L/min | 5.28 L/min | 7.679 L/min | 31.24% |
| 10 L/min | 7.83 L/min | 9.359 L/min | 16.34% |

Figure 24:
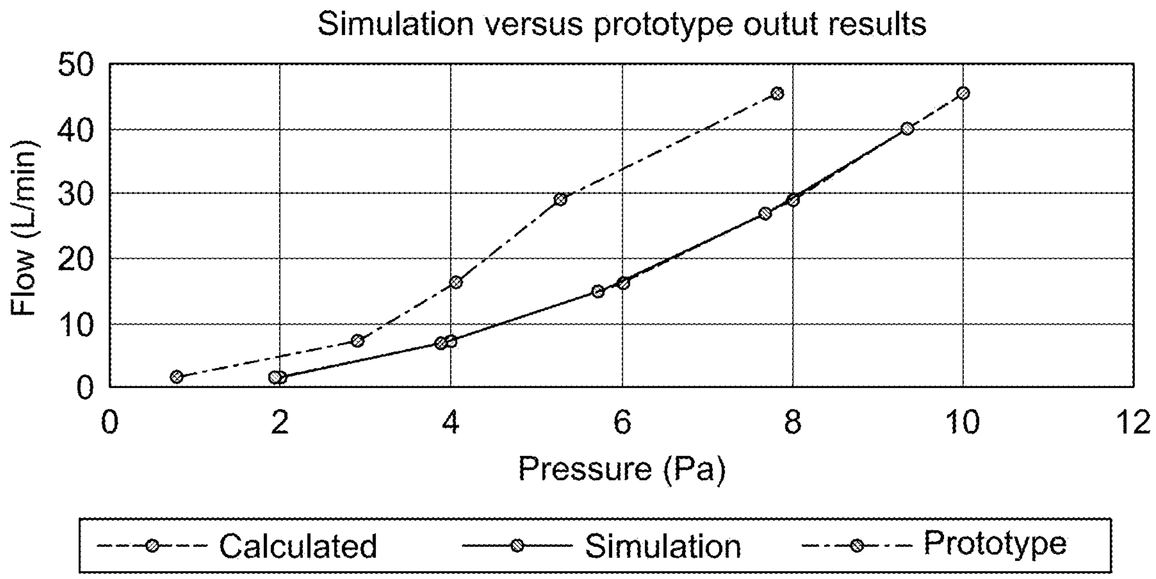
FIG. 24 is a graphical representation showing prototype results compared with simulation results and calculation results, according to certain embodiments.
Figure 26A:
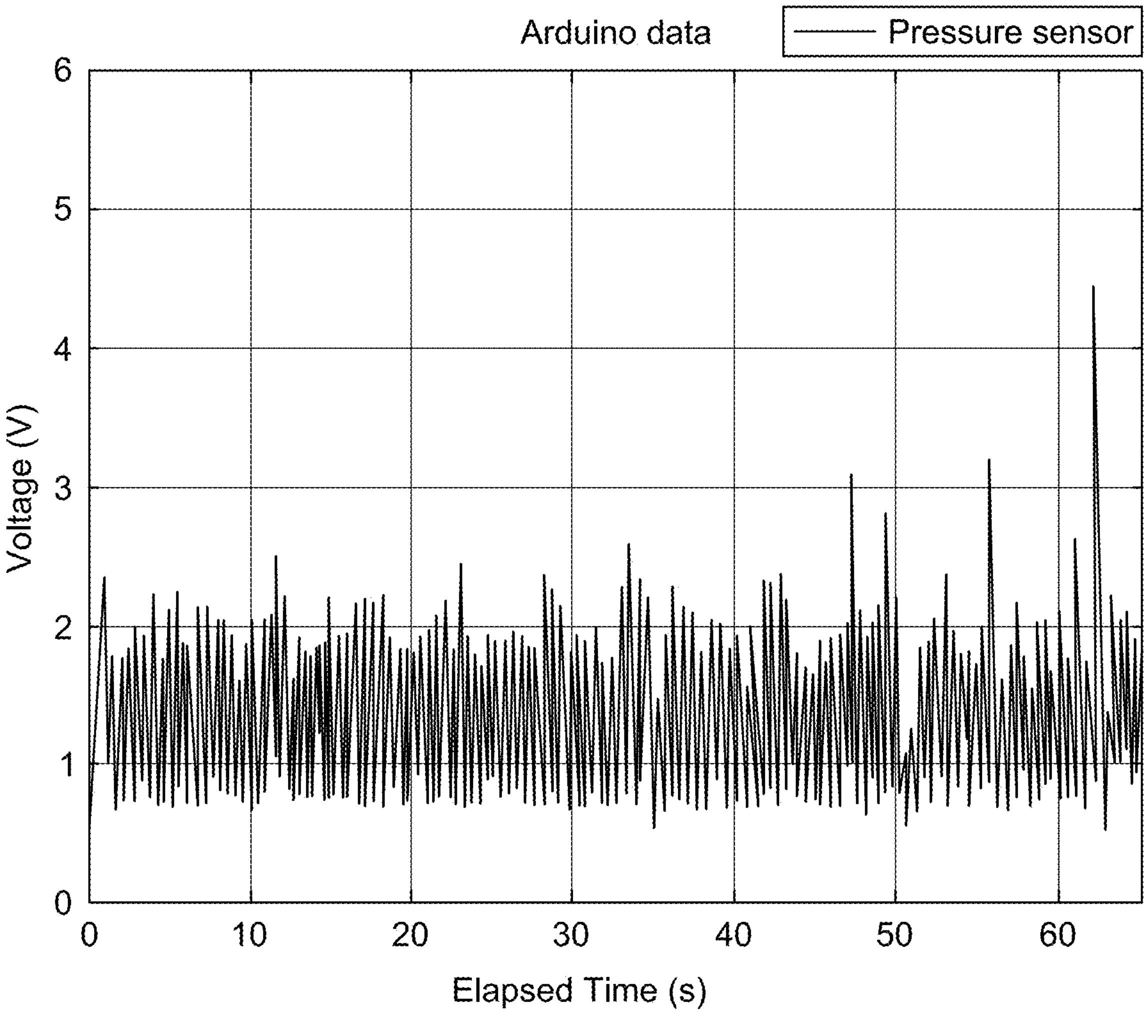
FIG. 26A is a graphical representation showing an output voltage for a flow rate of 2 L/min with a mean of 1.256V, according to certain embodiments.
Figure 26B:
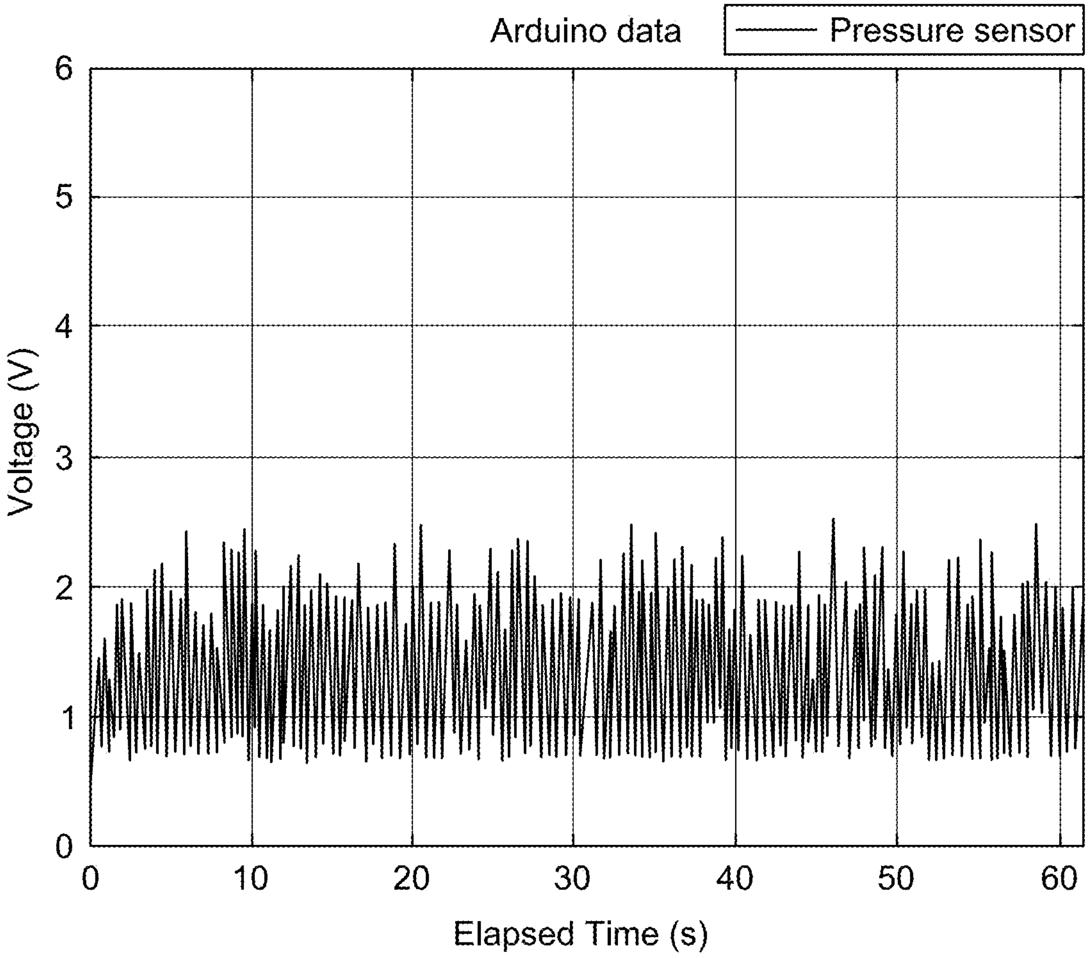
FIG. 26B is a graphical representation showing an output voltage for a flow rate of 4 L/min with a mean of 1.298V, according to certain embodiments.
Figure 26C:
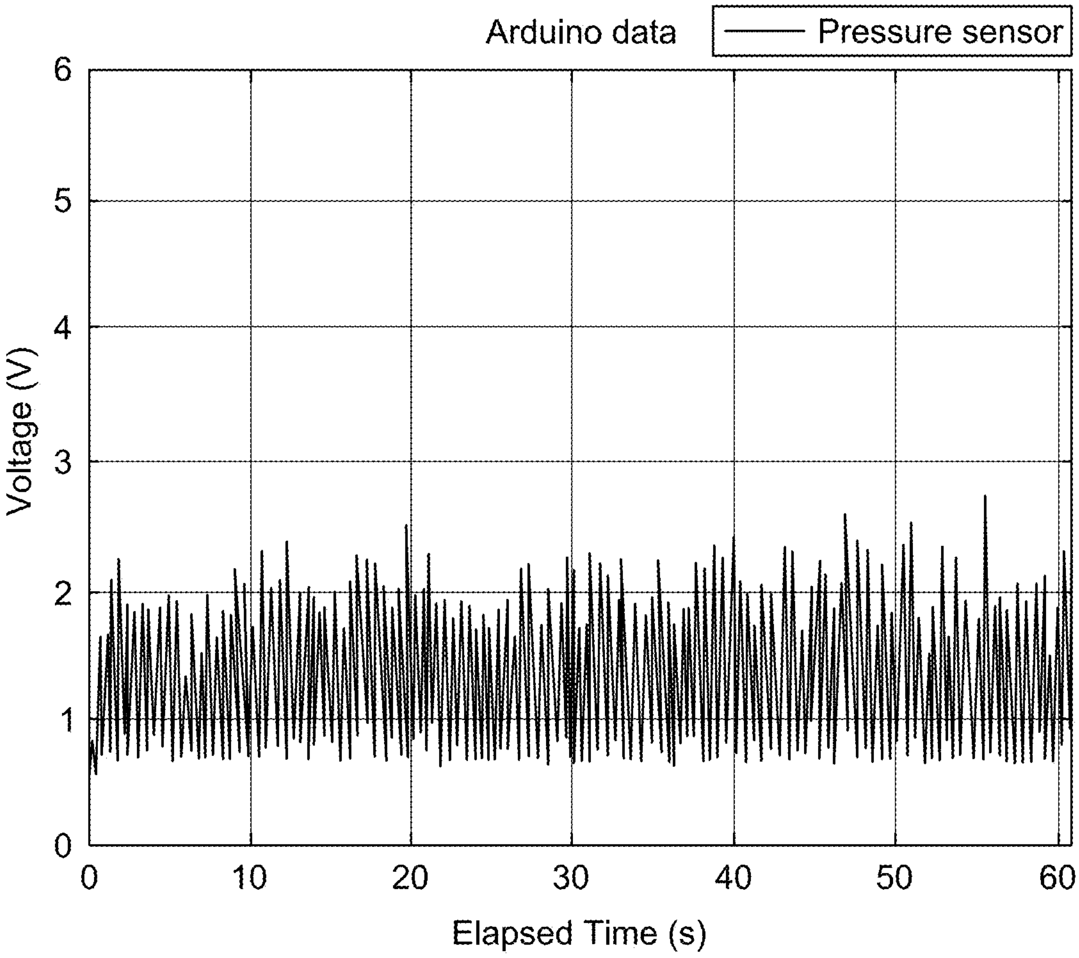
FIG. 26C is a graphical representation showing an output voltage for a flow rate of 6 L/min with a mean of 1.310V, according to certain embodiments.
Figure 26D:
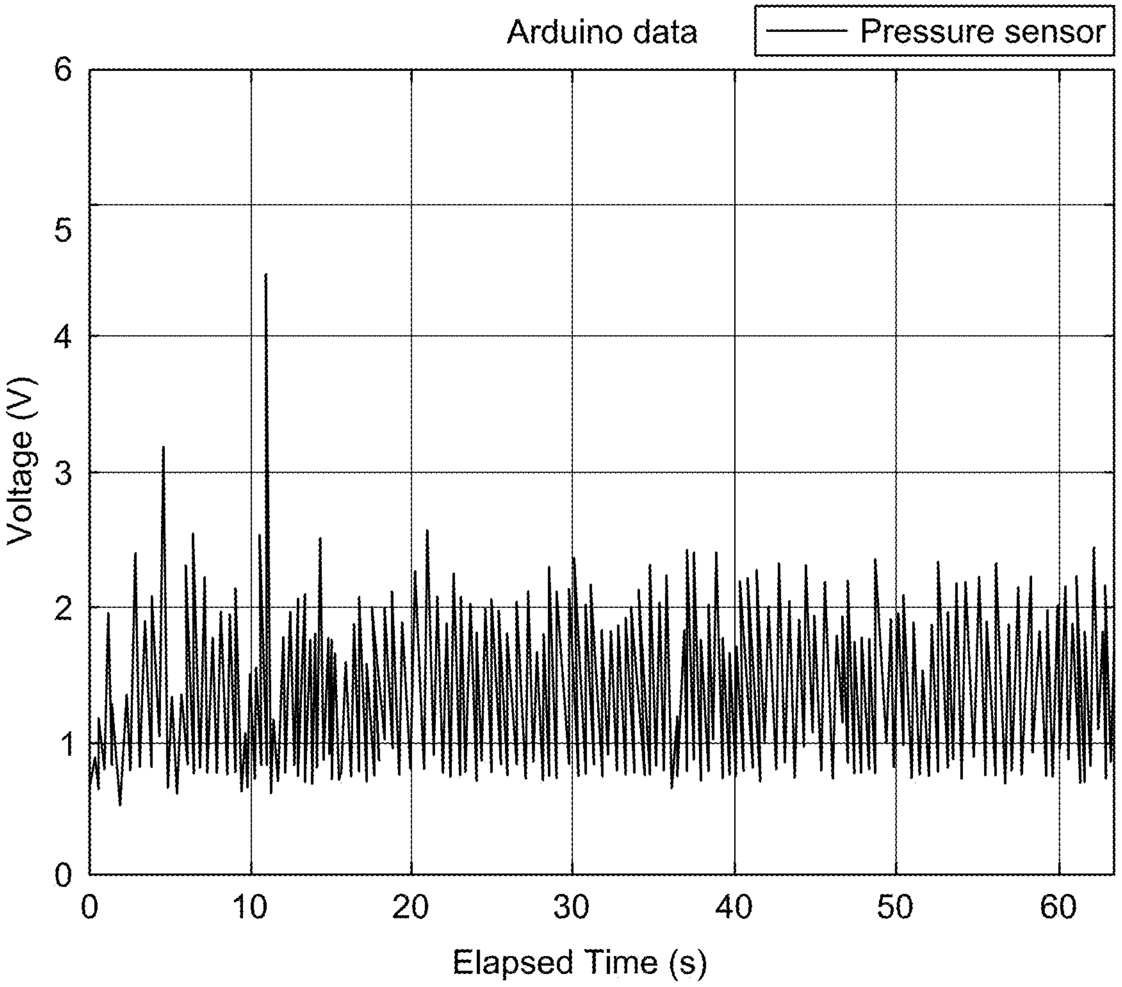
FIG. 26D is a graphical representation showing an output voltage for a flow rate of 8 L/min with a mean of 1.335V, according to certain embodiments.
Figure 26E:
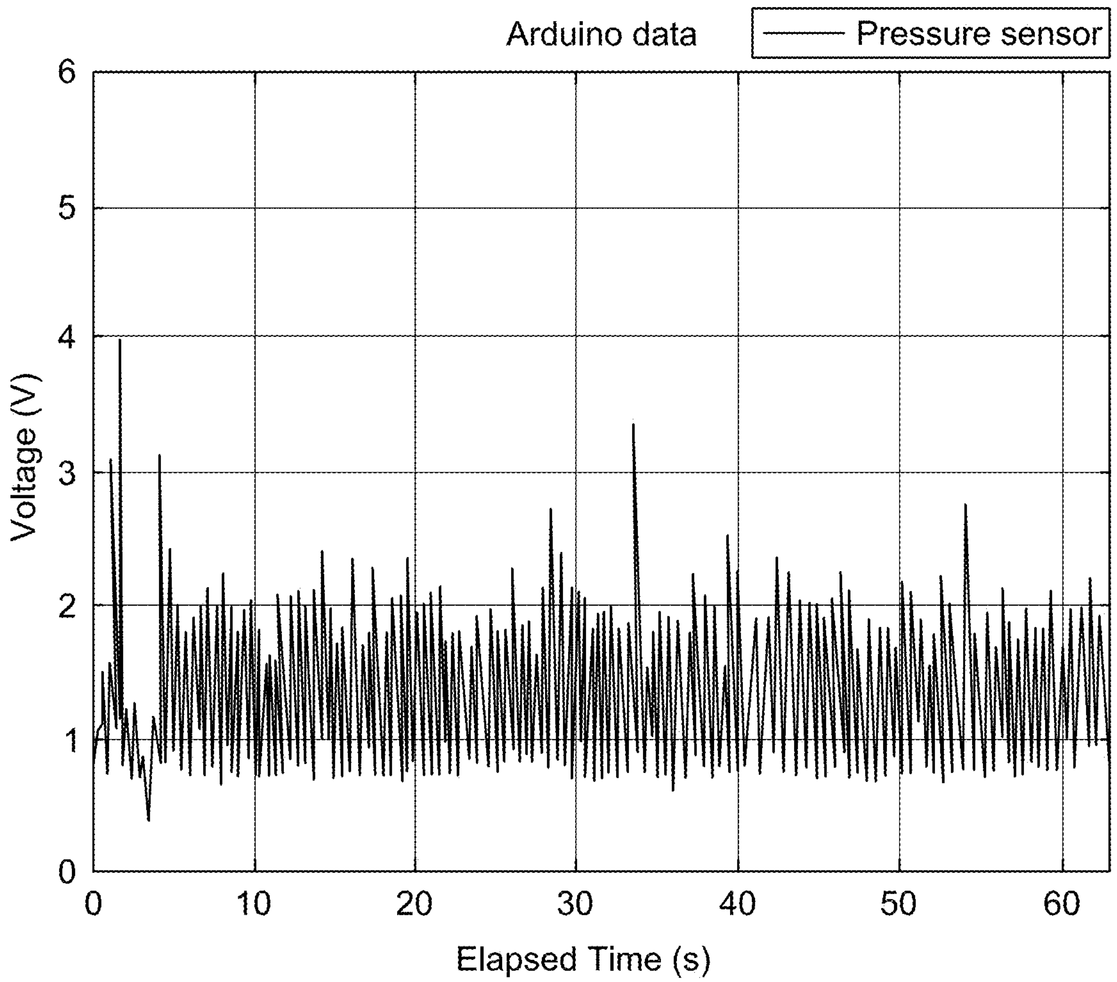
FIG. 26E is a graphical representation showing an output voltage for a flow rate of 10 L/min with a mean of 1.345V, according to certain embodiments.
Figure 26F:
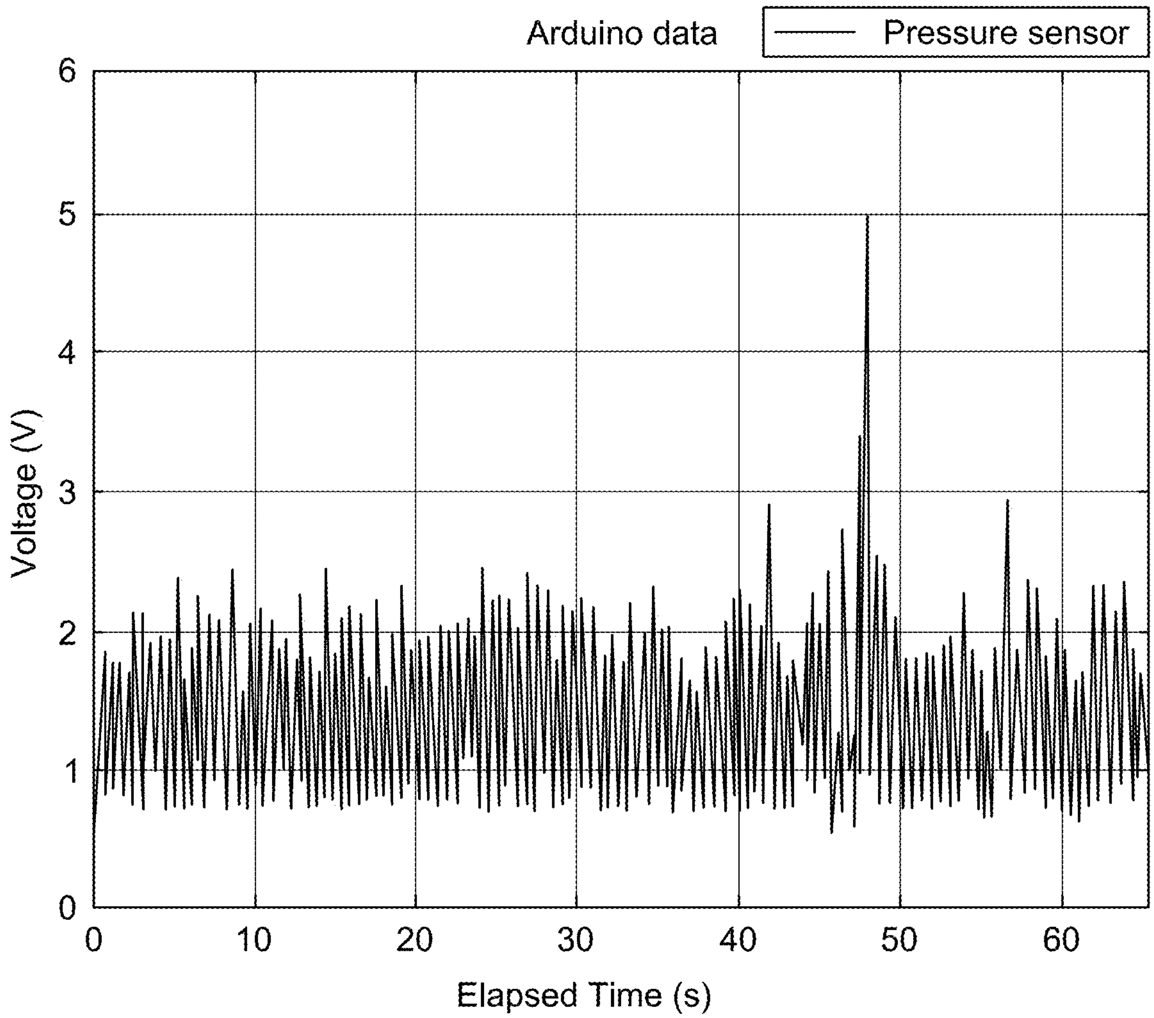
FIG. 26F is a graphical representation showing an output voltage for a flow rate of 12 L/min with a mean of 1.3630V, according to certain embodiments.
Figure 26G:
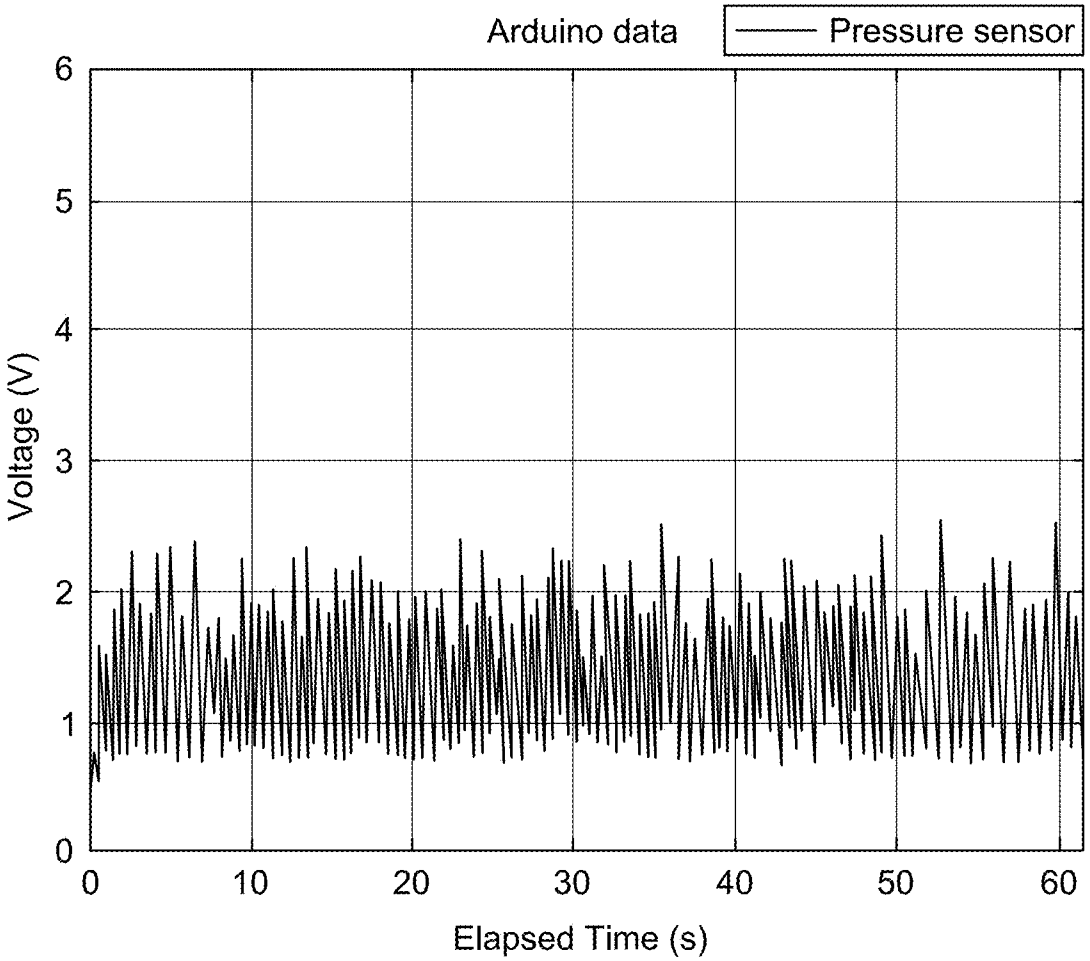
FIG. 26G is a graphical representation showing an output voltage for a flow rate of 14 L/min with a mean of 1.375V, according to certain embodiments.
Figure 26H:
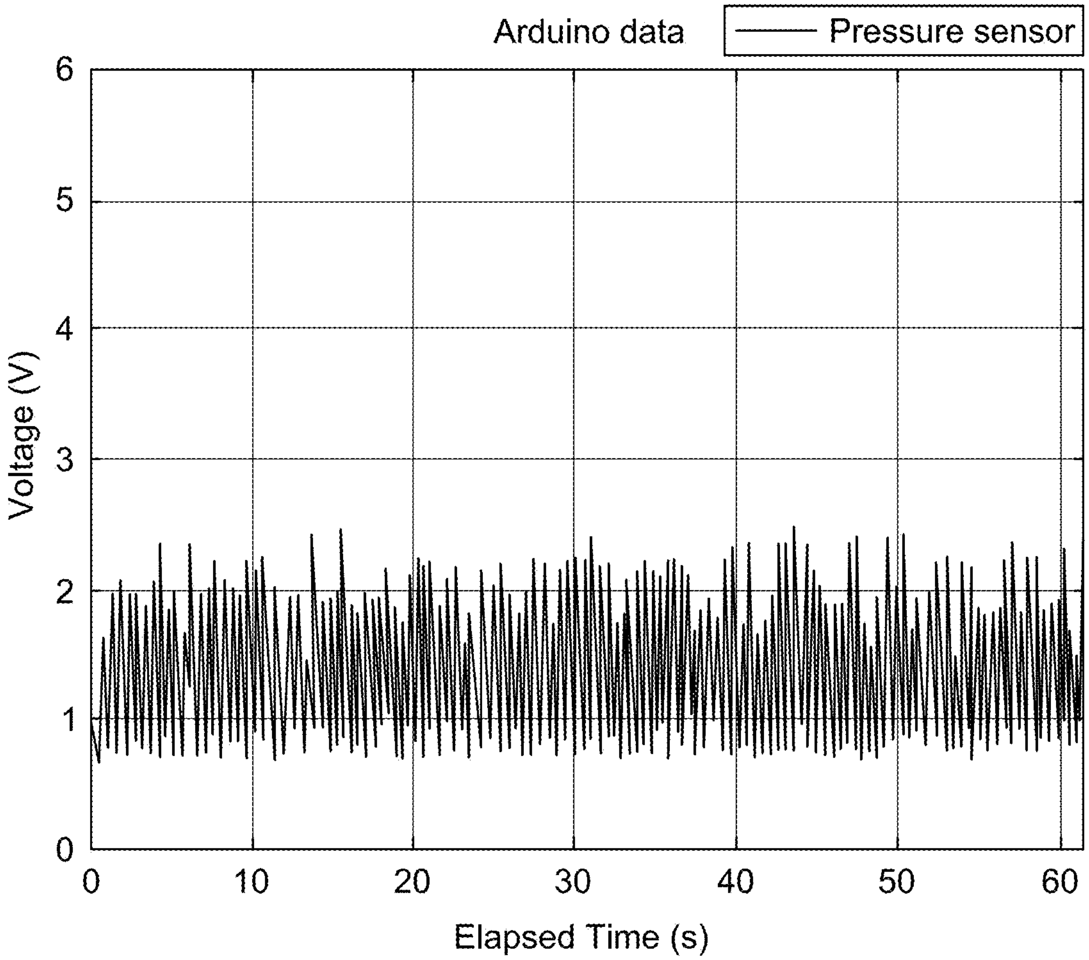
FIG. 26H is a graphical representation showing an output voltage for a flow rate of 16 L/min with a mean of 1.402V, according to certain embodiments.

As seen in FIG. 24, the simulation and the calculated results were almost the same, but the prototype results were not. Also, the results had a large error percent, it was fluctuating, and it did not exactly match with the simulation results due to several factors. First, the sensitivity of the sensor is very low, around 3.5 mV/KPa only so it did not give very precise results specially for low flows. Second, the simulated and the calculated flow were considered to be incompressible and frictionless fluid of laminar flow type. However, in reality there is no ideal flow, and every fluid might undergo turbulent effect, which is caused by restrictions, high speed, and long pipe length leading to less accurate readings. Third, as the fluid is moving in the system, its output results will be affected by the head loss phenomena. Head loss is the amount reduction in the sum of elevation head, pressure head and velocity head. This effect is unavoidable in actual fluids, and it caused by the friction between the fluid and the pipe's walls [See: "DOE Fundamentals Handbook: Thermodynamics, Heat Transfer, and Fluid Flow," DOE-HDBK-1012/3-92, U.S. Department of Energy, June 1992, which is incorporated herein by reference in its entirety]. Fourth, the effect of humidity and temperature. The flowmeter was tested using a heated humidifier device, where the output gas was humidified, and heated before delivering it to the nasal cannula. As the airflow has high relative humidity, which can reach 100% relative humidity in HFNC, the water vapor condensate on the modified orifice's restriction causing noticeable error in the measurements because of the unpredictable change in the pneumatic resistance [See: M. B. Jaffe, "Technical perspectives: gas flow measurement," in Capnography, J. S. Gravenstein, M. B. Jaffe, N. Gravenstein, and D. A. Palus, Eds., pp. 397-405, Cambridge University Press, NewYork, NY, USA, 2011, which is incorporated herein by reference in its entirety]. This effect strongly presents when using the flowmeter for a long period of time according to an experiment done on a commercial variable orifice flowmeter. Additionally, the pressure sensor used in the present disclosure is not temperature compensated, so the flowmeter will have different output depending on its temperature of gas.

Example 17: Modified Orifice Prototype with MPX5500DP Pressure Sensor

Figure 25:
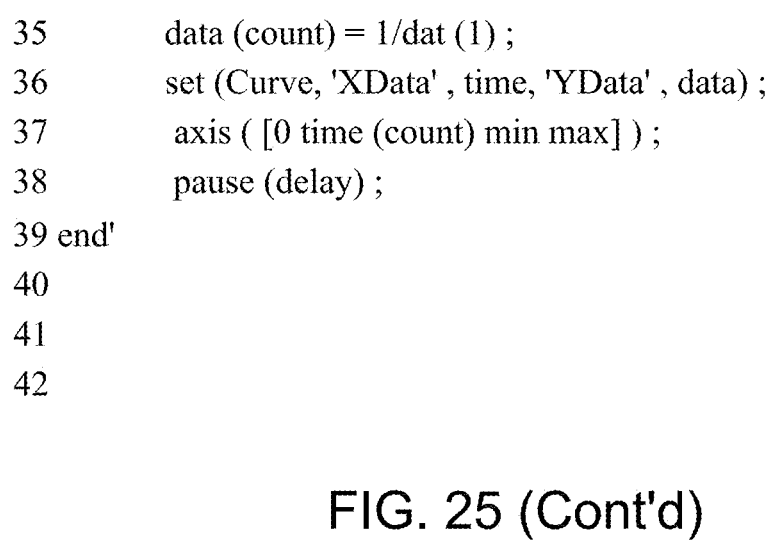

The last sensor used in the present disclosure was MPX5500DP, which is same as the previous sensor but with higher sensitivity. Also, this sensor does not need an amplifier circuit since its output voltage is between 0.2 V and 4 V so it can be connected directly with the microcontroller 140 to take the readings. This sensor was used to improve the output results and to compare the results between the sensors; however, the main sensor in the present disclosure is MPX10DP. The reading from this sensor was taken using MATLAB code, as shown in FIG. 25, where the output voltage from the pressure sensor was recorded with time. FIG. 26A to FIG. 26H show the output voltage for each flow rate between 2 to 16 L/min over 60 seconds.

As seen from the results, the sensor's output results are noisy and keep fluctuating, which is expected because of the air noise from the environment and the motion artifact since this sensor is very sensitive to any small movement. In general, when the input flow increased, the mean of the voltage output from the sensor also increased, which satisfy the direct relationship between the voltage and the flow rate. The output results can be further improved by using a low pass filter to increase the stability of the sensor.

Figure 27:
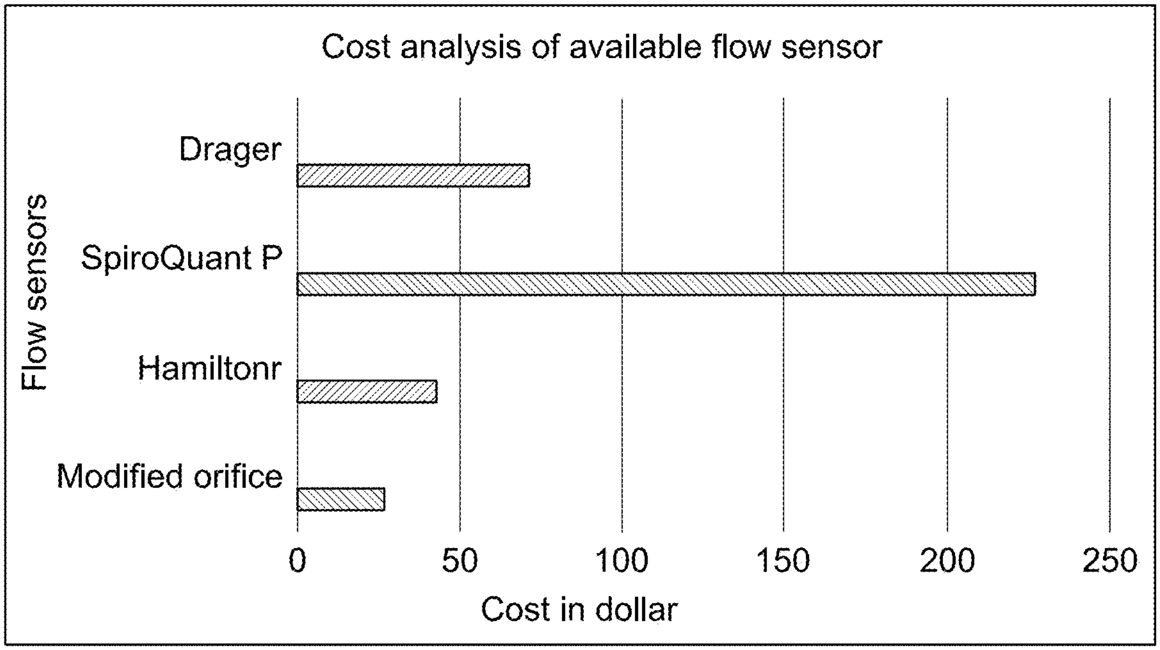
FIG. 27 is a graphical representation showing cost analysis of available pressure flow meters and the modified orifice restriction unit, according to certain embodiments.
Figure 28:
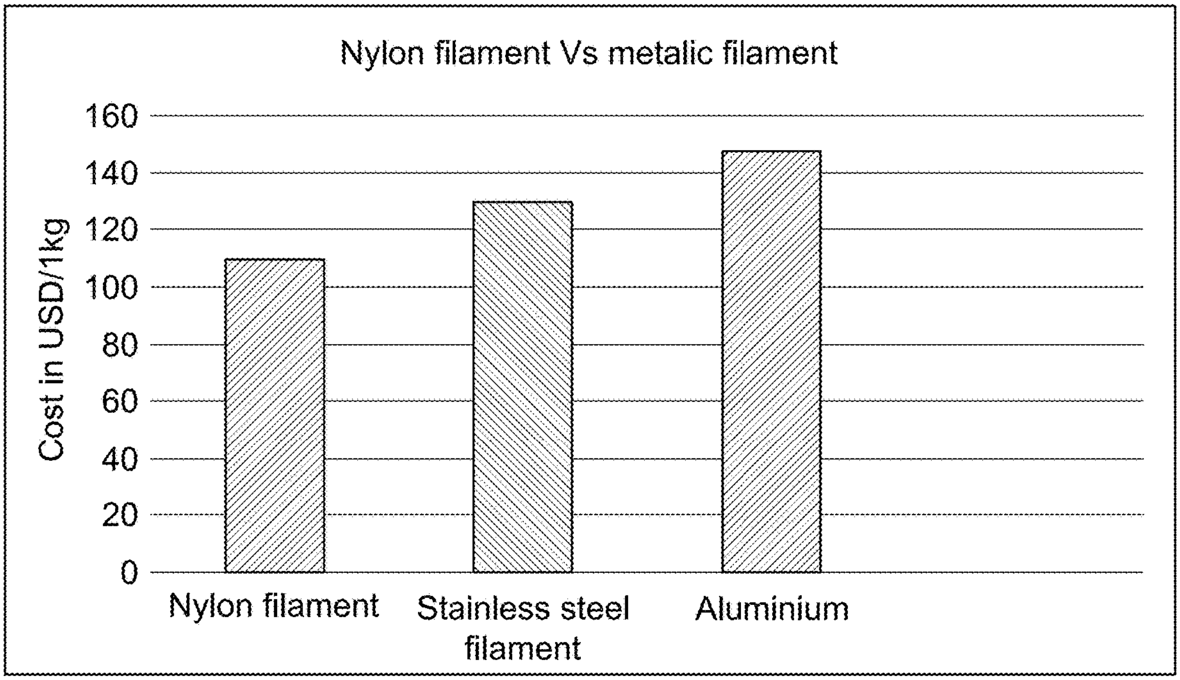
FIG. 28 is a graphical representation showing cost analysis of Nylon and Stainless-steel filament, according to certain embodiments.
Figure 29A:
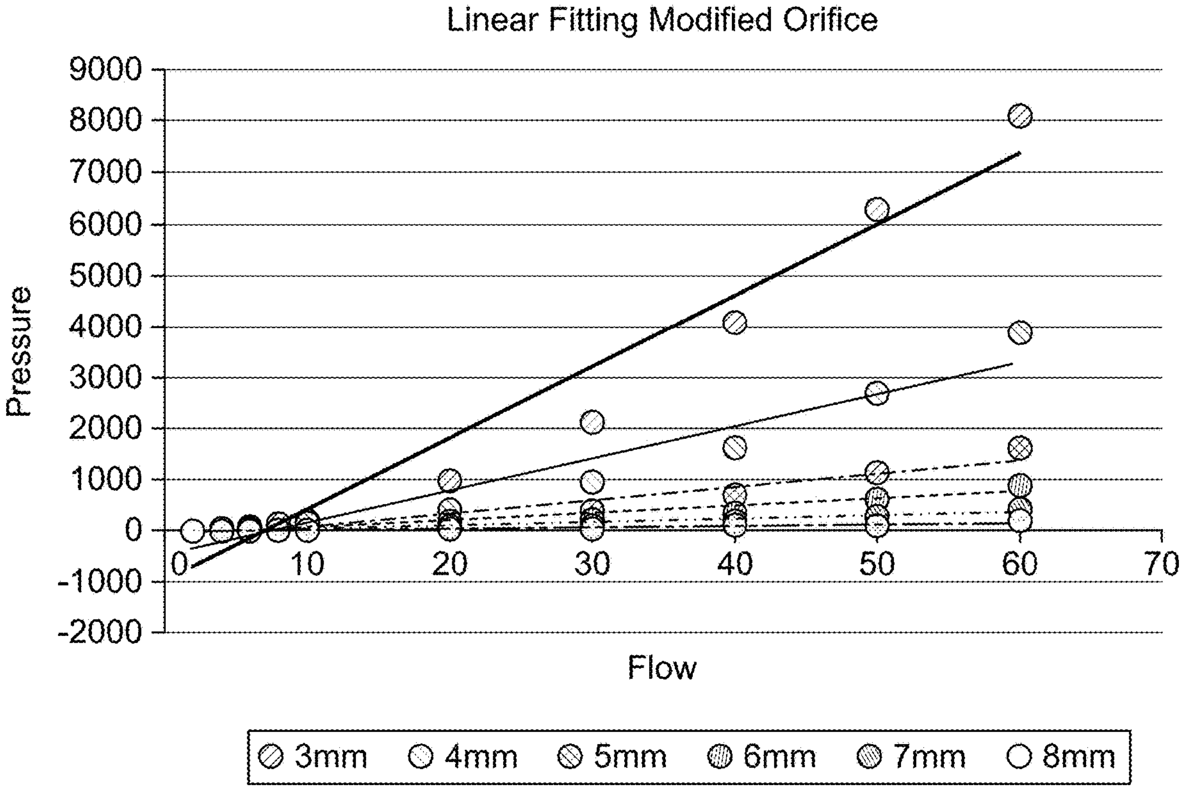
FIG. 29A is a graphical representation showing a linear fitting curve of the modified orifice restriction unit, according to certain embodiments.
Figure 29B:
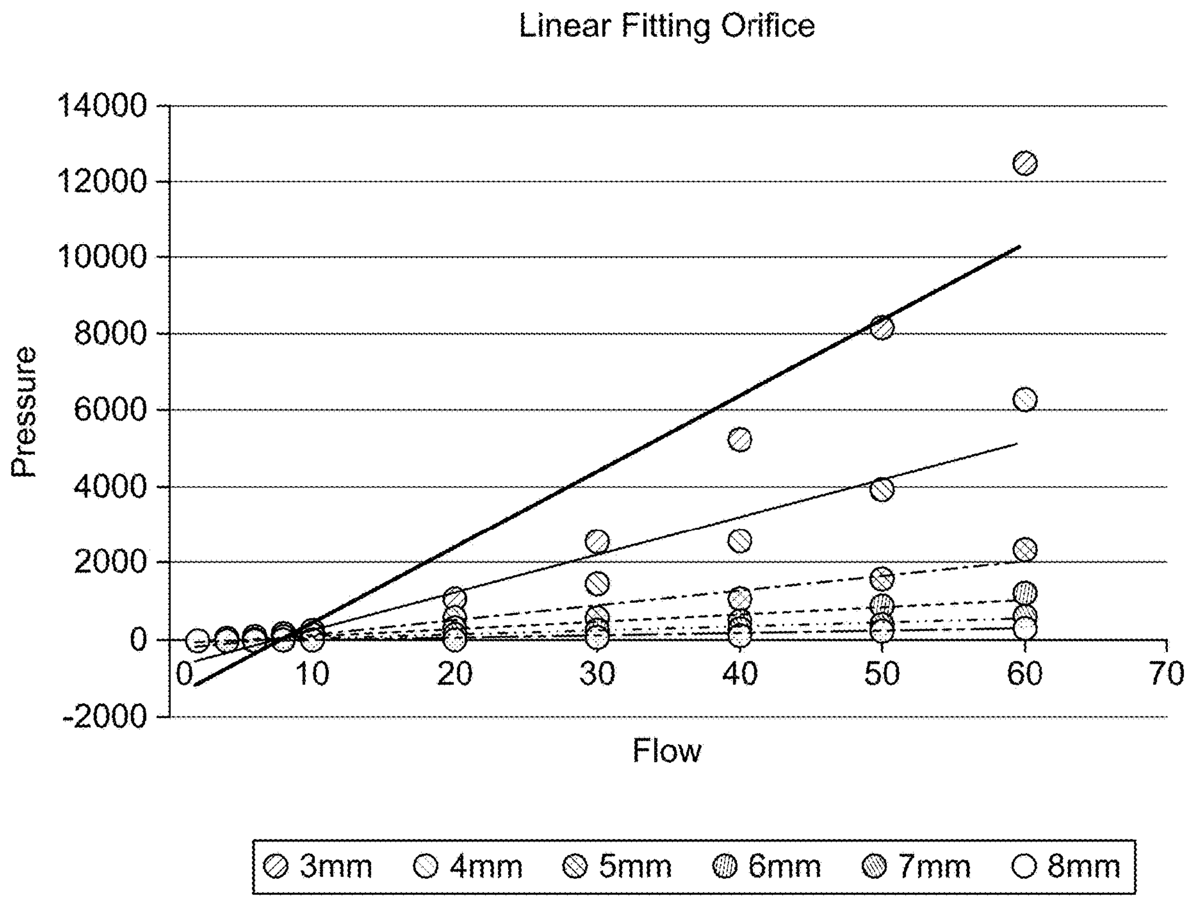
FIG. 29B is a graphical representation showing a linear fitting curve of a basic orifice restriction unit, according to certain embodiments.
Figure 30A:
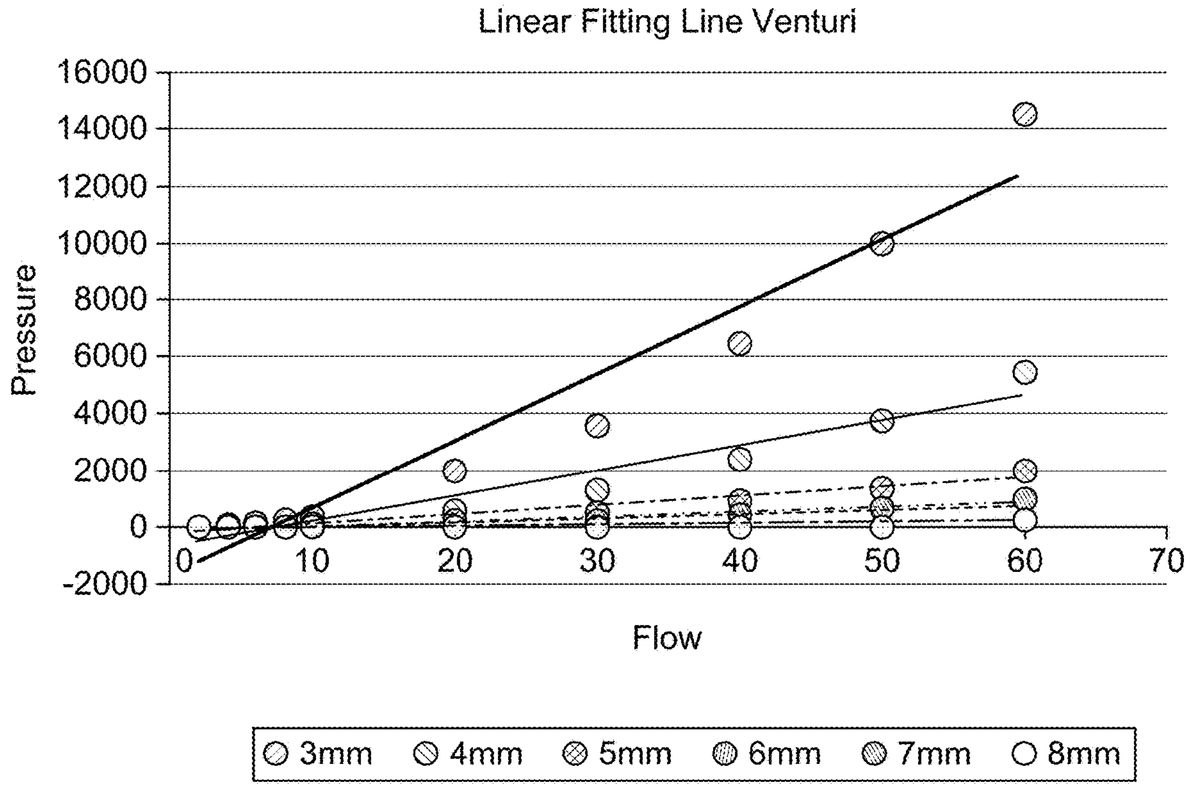
FIG. 30A is a graphical representation showing a linear fitting curve of a venturi restriction unit, according to certain embodiments.
Figure 30B:
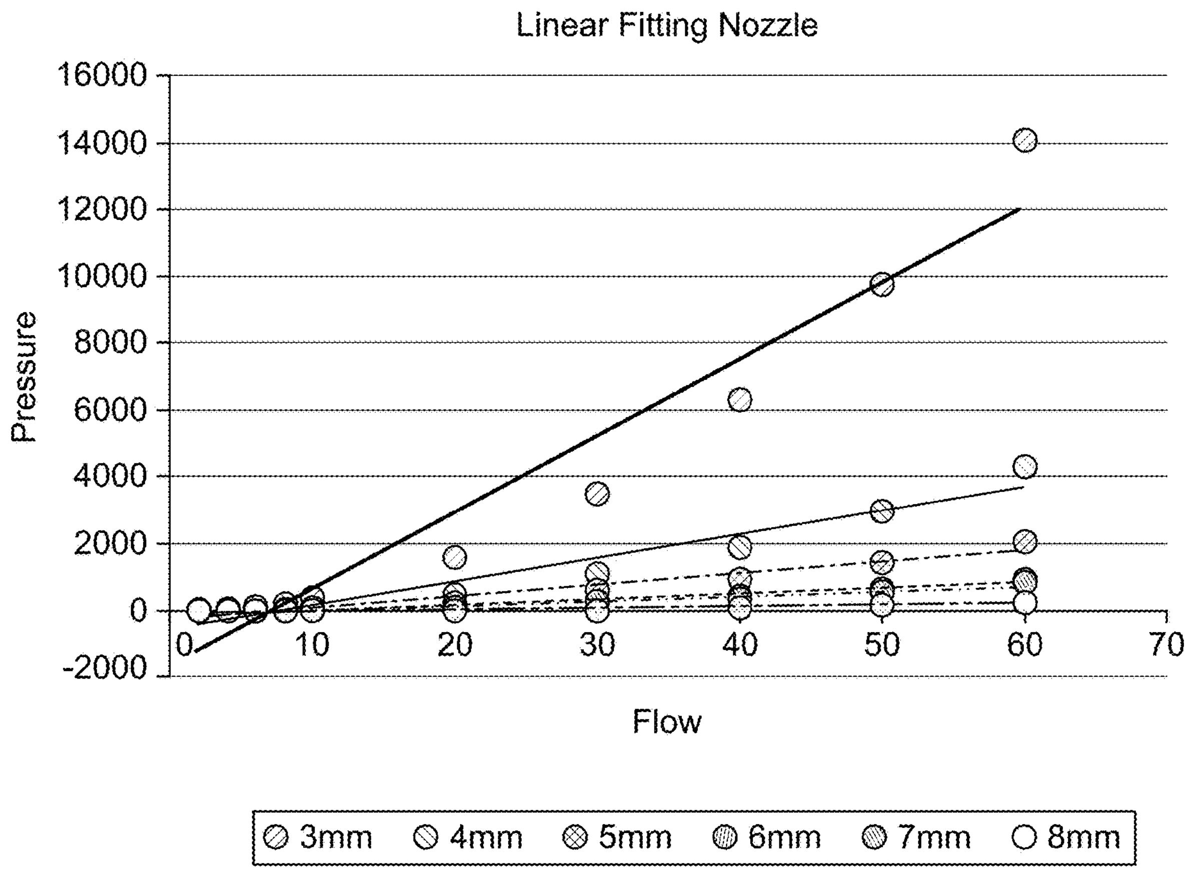
FIG. 30B is a graphical representation showing a linear fitting curve of a nozzle restriction unit, according to certain embodiments.
Figure 31A:
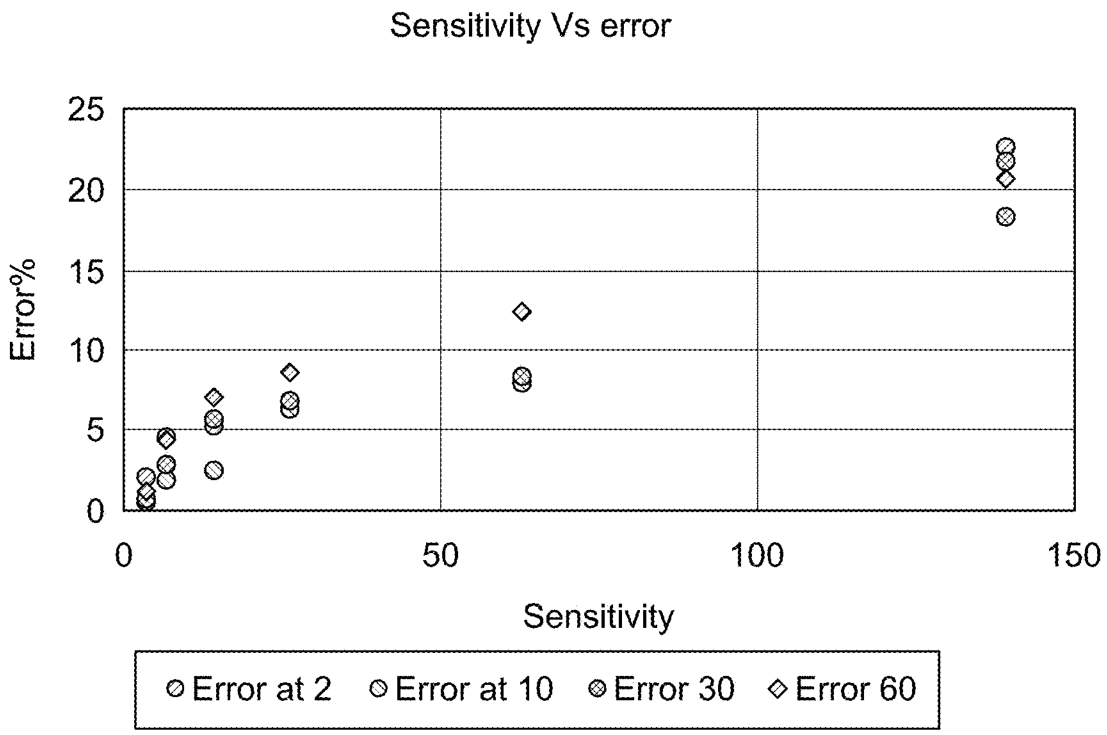
FIG. 31A is a graphical representation showing an error-sensitivity curve of the modified orifice restriction unit, according to certain embodiments.
Figure 31B:
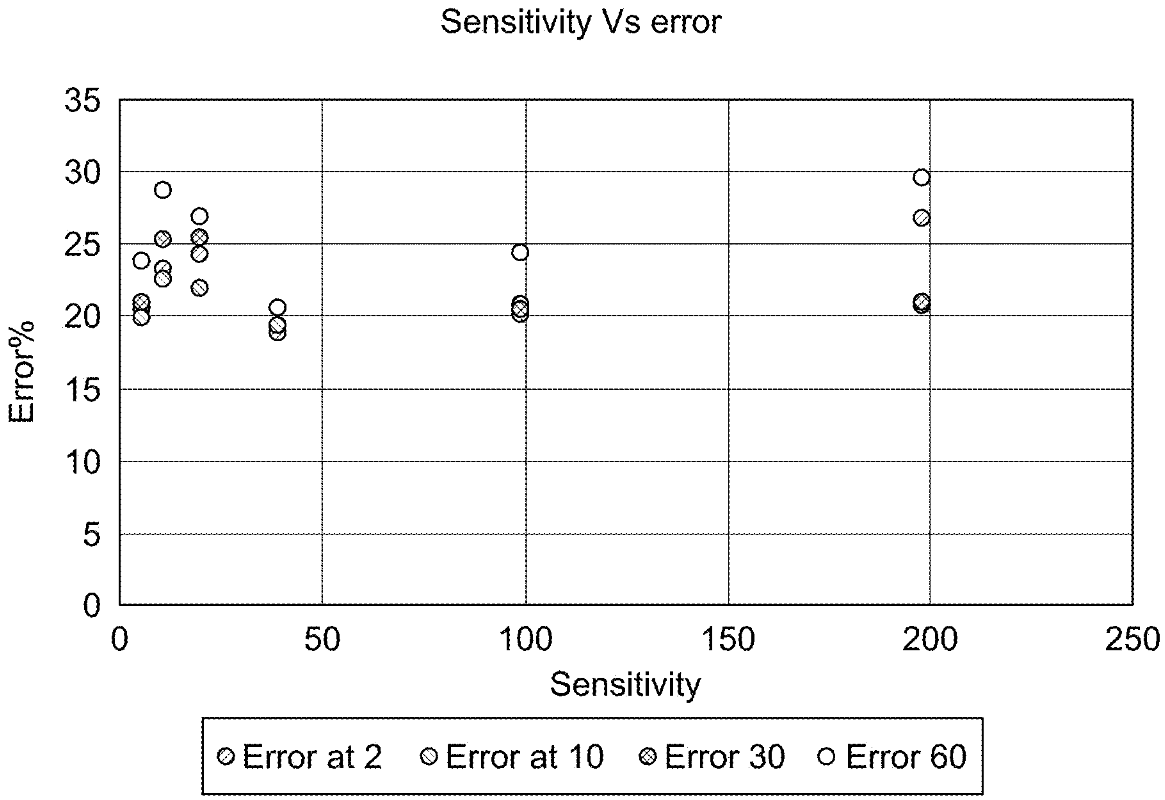
FIG. 31B is a graphical representation showing an error-sensitivity curve of the basic orifice restriction unit, according to certain embodiments.
Figure 32A:
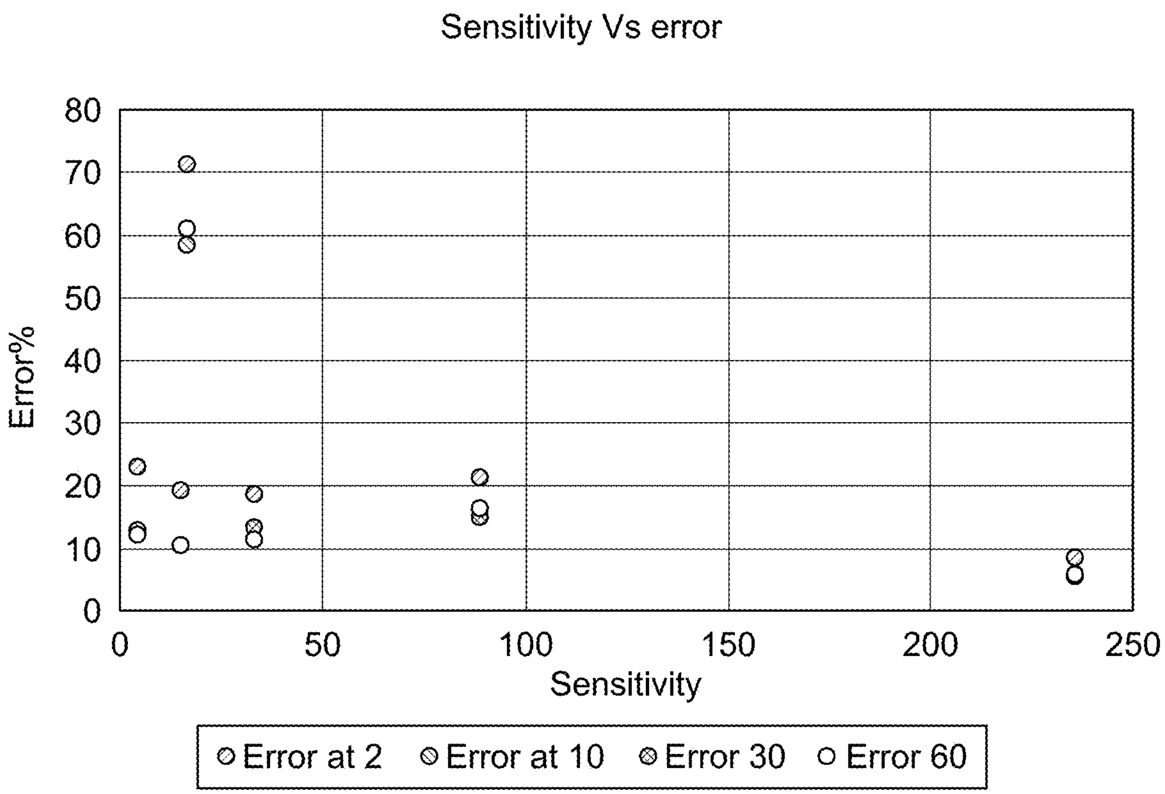
FIG. 32A is a graphical representation showing an error-sensitivity curve of the venturi restriction unit, according to certain embodiments.
Figure 32B:
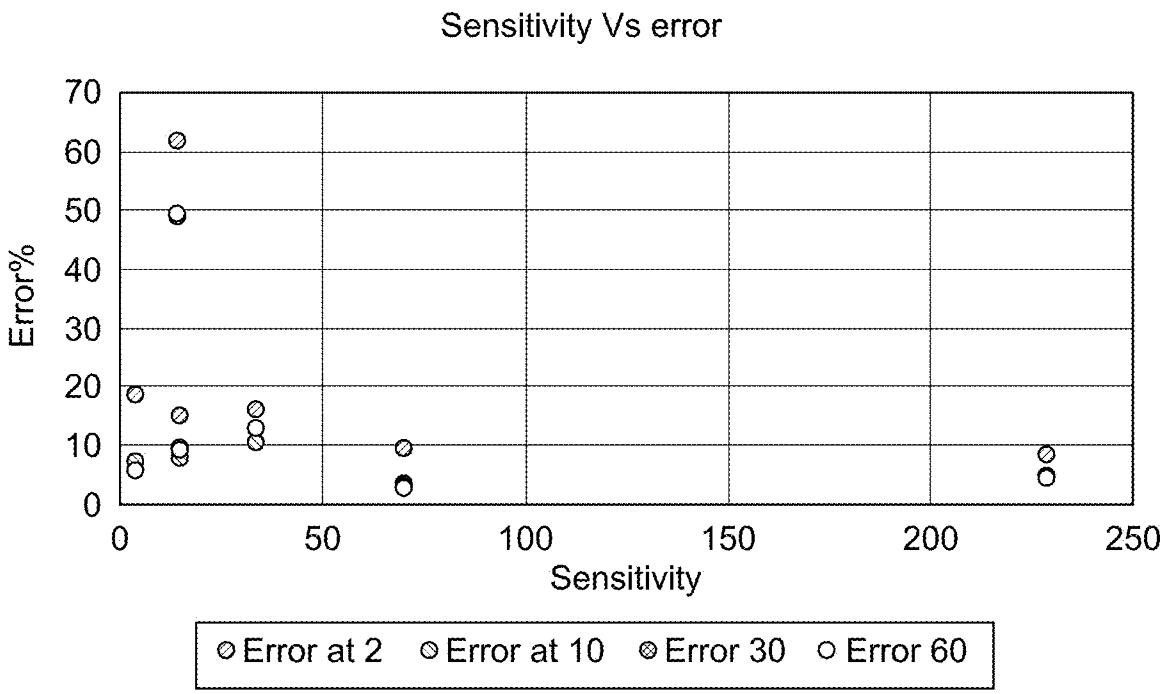
FIG. 32B is a graphical representation showing an error-sensitivity curve of the nozzle restriction unit, according to certain embodiments.

According to the present disclosure, the differential pressure flow meter 100 is cost effective compared to the available commercial flow sensors. As shown in FIG. 27, the cost of the differential pressure flow meter 100 of the present disclosure is cheaper than the available flow sensors such as Hamilton Medical flow sensor, SpiroQuant P flow sensor, and Drager Ventilator Flow Sensor. The modified orifice restriction unit 630 was fabricated using the 3D printing method with Nylon filament. As shown in FIG. 28, the Nylon filament for 3D printing procedure is considered to be cheap when comparing it with other metallic filament such as stainless-steel, and aluminium filament. Further, Nylon material is more cost effective than the stainless steel and aluminium especially for disposable medical applications such as the disposable differential pressure flow meter 100 of the present disclosure.

The modified orifice restriction unit 630 of the present disclosure is printed by the 3D printing method for the testing purpose. However, the modified orifice restriction unit 630 can be manufactured by injection molding for large scale production. The injection molding can be performed in steps as given below:

- A 3D model should be manufactured using the 3D printing method.
- A mold can be filled with a material to model a certain shape of the modified orifice restriction unit 630. The most common molding type is the bi-valve molding, which uses two molds for each half of the object. The bi-valve molding type is used in the present disclosure as the stainless steel is used as raw material.
- A material is then injected to the mold. The material can be a liquid or a pliable raw material such as glass, plastic, ceramic or metal.
- After some time, the injected material dries out and forms the desired shape of the modified orifice restriction unit 630.
- The two halves are joined by soldering them together to create the desired shape of the modified orifice restriction unit 630.

Example 18: Design Verification

To verify the final design of the restriction unit used in the present disclosure, error-sensitivity curve was plotted for all designs using all of their diameters (3-8 mm). First, the error of each diameter was found by the following error equation, which compare between the actual and the calculated-real-measurements [See: Javanbakht, Samaneh. (2015). Error calculation for beginners an example-oriented introduction for students of the TUHH, which is incorporated herein by reference in its entirety]

$$\text{Error} = \frac{\text{Measured value} - \text{True value}}{\text{True value}} \times 100 \tag{9}$$

Where the true value is calculated by the flow equations and the measured value is the one recorded in the simulation program. The sensitivity of each diameter was found by obtaining the Flow-Pressure curve and taking the slop of the best fitting linear line, as shown in FIG. 29A to FIG. 30B. The error-sensitivity curve was plotted for all models separately, as shown in FIG. 31A to FIG. 32B, to find out the diameter to be used that has a good sensitivity with acceptable error.

Figure 33:
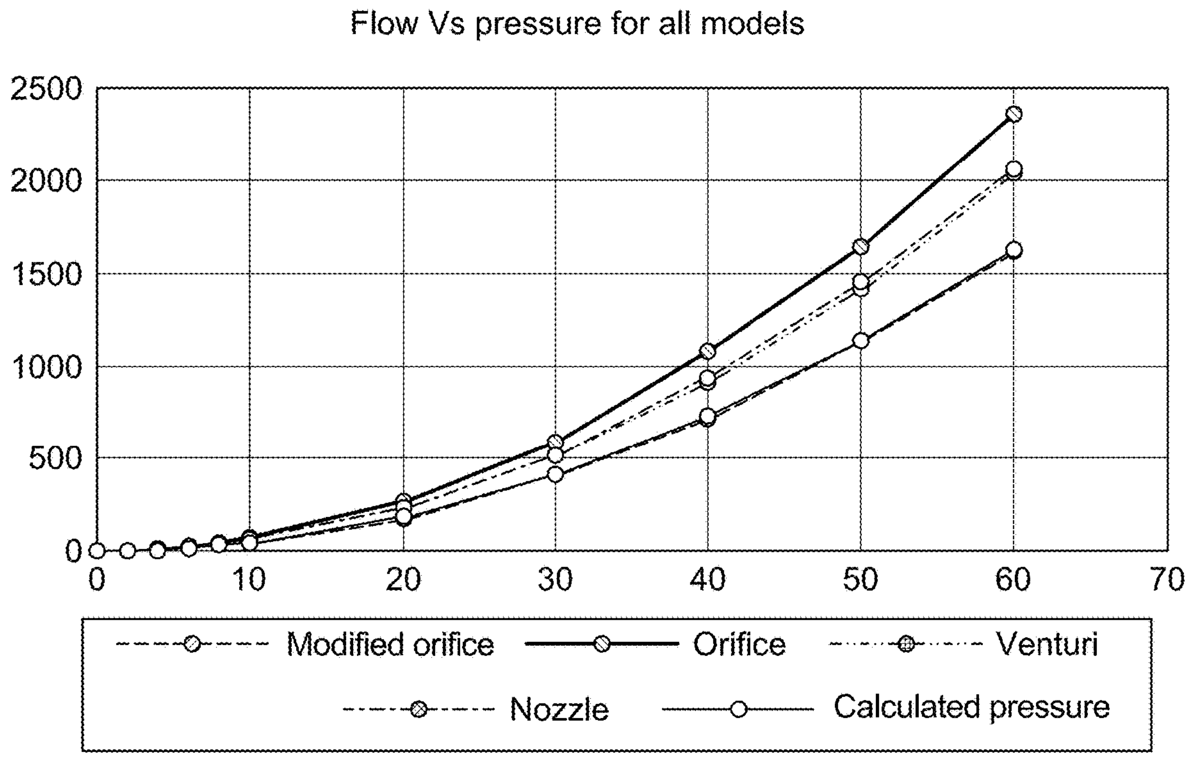
FIG. 33 is a graphical representation showing comparison of flow vs pressure drop of the modified orifice, the basic orifice, the venturi, and the nozzle restriction units, according to certain embodiments.

It was observed that the orifice design has the highest error, while the venturi and nozzle have low error comparing to the two first designs. From each design, the 5 mm design was chosen as the moderate since it has a good sensitivity with acceptable error value. The 5 mm designs from each model were compared in term of their accuracy, sensitivity, and error values. When the results were compared, it was observed that the modified orifice design has the lowest error, and its behavior was the closest to the calculated value. As shown in FIG. 33, the modified orifice curve is almost identical to the calculated one, making the modified orifice the best design for the present disclosure.

Figure 34:
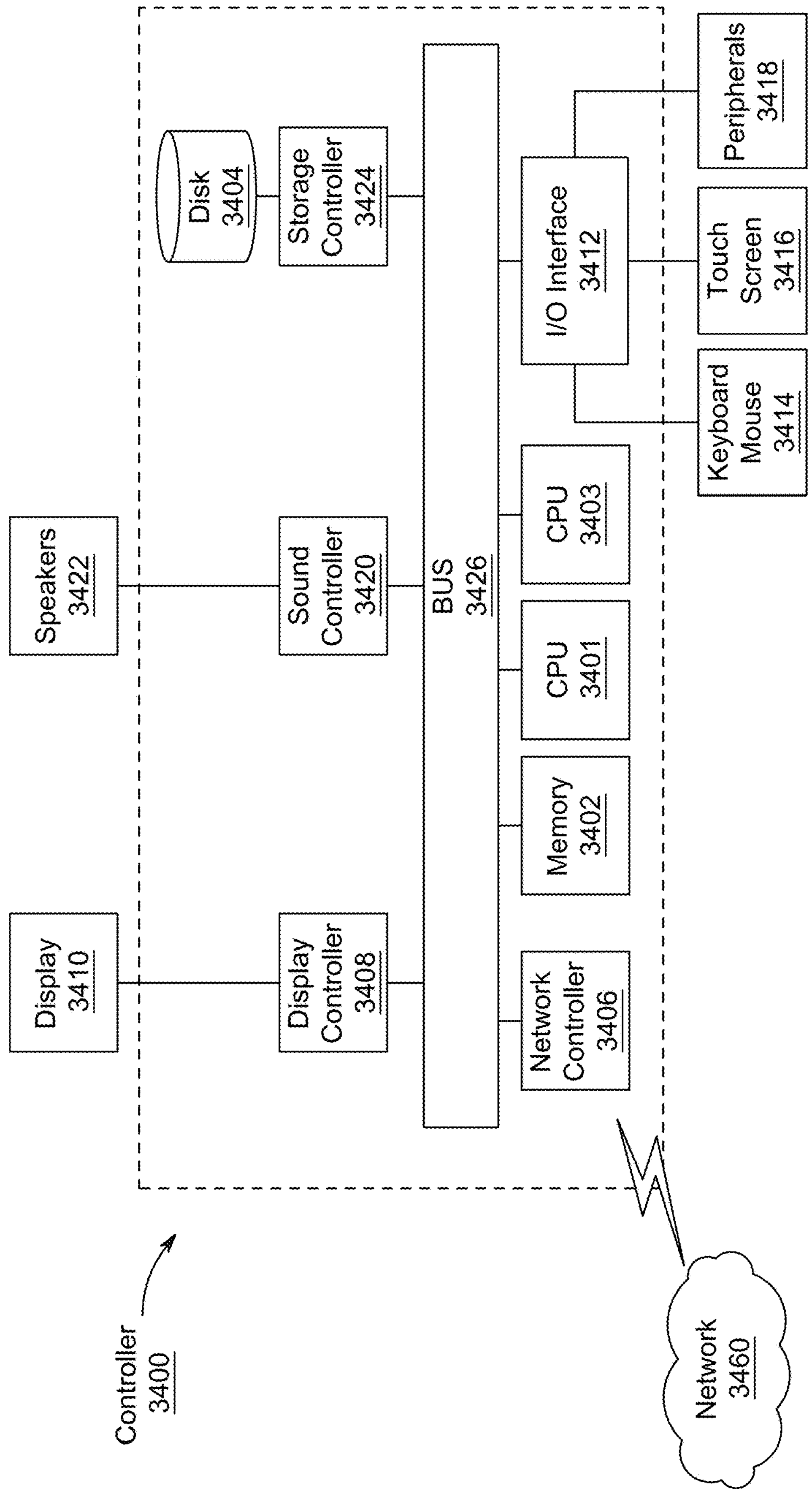
FIG. 34 is an illustration of a non-limiting example of details of computing hardware used in a computing system of the HFNC system of FIG. 4, according to certain embodiments.

Next, further details of the hardware description of the computing environment according to exemplary embodiments is described with reference to FIG. 34. In FIG. 34, a controller 3400 is described is representative of the computing device 146 of FIG. 1 in which the controller is a computing device which includes a CPU 3401 which performs the processes described above/below. The process data and instructions may be stored in memory 3402. These processes and instructions may also be stored on a storage medium disk 3404 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 3401, 3403 and an operating system such as Microsoft Windows 7, Microsoft Windows 10, Microsoft Windows 11, UNIX, Solaris, LINUX, Apple MAC-OS and other systems known to those skilled in the art.

The hardware elements in order to achieve the computing device may be realized by various circuitry elements, known to those skilled in the art. For example, CPU 3401 or CPU 3403 may be a Xenon or Core processor from Intel of America or an Opteron processor from AMD of America, or may be other processor types that would be recognized by one of ordinary skill in the art. Alternatively, the CPU 3401, 3403 may be implemented on an FPGA, ASIC, PLD or using discrete logic circuits, as one of ordinary skill in the art would recognize. Further, CPU 3401, 3403 may be implemented as multiple processors cooperatively working in parallel to perform the instructions of the inventive processes described above.

The computing device in FIG. 34 also includes a network controller 3406, such as an Intel Ethernet PRO network interface card from Intel Corporation of America, for interfacing with network 3460. As can be appreciated, the network 3460 can be a public network, such as the Internet, or a private network such as an LAN or WAN network, or any combination thereof and can also include PSTN or ISDN sub-networks. The network 3460 can also be wired, such as an Ethernet network, or can be wireless such as a cellular network including EDGE, 3G, 4G and 5G wireless cellular systems. The wireless network can also be WiFi, Bluetooth, or any other wireless form of communication that is known.

The computing device further includes a display controller 3408, such as a NVIDIA GeForce GTX or Quadro graphics adaptor from NVIDIA Corporation of America for interfacing with display 3410, such as a Hewlett Packard HPL2445w LCD monitor. A general purpose I/O interface 3412 interfaces with a keyboard and/or mouse 3414 as well as a touch screen panel 3416 on or separate from display 3410. General purpose I/O interface also connects to a variety of peripherals 3418 including printers and scanners, such as an OfficeJet or DeskJet from Hewlett Packard.

A sound controller 3420 is also provided in the computing device such as Sound Blaster X-Fi Titanium from Creative, to interface with speakers/microphone 3422 thereby providing sounds and/or music.

The general purpose storage controller 3424 connects the storage medium disk 3404 with communication bus 3426, which may be an ISA, EISA, VESA, PCI, or similar, for interconnecting all of the components of the computing device. A description of the general features and functionality of the display 3410, keyboard and/or mouse 3414, as well as the display controller 3408, storage controller 3424, network controller 3406, sound controller 3420, and general purpose I/O interface 3412 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 35.

Figure 35:
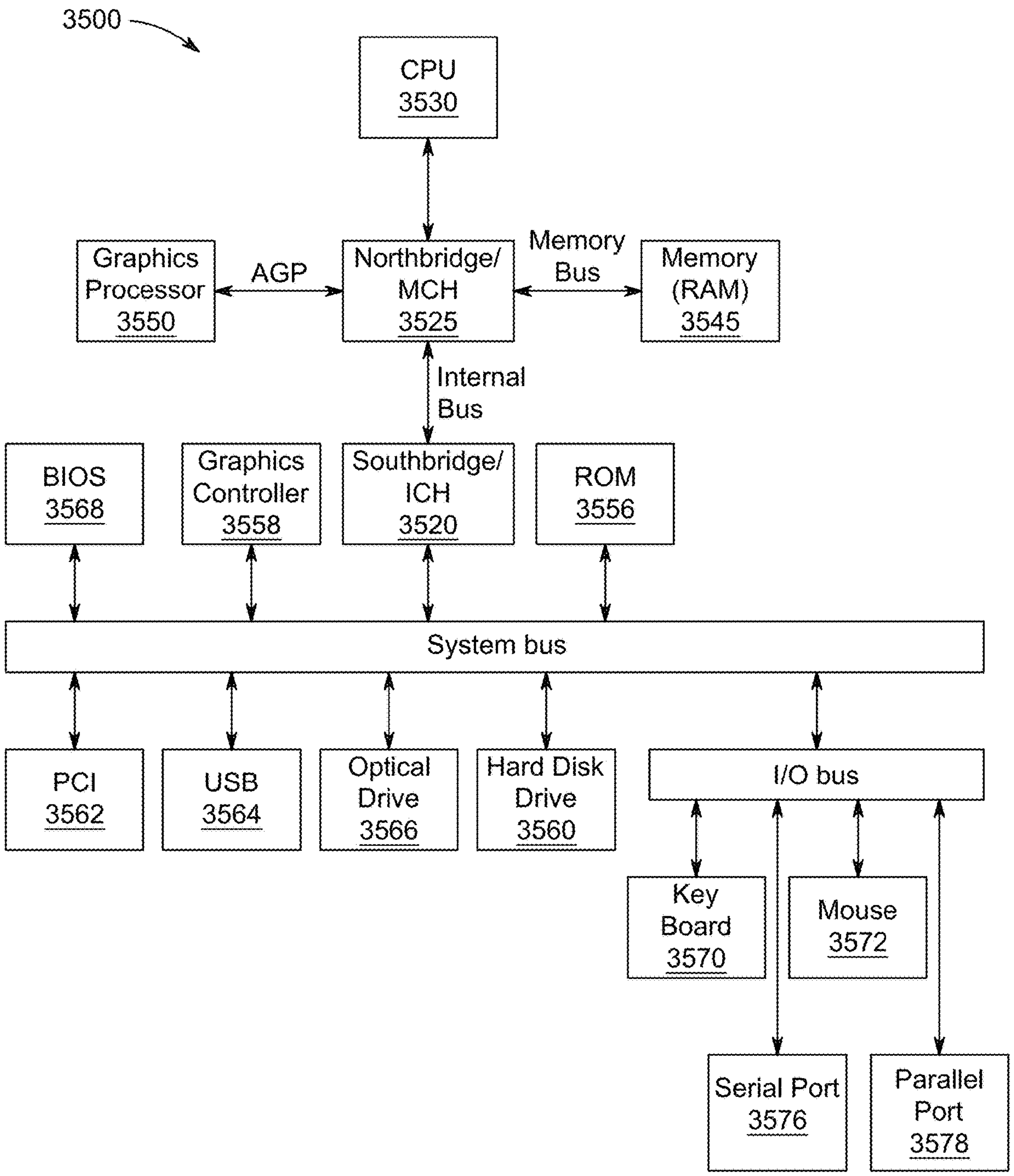
FIG. 35 is an exemplary schematic diagram of a data processing system used within the computing system, according to certain embodiments.

FIG. 35 shows a schematic diagram of a data processing system, according to certain embodiments, for performing the functions of the exemplary embodiments. The data processing system is an example of a computer in which code or instructions implementing the processes of the illustrative embodiments may be located.

In FIG. 35, data processing system 3500 employs a hub architecture including a north bridge and memory controller hub (NB/MCH) 3525 and a south bridge and input/output (I/O) controller hub (SB/ICH) 3520. The central processing unit (CPU) 3530 is connected to NB/MCH 3525. The NB/MCH 3525 also connects to the memory 3545 via a memory bus, and connects to the graphics processor 3550 via an accelerated graphics port (AGP). The NB/MCH 3525 also connects to the SB/ICH 3520 via an internal bus (e.g., a unified media interface or a direct media interface). The CPU Processing unit 3530 may contain one or more processors and even may be implemented using one or more heterogeneous processor systems.

Figure 36:
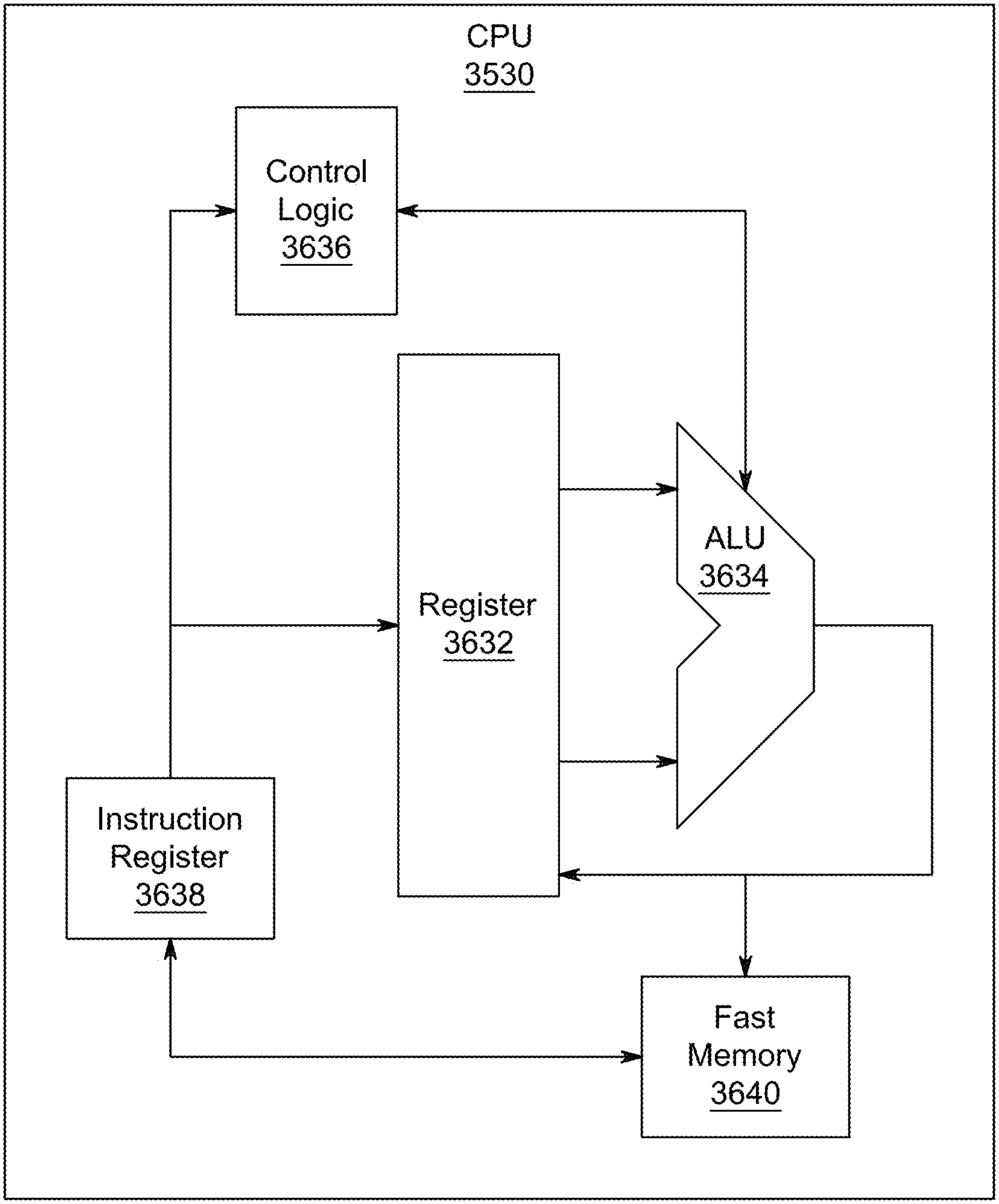
FIG. 36 is an exemplary schematic diagram of a processor used with the computing system, according to certain embodiments.

For example, FIG. 36 shows one implementation of CPU 3530. In one implementation, the instruction register 3638 retrieves instructions from the fast memory 3640. At least part of these instructions are fetched from the instruction register 3638 by the control logic 3636 and interpreted according to the instruction set architecture of the CPU 3530. Part of the instructions can also be directed to the register 3632. In one implementation the instructions are decoded according to a hardwired method, and in another implementation the instructions are decoded according to a microprogram that translates instructions into sets of CPU configuration signals that are applied sequentially over multiple clock pulses. After fetching and decoding the instructions, the instructions are executed using the arithmetic logic unit (ALU) 3634 that loads values from the register 3632 and performs logical and mathematical operations on the loaded values according to the instructions. The results from these operations can be feedback into the register and/or stored in the fast memory 3640. According to certain implementations, the instruction set architecture of the CPU 3530 can use a reduced instruction set architecture, a complex instruction set architecture, a vector processor architecture, a very large instruction word architecture. Furthermore, the CPU 3530 can be based on the Von Neuman model or the Harvard model. The CPU 3530 can be a digital signal processor, an FPGA, an ASIC, a PLA, a PLD, or a CPLD. Further, the CPU 3530 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 35, the data processing system 3500 can include that the SB/ICH 3520 is coupled through a system bus to an I/O Bus, a read only memory (ROM) 3556, universal serial bus (USB) port 3564, a flash binary input/output system (BIOS) 3568, and a graphics controller 3558. PCI/PCIe devices can also be coupled to SB/ICH 3588 through a PCI bus 3562.

The PCI devices may include, for example, Ethernet adapters, add-in cards, and PC cards for notebook computers. The Hard disk drive 3560 and CD-ROM 3566 can use, for example, an integrated drive electronics (IDE) or serial advanced technology attachment (SATA) interface. In one implementation the I/O bus can include a super I/O (SIO) device.

Further, the hard disk drive (HDD) 3560 and optical drive 3566 can also be coupled to the SB/ICH 3520 through a system bus. In one implementation, a keyboard 3570, a mouse 3572, a parallel port 3578, and a serial port 3576 can be connected to the system bus through the I/O bus. Other peripherals and devices that can be connected to the SB/ICH 3520 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

According to the present disclosure, the differential pressure flow meter 100 was developed for the HNFC therapy to continuously ventilate patients in need. The differential pressure flow meter 100 includes the fluid restriction unit 102 and the differential pressure transducer 104 having the strain gauge sensor to provide the readings of the flow rates in order to adjust the flow rate and provide an accurate ventilation. The orifice restriction units of the present disclosure provide high accuracy measurements of differential pressure, while having a low production and operation cost. The orifice restriction is placed inside the pipe, perpendicular to the flow of fluid stream. The restriction has the smaller diameter than the pipe, which increases the velocity of the fluid stream transferring through the pipe. The pressure drop is measured by the differential pressure transducer 104, which can be eventually related to the flow rate by Bernoulli's equation. A modified orifice restriction with rounded edges was used in order to reduce the turbulence effect caused by the sharp edges in the basic orifice restriction. The design of the present disclosure was simulated using the software simulation for fluid dynamics called Ansys Fluent. Four different types of flow meters (orifice, venturi, modified orifice, and modified venturi) were designed and tested to determine a favorable design for use in an HNFC application. The trial & error method was used by varying the flow rate value between 10-60 L/min, with an increment of 10 L/min each time to measure higher flow rates. In addition, the differential diameter of each flow rate was varied between 3-8 mm, with an increment of 1 mm, in order to find the best diameter. The best diameter is the diameter with the highest pressure drop sensitivity to flow. Moreover, the simulation for the lower flow ranges of 2-8 L/min was tested with an increment of 2 L/min each time to achieve a design that can serve all applications for higher and lower ranges in all conditions and ages. The modified orifice-5 mm was identified as the best model with the highest sensitivity, lowest error and lowest turbulence. Moreover, the modified orifice model was constructed to have lower turbulence effect than the basic orifice model. The strain gauge sensor was used as a pressure transducer to measure the pressure drop with the highest sensitivity to flow changes. Strain gauge sensors are small in size, and have high accuracy and very high sensitivity to the changes in flow rate. Laser sensor can provide higher accuracy than using strain gauge sensors. The differential pressure flow meter 100 may be used for the HNFC therapy along with a feedback system to give precise values with lower errors so the flow value can be adjusted automatically.

Numerous modifications and variations of the present disclosure are possible in light of the above teachings. It is therefore to be understood that within the scope of the appended claims, the invention may be practiced otherwise than as specifically described herein.

The invention claimed is:

1. A method of monitoring and regulating a flow rate of a fluid composition generated by a nasal cannula, the method comprises:

configuring the nasal cannula with a differential pressure flow meter by introducing the fluid composition to a fluid restriction unit via an upstream compartment to generate a high-pressure fluid flow, wherein the differential pressure flow meter comprises the fluid restriction unit, comprising:

the upstream compartment, a downstream compartment, a first fluid outlet port on the upstream compartment, a second fluid outlet port on the downstream compartment, and an orifice element having a centric bore;

wherein the orifice element is located at a junction face of the upstream compartment and the downstream compartment, and is in a circular cross section of the fluid restriction unit, and wherein the orifice element is configured to flow a fluid from the upstream compartment to the downstream compartment through an upstream side of the orifice element to a downstream side of the orifice element via the centric bore;

wherein each of the upstream compartment and the downstream compartment are in a shape of a hollow cylinder having substantially same inner diameter (D) and wall thickness; and a differential pressure transducer, comprising:

a diaphragm compartment having a high-pressure side diaphragm, a low-pressure side diaphragm, a first sensor operatively coupled to the high-pressure side diaphragm, and a second sensor operatively coupled to the low-pressure side diaphragm; and a chamber having a high-pressure compartment and a low-pressure compartment, wherein the high-pressure compartment and the low-pressure compartment are separated by the diaphragm compartment, wherein the high-pressure compartment is in fluid communication with the upstream compartment of the fluid restriction unit via the first fluid outlet port, and wherein the low-pressure compartment is in fluid communication with the downstream compartment of the fluid restriction unit via the second fluid outlet port;

wherein the high-pressure fluid flow is in fluid communication with the high-pressure compartment of the chamber via the first fluid outlet port;

passing the fluid composition through the downstream compartment of the fluid restriction unit to generate a low-pressure fluid flow;

wherein the low-pressure fluid flow is in fluid communication with the low-pressure compartment of the chamber via the second fluid outlet port;

simultaneously measuring a deformation of the high-pressure side diaphragm caused by the high-pressure fluid flow by the first sensor, and a deformation of the low-pressure side diaphragm caused by the low-pressure fluid flow by the second sensor; and converting the deformation into the electrical signal which is numerically digitally displayed and visually displayed to monitor and regulating a flow rate of the fluid composition generated by the nasal cannula.

2. The method of claim 1, wherein the fluid composition comprises air, oxygen, and moisture.

3. The method of claim 1, wherein the flow rate of the fluid composition is in a range of 1 to 80 liters per minute (L/min).

4. The method of claim 1, wherein the flow rate measure has an error of less than 30%.

5. The method of claim 1, wherein the centric bore of the orifice element of the differential pressure flow meter has a diameter (d), and wherein d is in a range of 0.224D to 0.742D.

6. The method of claim 5, wherein the orifice element has a semicircle edge, wherein the semicircle edge has an average thickness of no more than 1.0d.

7. The method of claim 5, wherein the orifice element has a maximum thickness (E), and an inner-facing edge with a semicircular cross-sectional profile having a radius E, wherein E is no more than 1.5d.

8. The method of claim 1, wherein the first fluid outlet port on the upstream compartment and the second fluid outlet port on the downstream compartment of the differential pressure flow meter have substantially a same inner diameter of 0.1D.

9. The method of claim 1, wherein a first distance ($d_1$) between a center of the first fluid outlet port on the upstream compartment to the upstream side of the orifice element of the differential pressure flow meter is substantially same as a second distance ($d_2$) between the center of the second fluid outlet port on the downstream compartment to the downstream side of the orifice element.

10. The method of claim 9, wherein $d_1$ and $d_2$ of the differential pressure flow meter are in a range of 0.25D to 1.0D.

11. The method of claim 1, wherein the differential pressure flow meter has having a length of 40 to 80 millimeters (mm).

12. The method of claim 1, wherein the inner diameter (D) of the upstream compartment and the downstream compartment of the differential pressure flow meter is in a range of 6 to 20 mm.

13. The method of claim 1, wherein the wall thickness of the upstream compartment and the downstream compartment of the differential pressure flow meter is in a range of 0.5 to 4 mm.

14. The method of claim 1, wherein the first sensor is at least one selected from the group consisting of a laser sensor, and a strain gauge sensor, and wherein the second sensor is at least one selected from the group consisting of a laser sensor, and a strain gauge sensor.

15. The method of claim 1, wherein the first sensor and the second sensor are connected to a microcontroller, wherein the microcontroller is further connected to a computing device, and wherein the computing device has a communications interface coupled to the microcontroller.

16. The method of claim 1, wherein the fluid restriction unit of the differential pressure flow meter is made of polyamide by 3D printing.

17. The method of claim 1, wherein a diaphragm of the diaphragm compartment of the differential pressure flow meter is made of silicon.

* * * * *